United States Patent
Marubashi et al.

(10) Patent No.: US 11,160,313 B2
(45) Date of Patent: Nov. 2, 2021

(54) AEROSOL INHALER AND POWER SUPPLY UNIT OF AEROSOL INHALER

(71) Applicant: Japan Tobacco Inc., Tokyo (JP)

(72) Inventors: Keiji Marubashi, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 17/218,175

(22) Filed: Mar. 31, 2021

(65) Prior Publication Data

US 2021/0307406 A1 Oct. 7, 2021

(30) Foreign Application Priority Data

Apr. 2, 2020 (JP) .............................. JP2020-066571

(51) Int. Cl.
*A24F 40/57* (2020.01)
*A61M 15/00* (2006.01)
(Continued)

(52) U.S. Cl.
CPC .......... *A24F 40/57* (2020.01); *A61M 15/009* (2013.01); *G05B 15/02* (2013.01); *A24F 40/10* (2020.01);
(Continued)

(58) Field of Classification Search
CPC .......... A24F 40/57; A24F 40/20; A24F 40/30; A24F 40/10; A61M 15/009;
(Continued)

(56) References Cited

U.S. PATENT DOCUMENTS 4,922,901 A * 5/1990 Brooks ............... A61M 16/109
128/203.26
4,947,874 A * 8/1990 Brooks ................... A24F 40/46
131/329
(Continued)

FOREIGN PATENT DOCUMENTS

CN 208354611 U 1/2019
JP 61-18594 U 2/1986
(Continued)

OTHER PUBLICATIONS

Notice of Reasons for Refusal dated Jul. 7, 2020, received for JP Application 2020-066571, 5 pages including English Translation.
(Continued)

*Primary Examiner* — Truc T Nguyen
(74) *Attorney, Agent, or Firm* — Xsensus LLP

(57) ABSTRACT

An aerosol inhaler includes: a first branch circuit including a load, a first resistor, and a first node; a second branch circuit including a second resistor, a third resistor, and a second node; an operational amplifier of which a non-inverting input terminal is connected to one of the first node and the second node, and of which an inverting input terminal is connected to the other of the first node and the second node; and a control device having an upper limit temperature and a lower limit temperature. A differential input of the operational amplifier is larger than potential of a negative power supply terminal of the operational amplifier or a minimum value acquirable by the operational amplifier in a first temperature range, and is equal to the potential of the negative power supply terminal of the operational amplifier or the minimum value in a second temperature range.

11 Claims, 26 Drawing Sheets

(51) Int. Cl.
*G05B 15/02* (2006.01)
*A24F 40/10* (2020.01)
*A24F 40/30* (2020.01)
*A24F 40/20* (2020.01)

(52) U.S. Cl.
CPC .............. *A24F 40/20* (2020.01); *A24F 40/30* (2020.01); *A61M 2205/3368* (2013.01); *A61M 2205/3653* (2013.01); *A61M 2205/8206* (2013.01)

(58) Field of Classification Search
CPC .. A61M 2205/8206; A61M 2205/3368; A61M 2205/3653; G05B 15/02
See application file for complete search history.

(56) References Cited

U.S. PATENT DOCUMENTS

| | | | | |
|---|---|---|---|---|
| 4,947,875 A | * | 8/1990 | Brooks | A24F 40/46 131/330 |
| 2007/0144514 A1 | * | 6/2007 | Yeates | B01D 45/08 128/203.15 |
| 2011/0080151 A1 | * | 4/2011 | Rahardjo | G05F 1/66 323/285 |
| 2011/0226236 A1 | * | 9/2011 | Buchberger | A61K 31/465 128/200.23 |
| 2019/0175847 A1 | * | 6/2019 | Pocreva, III | G09B 23/28 |
| 2020/0358300 A1 | * | 11/2020 | Akao | H02J 7/00712 |
| 2021/0120882 A1 | | 4/2021 | Marubashi | |

FOREIGN PATENT DOCUMENTS

| | | |
|---|---|---|
| JP | 2017-501805 A | 1/2017 |
| JP | 6667708 B1 | 3/2020 |
| JP | 6667709 B1 | 3/2020 |
| WO | 2015/100361 A1 | 7/2015 |

OTHER PUBLICATIONS

Decision to Grant dated Oct. 6, 2020, received for JP Application 2020-066571, 5 pages including English Translation.
European Search Report dated Aug. 3, 2021 in European Patent Application No. 21166270.5, 4 pages.

* cited by examiner

US 11,160,313 B2

AEROSOL INHALER AND POWER SUPPLY UNIT OF AEROSOL INHALER

CROSS-REFERENCE TO RELATED APPLICATION

This application is based on and claims priority under 35 USC 119 from Japanese Patent Application No. 2020-066571 filed on Apr. 2, 2020, the contents of which are incorporated herein by reference.

TECHNICAL FIELD

The present invention relates to an aerosol inhaler and a power supply unit of an aerosol inhaler.

BACKGROUND

JP-T-2017-501805 discloses a circuit configured to measure a resistance value of a heater in a device that generates an inhalable aerosol.

Since the aerosol inhaler is used by a user holding the aerosol inhaler in his or her mouth, temperature control of the heater used to generate the aerosol is important. JP-T-2017-501805 discloses measurement of the resistance value of the heater, but does not disclose a specific configuration thereof.

An object of the present invention is to provide an aerosol inhaler and a power supply unit of an aerosol inhaler capable of detecting, with high accuracy in an appropriate temperature range, a temperature of a load used for generating an aerosol.

SUMMARY

A first invention is an aerosol inhaler includes:

a first branch circuit that includes a load, which heats an aerosol source and whose electric resistance value has correlation with a temperature thereof, a first known resistor, and a first node connecting the load and the first known resistor in series;

a second branch circuit that includes a second known resistor, a third known resistor, and a second node connecting the second known resistor and the third known resistor in series, and that is connected in parallel with the first branch circuit;

an operational amplifier of which a non-inverting input terminal is connected to one of the first node and the second node, and of which an inverting input terminal is connected to the other of the first node and the second node; and a control device having an upper limit temperature for stopping heating the load and a lower limit temperature for not allowing electricity discharge to the load, in which a differential input of the operational amplifier
is equal to potential of a negative power supply terminal of the operational amplifier or a minimum value that is acquirable by the operational amplifier, in an upper-bound temperature range or a lower-bound temperature range of an operating temperature set in which the upper limit temperature is a greatest element and the lower limit temperature is a least element, or
is equal to the potential of the negative power supply terminal of the operational amplifier or a minimum value that is acquirable by the operational amplifier, in a subset of the operating temperature set, the subset including the upper limit temperature or the lower limit temperature.

A second invention is a power supply unit of an aerosol inhaler having a power supply capable of discharging electricity to a load that heats an aerosol generation source and whose electric resistance value has correlation with a temperature thereof, the power supply unit of an aerosol inhaler including:

a first branch circuit that includes a first known resistor, and a first node connecting the load and the first known resistor in series;

a second branch circuit that includes a second known resistor, a third known resistor, and a second node connecting the second known resistor and the third known resistor in series, and that is connected in parallel with the first branch circuit;

an operational amplifier of which a non-inverting input terminal is connected to one of the first node and the second node, and of which an inverting input terminal is connected to the other of the first node and the second node; and a control device having an upper limit temperature for stopping heating the load and a lower limit temperature for not allowing electricity discharge to the load, in which a differential input of the operational amplifier
is equal to potential of a negative power supply terminal of the operational amplifier or a minimum value that is acquirable by the operational amplifier, in an upper-bound temperature range or a lower-bound temperature range of an operating temperature set in which the upper limit temperature is a greatest element and the lower limit temperature is a least element, or
is equal to the potential of the negative power supply terminal of the operational amplifier or a minimum value that is acquirable by the operational amplifier, in a subset of the operating temperature set, the subset including the upper limit temperature or the lower limit temperature.

BRIEF DESCRIPTION OF DRAWINGS

Exemplary embodiments of the present invention will be described in detail based on the following figures, wherein.

DESCRIPTION OF EMBODIMENTS

Hereinafter, an aerosol inhaler and a power supply unit of an aerosol inhaler according to an embodiment of the present invention will be described with reference to the drawings.

(Aerosol Inhaler)

Figure 1:
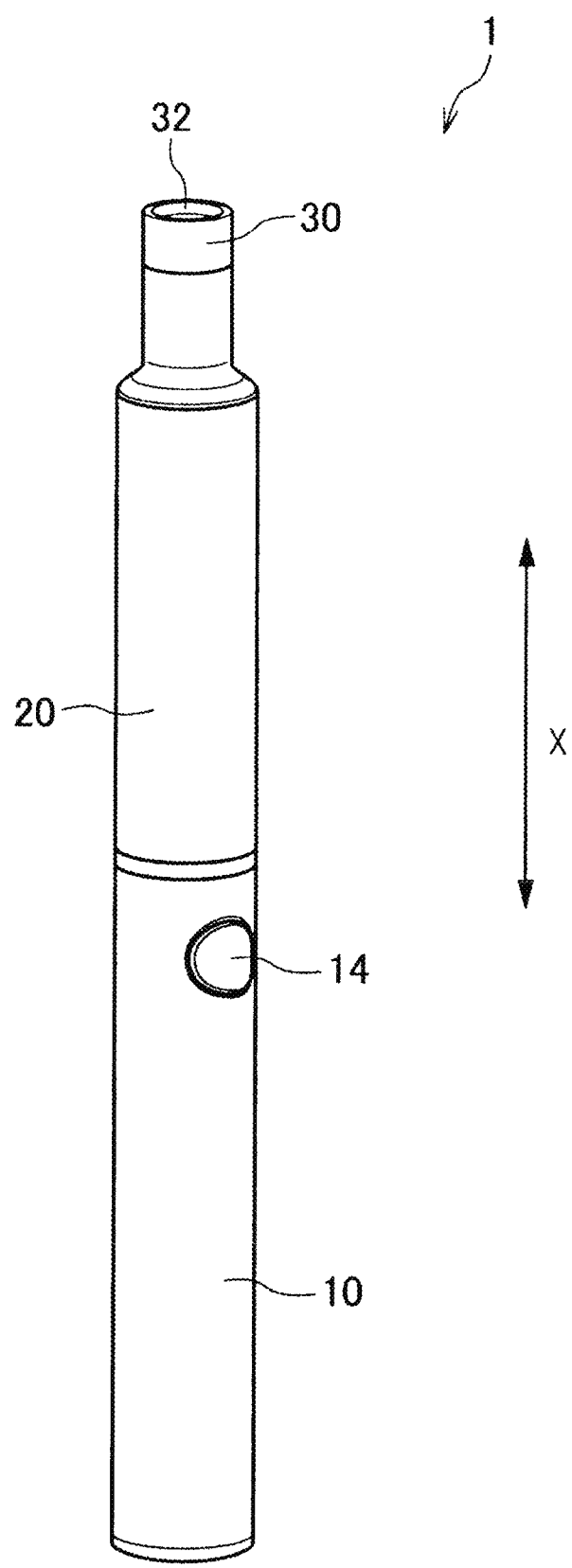
FIG. 1 is a perspective view of an aerosol inhaler according to an embodiment of the invention.
Figure 2:
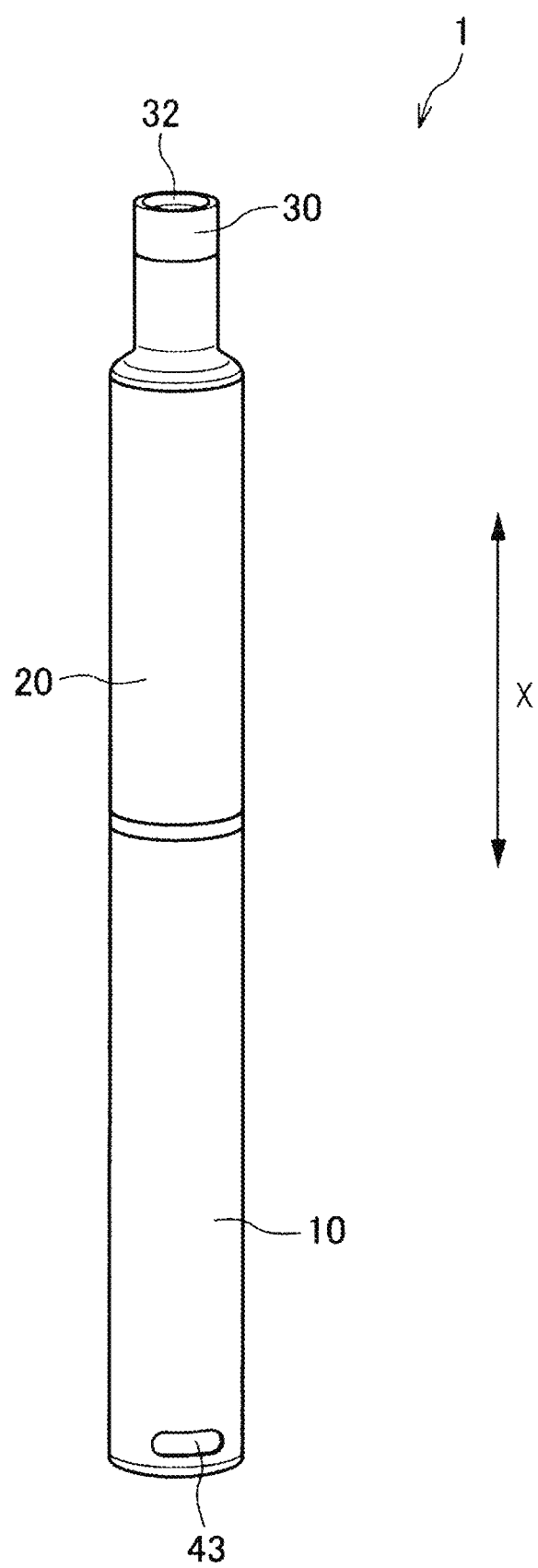
FIG. 2 is another perspective view of the aerosol inhaler shown in FIG. 1.

As shown in FIGS. 1 and 2, an aerosol inhaler 1 is an instrument for inhaling a flavored aerosol without burning, and has a rod shape extending along a predetermined direction (hereinafter referred to as a longitudinal direction X). In the aerosol inhaler 1, a power supply unit 10, a first cartridge 20, and a second cartridge 30 are provided in such an order along the longitudinal direction X. The first cartridge 20 is attachable to and detachable from the power supply unit 10. The second cartridge 30 is attachable to and detachable from the first cartridge 20. In other words, the first cartridge 20 and the second cartridge 30 are replaceable.

(Power Supply Unit)

As shown in FIGS. 3, 4, 5, and 6, the power supply unit 10 accommodates a power supply 12, a charging IC 55A, a micro controller unit (MCU) 50, various sensors such as an intake sensor 15, and the like in a cylindrical power supply unit case 11.

The power supply 12 is a rechargeable secondary battery, an electric double layer capacitor or the like, and is preferably a lithium ion secondary battery. An electrolyte of the power supply 12 may be one of a gel electrolyte, an electrolytic solution, a solid electrolyte, an ionic liquid, or a combination thereof.

Figure 4:
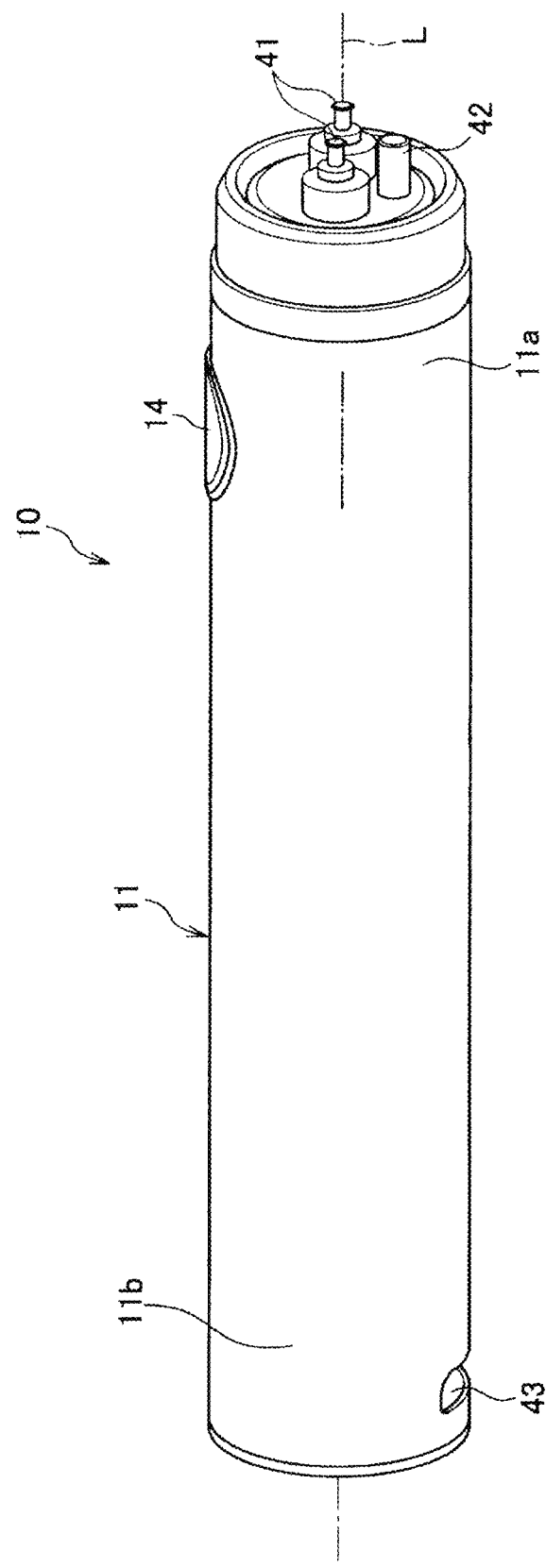
FIG. 4 is a perspective view of a power supply unit of the aerosol inhaler shown in FIG. 1.

As shown in FIG. 4, a discharge terminal 41 is provided on a top portion 11a located on one end side (side of the first cartridge 20) of the power supply unit case 11 in the longitudinal direction X.

The discharge terminal 41 is provided so as to protrude from an upper surface of the top portion 11a toward the first cartridge 20, and is configured to be electrically connectable to a load 21 of the first cartridge 20.

An air supply unit 42 that supplies air to the load 21 of the first cartridge 20 is provided on the upper surface of the top portion 11a in the vicinity of the discharge terminal 41.

A charge terminal 43 that is electrically connectable to an external power supply (not shown) capable of charging the power supply 12 is provided on a bottom portion 11b located on the other end side (side opposite to the first cartridge 20) of the power supply unit case 11 in the longitudinal direction X. The charge terminal 43 is provided on a side surface of the bottom portion 11b, and at least one of a USB terminal, a micro USB terminal, or a Lightning (registered trademark) terminal can be connected thereto, for example.

The charge terminal 43 may be a power receiving unit capable of wirelessly receiving power transmitted from the external power supply. In such a case, the charge terminal 43 (power receiving unit) may be configured with a power receiving coil. A method of non-contact power transfer (wireless power transfer) may be an electromagnetic induction type or a magnetic resonance type. Moreover, the charge terminal 43 may be a power receiving unit capable of contactlessly receiving power transmitted from the external power supply. As another example, the charge terminal 43 is connectable with at least one of a USB terminal, a micro USB terminal, and a Lightning terminal, and may include the power receiving unit described above.

Figure 3:
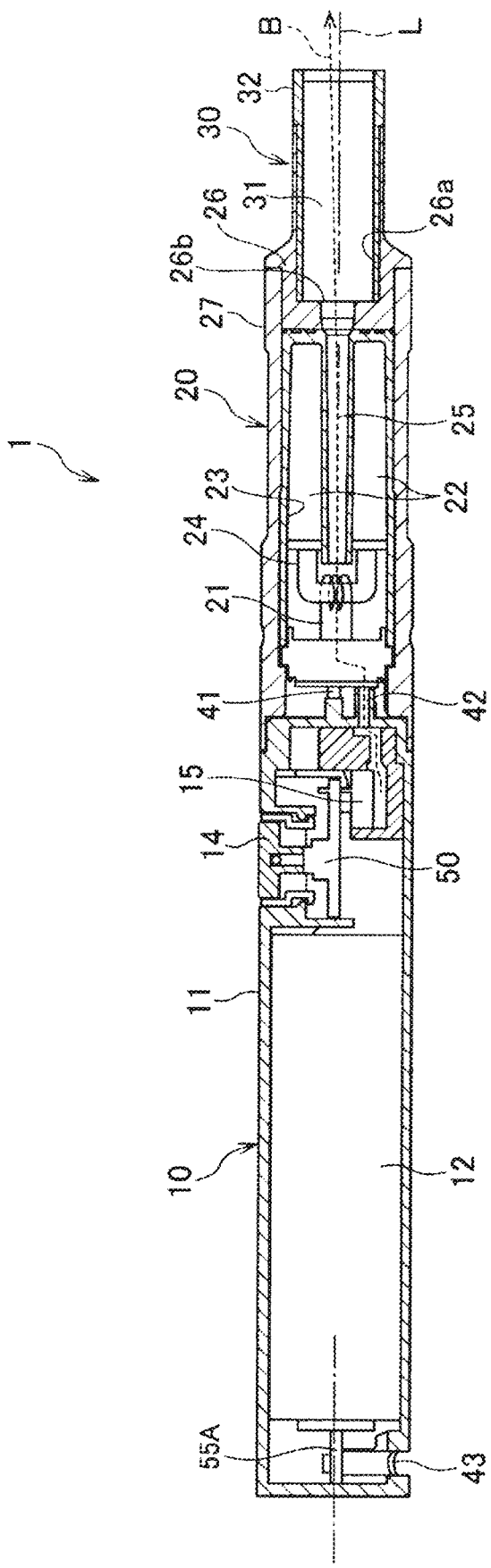
FIG. 3 is a cross-sectional view of the aerosol inhaler shown in FIG. 1.

The power supply unit case 11 is provided with a user-operable operation portion 14 on a side surface of the top portion 11a so as to face a side opposite to the charge terminal 43. More specifically, the operation portion 14 and the charge terminal 43 have a point-symmetric relationship with respect to an intersection of a straight line connecting the operation portion 14 and the charge terminal 43 and a center line of the power supply unit 10 in the longitudinal direction X. The operation portion 14 is configured with a button type switch, a touch panel, or the like. As shown in FIG. 3, the intake sensor 15 that detects a puff operation is provided in the vicinity of the operation portion 14.

The charging IC 55A is disposed close to the charge terminal 43, and controls charging of the power input from the charge terminal 43 to the power supply 12. The charging IC 55A may be disposed in the vicinity of the MCU 50.

Figure 5:
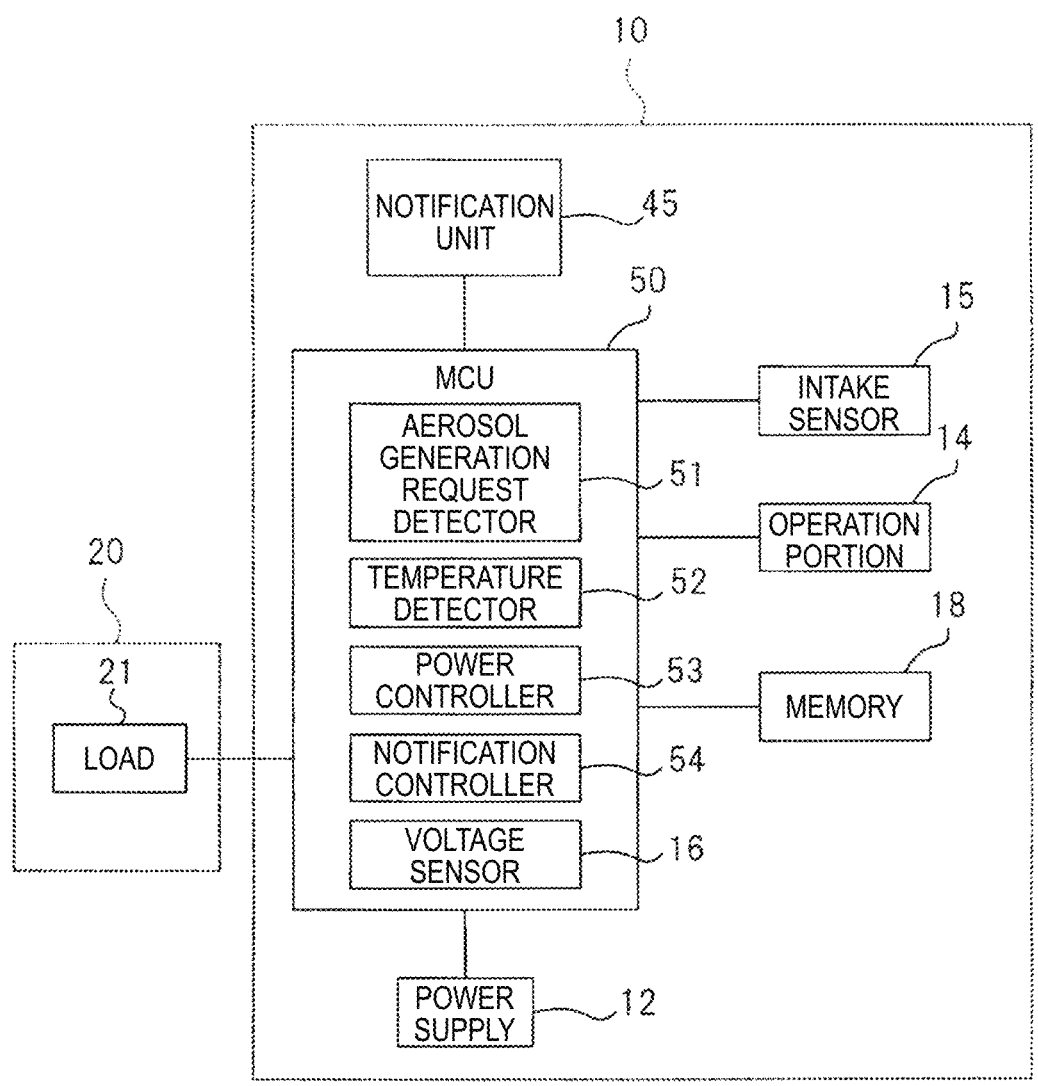
FIG. 5 is a block diagram showing a main part configuration of the power supply unit of the aerosol inhaler shown in FIG. 1.

As shown in FIG. 5, the MCU 50 is connected to various sensor devices such as the intake sensor 15 that detects a puff (intake) operation, the operation portion 14, a notification unit 45 to be described later, and a memory 18 that stores the number of times of puff operations, time of energization to the load 21 and the like. The MCU 50 performs various types of control of the aerosol inhaler 1. Specifically, the MCU 50 mainly includes a processor 55 (see FIG. 7), which will be described below, and further includes storage media, such as a random access memory (RAM) necessary for the processor 55 to operate and a read only memory (ROM) that store various types of information. More specifically, the processor in the present specification is an electric circuit in which circuit elements such as semiconductor elements are combined.

The MCU 50 includes a voltage sensor 16 that measures a power supply voltage of the power supply 12. The voltage sensor 16 may include an operational amplifier 56 and an ADC 57, which will be described later. In the MCU 50, an output signal of the voltage sensor 16 is input to the processor 55. Alternatively, the voltage sensor 16 may be provided outside the MCU 50 and connected to the MCU 50.

The power supply unit case 11 is provided therein with an air intake opening (not shown) for taking in outside air. The air intake opening may be provided around the operation portion 14, or may be provided around the charge terminal 43.

(First Cartridge)

As shown in FIG. 3, inside a cylindrical cartridge case 27, the first cartridge 20 includes: a reservoir 23 that stores an aerosol source 22; the electric load 21 that atomizes the aerosol source 22; a wick 24 that draws the aerosol source from the reservoir 23 to the load 21; an aerosol flow path 25 through which an aerosol generated by atomization of the aerosol source 22 flows toward the second cartridge 30; and an end cap 26 that accommodates a part of the second cartridge 30.

The reservoir 23 is partitioned and formed so as to surround a periphery of the aerosol flow path 25, and stores the aerosol source 22. A porous body, such as a resin web or cotton, may be accommodated in the reservoir 23, and the aerosol source 22 may be impregnated in the porous body. The reservoir 23 may only store the aerosol source 22 without accommodating the porous body of resin web or cotton. The aerosol source 22 includes a liquid, such as glycerin, propylene glycol, or water.

The wick 24 is a liquid holding member that draws the aerosol source 22 from the reservoir 23 to the load 21 by utilizing a capillary phenomenon. The wick 24 is made of, for example, glass fiber or porous ceramic.

The load 21 atomizes the aerosol source 22 by heating the aerosol source 22 without burning using power supplied from the power supply 12 via the discharge terminal 41. The load 21 is formed of an electric heating wire (coil) wound at a predetermined pitch.

The load 21 may be any element that can perform atomization by heating the aerosol source 22 to generate an aerosol. The load 21 is, for example, a heating element. Examples of the heating element include a heating resistor, a ceramic heater, and an induction heating type heater. Hereinafter, an electric resistance value of the load 21 will be referred to as an electric resistance value $R_H$.

As the load 21, a load whose temperature and electric resistance value have a correlation is used. As the load 21, a load having a positive temperature coefficient (PTC) characteristic is used that the electric resistance value increases as the temperature increases. The PTC characteristic is also referred to as a positive resistance-temperature coefficient characteristic.

A coefficient indicating magnitude of a change amount of the electric resistance value of the load 21 with respect to a change amount of the temperature of the load 21 is referred to as a temperature coefficient of resistance α[ppm (parts per million)/° C.). The temperature coefficient of resistance α is expressed by the following Formula (F0) taking the temperature of the load 21 as T, a reference temperature as $T_{REF}$, and a reference electric resistance value as $R_{REF}$.

$$\alpha [\text{ppm}/^\circ \text{C.}] = \frac{R_H - R_{REF}}{R_{REF}} \cdot \frac{1}{T - T_{REF}} \cdot 10^6 \quad \text{(F0)}$$

The aerosol flow path 25 is downstream of the load 21 and is provided on a center line L of the power supply unit 10. The end cap 26 includes a cartridge accommodating portion 26a that accommodates a part of the second cartridge 30, and a communication path 26b through which the aerosol flow path 25 and the cartridge accommodating portion 26a are communicated.

(Second Cartridge)

The second cartridge 30 stores a flavor source 31. The second cartridge 30 is detachably accommodated in the cartridge accommodating portion 26a provided in the end cap 26 of the first cartridge 20. An end portion, which is located on a side opposite to the side of the first cartridge 20, of the second cartridge 30 serves as a user inhale opening 32. The inhale opening 32 is not limited to be formed integrally with the second cartridge 30, and may also be detachable from the second cartridge 30. By configuring the inhale opening 32 separately from the power supply unit 10 and the first cartridge 20 in this way, the inhale opening 32 can be kept hygienic.

The aerosol generated by atomizing the aerosol source 22 with the load 21 passes through the flavor source 31 in the second cartridge 30 and thus is imparted with a flavor. Chopped tobacco or a molded body obtained by molding a tobacco raw material into particles can be used as a raw material piece that forms the flavor source 31. The flavor source 31 may also be formed of a plant other than tobacco (for example, mint, Chinese herb, or herb). The flavor source 31 may be provided with a fragrance such as menthol.

In the aerosol inhaler 1 of the present embodiment, a flavored aerosol can be generated with the aerosol source 22, the flavor source 31, and the load 21. That is, the aerosol source 22 and the flavor source 31 constitute an aerosol generation source that generates the aerosol.

The aerosol generation source of the aerosol inhaler 1 is a portion that is replaced and used by the user. As this portion, for example, one first cartridge 20 and one or a plurality of (for example, five) second cartridges 30 are provided to the user as a set.

In addition to a configuration in which the aerosol source 22 and the flavor source 31 are separated from each other, a configuration in which the aerosol source 22 and the flavor source 31 are integrally formed, a configuration in which the flavor source 31 is omitted and substances that can be contained in the flavor source 31 are added to the aerosol source 22, or a configuration in which a medicine or the like is added to the aerosol source 22 instead of the flavor source 31 may also be employed as the configuration of the aerosol generation source used in the aerosol inhaler 1.

In a case where the aerosol inhaler 1 includes the aerosol generation source in which the aerosol source 22 and the flavor source 31 are integrally formed, for example, one or a plurality of (for example, 20) aerosol generation sources are provided as a set to the user.

In a case where the aerosol inhaler 1 only includes the aerosol source 22 as the aerosol generation source, for example, one or a plurality of (for example, 20) aerosol generation sources are provided as a set to the user.

In the aerosol inhaler 1 configured in this way, as indicated by an arrow B in FIG. 3, air flowing in from the intake opening (not shown) provided in the power supply unit case 11 passes through the vicinity of the load 21 of the first cartridge 20 from the air supply unit 42. The load 21 atomizes the aerosol source 22 drawn from the reservoir 23 by the wick 24. The aerosol generated by atomization flows through the aerosol flow path 25 together with the air flowing in from the intake opening, and is supplied to the second cartridge 30 via the communication path 26b. The aerosol supplied to the second cartridge 30 passes through the flavor source 31 so as to be flavored, and is then supplied to the inhale opening 32.

The aerosol inhaler 1 is provided with the notification unit 45 that notifies various types of information (see FIG. 5). The notification unit 45 may be configured with a light emitting element, a vibrating element, or a sound output element. The notification unit 45 may also be a combination of two or more elements from among the light emitting element, the vibrating element, and the sound output element. The notification unit 45 may be provided in any one of the power supply unit 10, the first cartridge 20, and the second cartridge 30, and is preferably provided in the power supply unit 10. For example, a configuration in which a periphery of the operation portion 14 has a light-transmitting property and light is emitted by a light emitting element such as an LED is employed.

As recommended temperatures at the time of using the aerosol inhaler 1, an operation guarantee temperature range is determined in advance in which a sufficient amount of aerosol can be generated and safety of the power supply 12 can be ensured. The operation guarantee temperature range of the aerosol inhaler 1 is, for example, a range of −10° C. or higher and 45° C. or lower, which includes a normal temperature (specifically, a temperature in a range of 5° C. to 35° C. defined by Japanese Industrial Standards). Further, although details will be described later, an operation guarantee temperature range in which safety of the load 21 can be ensured is determined in advance for the load 21 itself. The operation guarantee temperature range of the load 21 is, for example, a range of −10° C. or higher and 300° C. or lower.

(Electric Circuit)

A main part of an electric circuit of the power supply unit 10 will be described with reference to FIG. 6.

The power supply unit 10 has a main electric circuit configuration, including the power supply 12, the discharge terminal 41 to which the first cartridge 20 including the load 21 is detachable, the MCU 50, a low drop out (LDO) regulator 60, a switch 61, a switch 62, a first element 63 having a first electric resistance value $R_1$, a second element 64 having a second electric resistance value $R_2$ and a third element 65 having a third electric resistance value $R_3$.

Each of the first element 63, the second element 64, and the third element 65 may be an element having an electric resistance value, for example, a resistor, a diode, a transistor, or the like. In the example of FIG. 6, the first element 63, the second element 64, and the third element 65 are resistors, respectively.

The switches 61 and 62 are switching elements such as transistors that switch between cutoff and continuity of a wiring path. In the example of FIG. 6, each of the switches 61 and 62 is an insulated gate bipolar transistor (IGBT) of a normally-off type that is turned on (conducting) upon receiving a high-level on command signal supplied from the MCU 50 and is turned off (cut off) in response to a low-level off command signal supplied from the MCU 50.

The LDO regulator 60 and the MCU 50 are connected in series to the power supply 12. The LDO regulator 60 steps down and outputs a voltage from the power supply 12. An output voltage of the LDO regulator 60 (hereinafter, referred to as a reference voltage $V_{REF}$) is supplied to the MCU 50 as an operation voltage of the MCU 50. For example, the LDO regulator 60 steps down a voltage of 4.2 V from the power supply 12 to 3.7 V and outputs the voltage. That is, the reference voltage $V_{REF}$ is, for example, 3.7 V. Among a main positive bus LU and a main negative bus LD, the main positive bus LU is a line on a high potential side, and the main negative bus line LD is a line on a low potential side. The main positive bus LU may be a line having the highest potential in the electric circuit of the power supply unit 10. The main negative bus LD may be a line having the lowest potential in the electric circuit of the power supply unit 10.

The MCU 50 is connected to the LDO regulator 60 and the main negative bus LD connected to a negative electrode of the power supply 12. The MCU 50 is also connected to the switch 61 and the switch 62, and performs on and off control of the switch 61 and the switch 62.

In a state where the first cartridge 20 is attached to the power supply unit 10, the first element 63 and the load 21 are connected in series to form a first series circuit C1. The second element 64 and the third element 65 are connected in series to form a second series circuit C2. The first series circuit C1 and the second series circuit C2 are connected in parallel between the main positive bus LU and the main negative bus LD.

Each of the first series circuit C1 and the second series circuit C2 is connected to the main positive bus LU and the main negative bus LD. Specifically, a collector of the switch 62 is connected to the main positive bus LU, and the first element 63 and the second element 64 are connected in parallel to an emitter of the switch 62. In addition, the load 21 and the third element 65 are connected in parallel to the main negative bus LD. Further, the load 21 is connected to the first element 63, and the third element 65 is connected to the second element 64.

In this way, the first series circuit C1 has a configuration in which the first element 63 is an element on a high potential side and the load 21 is an element on a low potential side. The second series circuit C2 has a configuration in which the second element 64 is an element on a high potential side and the third element 65 is an element on a low potential side.

The first series circuit C1 is connected to the MCU 50. Specifically, the MCU 50 is connected to the first series circuit C1 between the first element 63 and the load 21.

The second series circuit C2 is connected to the MCU 50. Specifically, the MCU 50 is connected to the second series circuit C2 between the second element 64 and the third element 65.

The switch 61 is connected to the main positive bus LU and the first series circuit C1. Specifically, a collector of the switch 61 is connected to the main positive bus LU. An emitter of the switch 61 is connected to a position on a lower potential side than a node connected to the MCU 50, between the first element 63 and the load 21 in the first series circuit C1.

Figure 6:
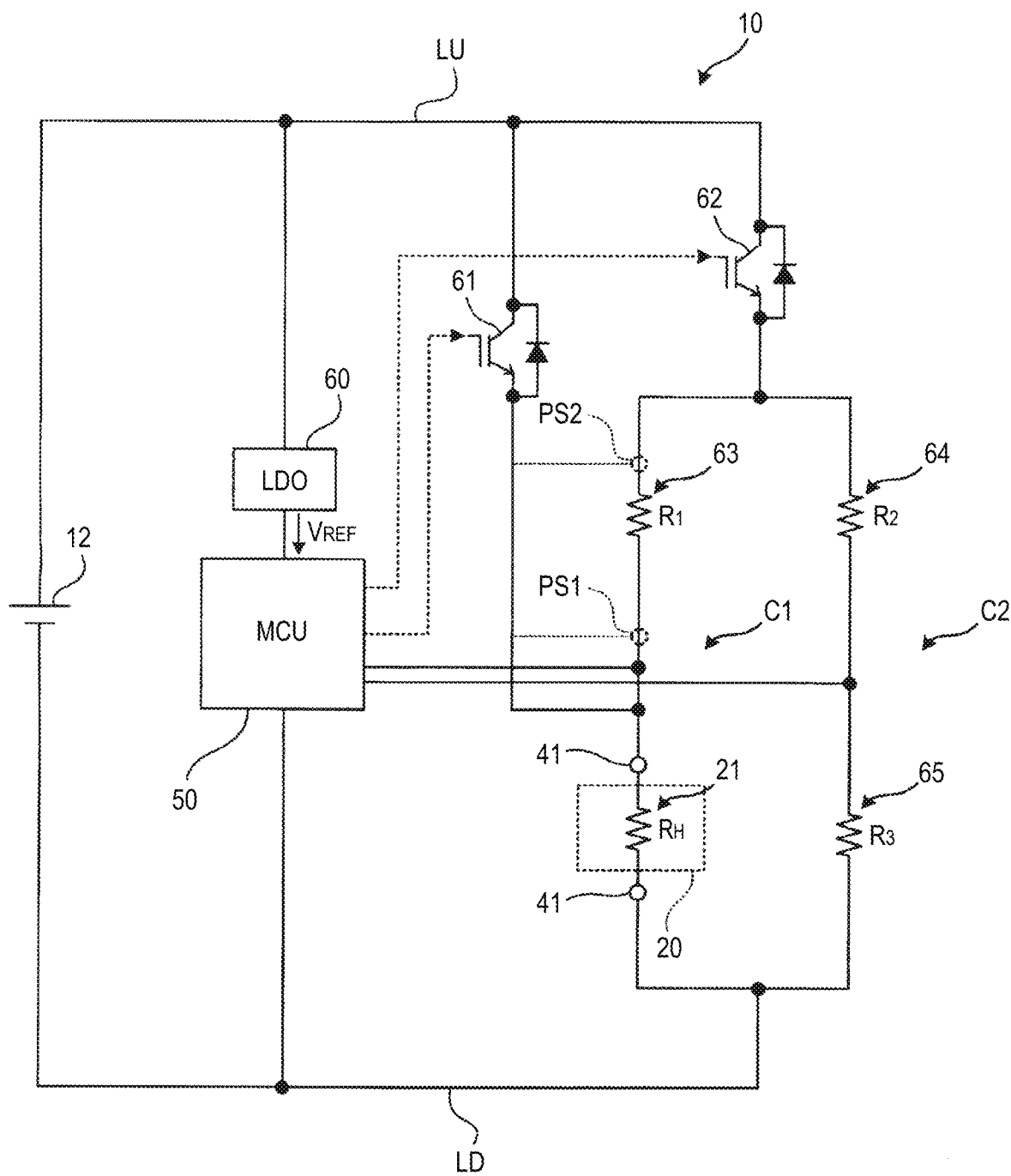
FIG. 6 is a diagram showing a circuit configuration of the power supply unit of the aerosol inhaler shown in FIG. 1.

The emitter of the switch 61 may be connected to a position PS1 on a higher potential side than the connection node with the MCU 50 in the first series circuit C1, as indicated by a broken line in FIG. 6. The emitter of the switch 61 may be connected to a position PS2 on a higher potential side than the first element 63 in the first series circuit C1, as indicated by a broken line in FIG. 6.

In the power supply unit 10 shown in FIG. 6, a circuit including the switch 61 and a wiring, which is connected between the main positive bus LU and the first element 63 and the load 21 of the first series circuit C1, is hereinafter referred to as a heating circuit. Further, a circuit including the switch 62 and a wiring, which connects the first series circuit C1 and the second series circuit C2 to the main positive bus LU, is hereinafter referred to as a first connection circuit. Further, a circuit including a wiring, which connects the first series circuit C1 and the second series circuit C2 to the main negative bus LD, is hereinafter referred to as a second connection circuit.

(MCU)

Next, a configuration of the MCU 50 will be described in more detail.

As shown in FIG. 5, the MCU 50 includes an aerosol generation request detector 51, a temperature detector 52, a power controller 53, and a notification controller 54, as functional blocks implemented by the processor executing a program stored in the ROM (not shown).

The aerosol generation request detector 51 detects an aerosol generation request based on an output result of the intake sensor 15. The intake sensor 15 is configured to output a value of a pressure (internal pressure) change in the power supply unit 10 caused by inhale of the user through the inhale opening 32. The intake sensor 15 is, for example, a pressure sensor that outputs an output value (for example, a voltage value or a current value) corresponding to an internal pressure that changes in accordance with a flow rate of air inhaled from the intake opening (not shown) toward the inhale opening 32 (that is, the puff operation of the user). The intake sensor 15 may be configured with a condenser microphone or the like. The intake sensor 15 may output an analog value, or may output a digital value converted from the analog value.

Although details will be described later, the temperature detector 52 detects the temperature of the load 21 based on an output signal of the first series circuit C1 and an output signal of the second series circuit C2 shown in FIG. 6. When the switch 62 is turned on and the switch 61 is turned off, currents flow in the first series circuit C1 and the second series circuit C2 respectively, and the temperature detector 52 detects the temperature of the load 21 based on the output signal of the first series circuit C1 and the output signal of the second series circuit C2 at this time.

The notification controller 54 controls the notification unit 45 to notify various types of information. For example, the notification controller 54 controls the notification unit 45 to notify a replacement timing of the second cartridge 30 in response to detection of the replacement timing of the second cartridge 30. The notification controller 54 detects and notifies the replacement timing of the second cartridge 30 based on the cumulative number of times of puff operations or cumulative time of energization to the load 21 that is stored in the memory 18. The notification controller 54 is not limited to only notify the replacement timing of the second cartridge 30, and may also notify a replacement timing of the first cartridge 20, a replacement timing of the power supply 12, a charging timing of the power supply 12 and the like.

In a state where one unused second cartridge 30 is set, when the puff operation is performed a predetermined number of times or when the cumulative time of energization to the load 21 reaches a predetermined value (for example, 120 seconds) due to the puff operation, the notification controller 54 determines that the second cartridge 30 has been used up (that is, a remaining amount is zero or empty), and notifies the replacement timing of the second cartridge 30.

Further, when it is determined that all the second cartridges 30 included in the set have been used up, the notification controller 54 may determine that one first cartridge 20 included in the set has been used up (that is, the remaining amount is zero or empty) and notify the replacement timing of the first cartridge 20.

When the aerosol generation request detector 51 detects an aerosol generation request, the power controller 53 controls discharge of the power supply 12 via the discharge terminal 41 by turning on/off the switches 61 and 62. The power controller 53 turns off the switch 62 and turns on the switch 61 to cause a large current to flow to the load 21, and electricity discharge to the load 21 is performed. When the electricity discharge to the load 21 is performed in this way, a larger current flows through the load 21 than that following through the first element 63 in the first series circuit C1. As will be described later, since the first element 63, the second element 64, and the third element 65 have a sufficiently large battery resistance value compared with that of the load 21, the current flowing through the first element 63 is zero or almost zero, and the current flows only through the load 21. Since the current flowing through the first element 63 is zero or almost zero, a larger current can flow from the power supply 12 to the load 21, and thus generation efficiency of aerosol is improved.

Even in a configuration in which the emitter of the switch 61 is connected to the position PS1 in FIG. 6, when the electricity discharge to the load 21 is performed, similarly, a large current can flow through the load 21 than through the first element 63 in the first series circuit C1. In a configuration in which the emitter of the switch 61 is connected to the position PS2 in FIG. 6, when the electricity discharge to the load 21 is performed, the current also flows through the first element 63 in the first series circuit C1. However, as will be described later, since an electric resistance value of the second series circuit C2 is larger than the electric resistance value of the load 21, a larger current can flow through the load 21. In either case, when the electricity discharge to the load 21 is performed, a large current can flow through the load 21, and the load 21 can be efficiently heated.

(Configuration for Temperature Detection of Load)

Figure 7:
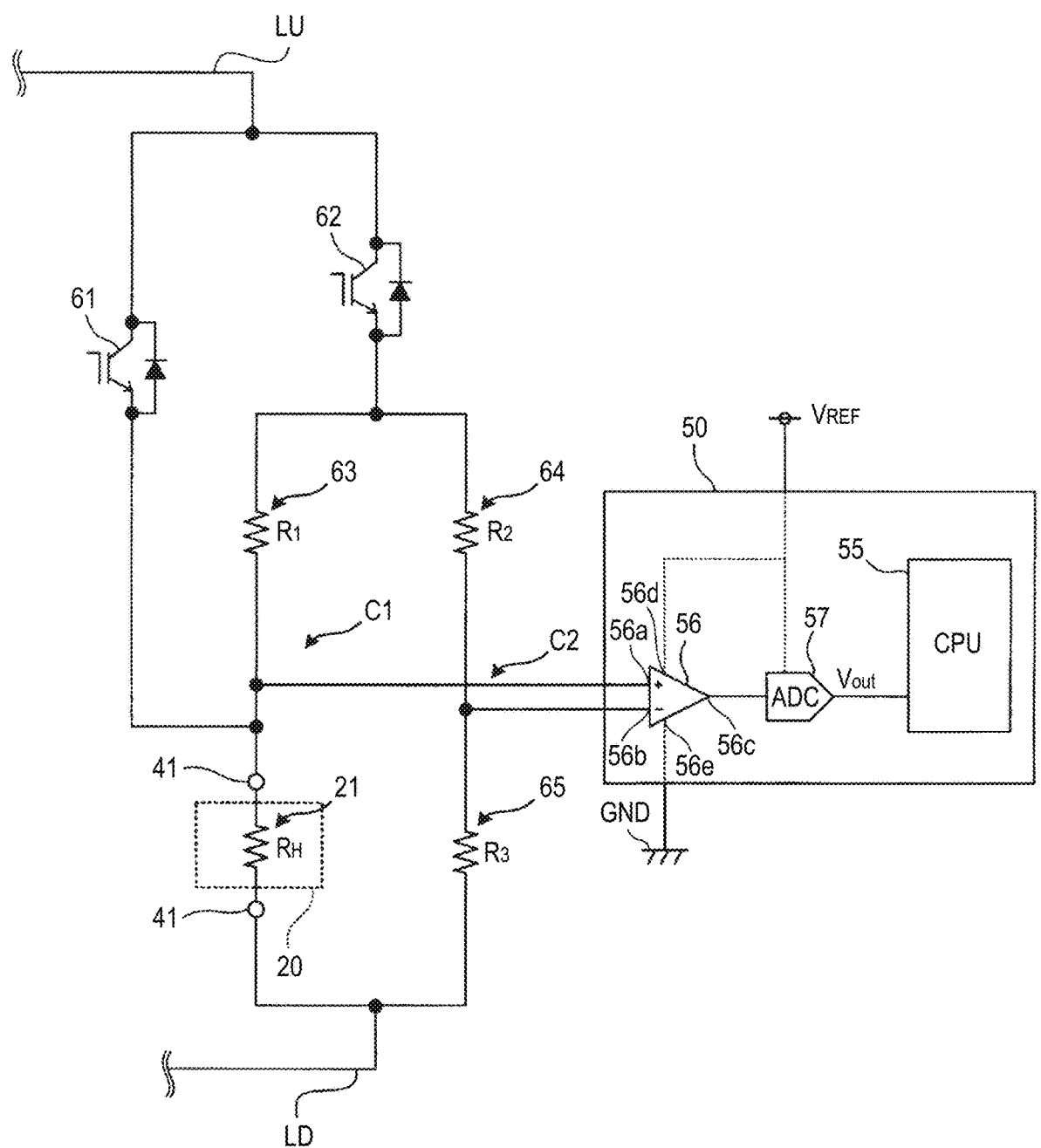
FIG. 7 is an enlarged view of a main part of the circuit configuration of the power supply unit shown in FIG. 6.

FIG. 7 is an enlarged view of a main part of the circuit configuration of the power supply unit 10 shown in FIG. 6. As shown in FIG. 7, the MCU 50 includes the operational amplifier 56, the analog-to-digital converter (ADC) 57, and the processor 55. Although an example in which the operational amplifier 56 and the ADC 57 are provided inside the MCU 50 will be described here, the operational amplifier 56 and the ADC 57 may be provided outside the MCU 50.

The operational amplifier 56 includes a non-inverting input terminal (that is, a + side input terminal) 56a, an inverting input terminal (that is, a − side input terminal) 56b, and an output terminal 56c. Then, the operational amplifier 56 outputs, from the output terminal 56c, an output signal obtained by amplifying a difference value, which is obtained by subtracting a voltage input to the inverting input terminal 56b from a voltage input to the non-inverting input terminal 56a, with a predetermined amplification factor A.

The value obtained by the operational amplifier 56 by subtracting the voltage input to the inverting input terminal 56b from the voltage input to the non-inverting input terminal 56a is hereinafter also referred to as a differential input. The differential input is equal to the difference value, which is obtained by subtracting the voltage input to the inverting input terminal 56b from the voltage input to the non-inverting input terminal 56a, unless sticking of the differential input occurs which will be described later. When the electric resistance value of the load 21 varies with its temperature, the differential input changes. Similarly, when the electric resistance value of the load 21 varies with its temperature, the output signal of the operational amplifier 56 changes.

The operational amplifier 56 has a pair of power supply terminals including a positive power supply terminal 56d and a negative power supply terminal 56e. The positive power supply terminal 56d is a power supply terminal on a high potential side, and is connected to the reference voltage $V_{REF}$ as shown in FIG. 7, for example. That is, potential of the positive power supply terminal 56d (hereinafter, also referred to as voltage of the positive power supply terminal 56d) is equal to the reference voltage $V_{REF}$, and is 3.7 V, for example. Hereinafter, the potential of the positive power supply terminal 56d is also referred to as a voltage of the positive power supply terminal 56d.

On the other hand, the negative power supply terminal 56e is a power supply terminal on a low potential side, and is connected to the ground GND as shown in FIG. 7, for example. That is, potential of the negative power supply terminal 56e (hereinafter, also referred to as voltage of the negative power supply terminal 56e) is equal to potential of the ground GND (hereinafter, also referred to as voltage of the ground GND) and is 0 V.

In a case where an input/output rail-to-rail type operational amplifier is used as the operational amplifier 56, when the voltage of the positive power supply terminal 56d is set to the reference voltage $V_{REF}$ and the voltage of the negative power supply terminal 56e is set to 0 V, the value of the differential input and potential of the output signal (hereinafter, also referred to as voltage of the output signal), of the operational amplifier 56, can take values from 0 V to the reference voltage $V_{REF}$. In other words, in this case, a minimum value of the value that can be obtained as the differential input of the operational amplifier 56 or of the voltage that can be output as the output signal thereof is 0 V. A maximum value of the value that can be obtained as the differential input of the operational amplifier 56 or of the voltage that can be output as the output signal thereof is the reference voltage $V_{REF}$. In the following description, unless otherwise specified, the operational amplifier 56 is treated as an input/output rail-to-rail type operational amplifier.

An operational amplifier that is not an input/output rail-to-rail type (hereinafter also referred to as a non-input/output rail-to-rail type operational amplifier) may be used as the operational amplifier 56. In a case where a non-input/output rail-to-rail type operational amplifier is used as the operational amplifier 56, a range for obtaining the value of the differential input and the potential of the output signal for the operational amplifier 56 is narrower than in the case where the input/output rail-to-rail type operational amplifier 56 is used. That is, in this case, the minimum value of the value that can be obtained as the differential input of the operational amplifier 56 or of the voltage that can be output as the output signal thereof is larger than 0 V. The maximum value of the value that can be obtained as the differential input of the operational amplifier 56 or of the voltage that can be output as the output signal thereof is smaller than the reference voltage $V_{REF}$. In the following description, in the case where a non-input/output rail-to-rail type operational amplifier is used as the operational amplifier 56, the minimum value and the maximum value of the value that can be obtained as the differential input of the operational amplifier 56 or of the voltage that can be output as the output signal thereof are also referred to as a minimum value and a maximum value that can be handled by the operational amplifier 56. The minimum value that can be handled by the operational amplifier 56 can also be referred to as a minimum value that can be obtained by the operational amplifier 56. That is, the minimum value that can be handled by the operational amplifier 56 is an example of the minimum value that can be obtained by the operational amplifier in the present invention. Similarly, the maximum value that can be handled by the operational amplifier 56 can be referred to as a maximum value that can be obtained by the operational amplifier 56.

For example, in the input/output rail-to-rail type operational amplifier 56, when the difference value between the voltage input to the non-inverting input terminal 56a of the operational amplifier 56 and the voltage input to the inverting input terminal 56b, and the value obtained by multiplying the differential input of the operational amplifier 56 by the amplification factor A are larger than the reference voltage $V_{REF}$, the value obtained as the differential input of the operational amplifier 56 or the voltage output as the output signal thereof sticks to the reference voltage $V_{REF}$. In the input/output rail-to-rail type operational amplifier 56, when the difference value between the voltage input to the non-inverting input terminal 56a of the operational amplifier 56 and the voltage input to the inverting input terminal 56b, and the value obtained by multiplying the differential input of the operational amplifier 56 by the amplification factor A are smaller than 0 V, the value obtained as the differential input of the operational amplifier 56 or the voltage output as the output signal thereof sticks to 0 V.

In the non-input/output rail-to-rail type operational amplifier 56, when the difference value between the voltage input to the non-inverting input terminal 56a of the operational amplifier 56 and the voltage input to the inverting input terminal 56b, and the value obtained by multiplying the differential input of the operational amplifier 56 by the amplification factor A are larger than the maximum value that can be handled by the operational amplifier 56, the value obtained as the differential input of the operational amplifier 56 or the voltage output as the output signal thereof sticks to the maximum value that can be handled by the operational amplifier 56. In the non-input/output rail-to-rail type operational amplifier 56, when the difference value between the voltage input to the non-inverting input terminal 56a of the operational amplifier 56 and the voltage input to the inverting input terminal 56b, and the value obtained by multiplying the differential input of the operational amplifier 56 by the amplification factor A are smaller than the minimum value that can be handled by the operational amplifier 56, the value obtained as the differential input of the operational amplifier 56 or the voltage output as the output signal thereof sticks to the minimum value that can be handled by the operational amplifier 56.

Hereinafter, the voltage output as the output signal of the operational amplifier 56 continuously sticking to the reference voltage $V_{REF}$ or 0 V (in the case of the non-input/output rail-to-rail type, sticking to the maximum value or the minimum value that can be handled by the operational amplifier 56) regardless of the temperature of the load 21 as described is also referred to as sticking of the output signal. Similarly, the value that can be obtained as the differential input of the operational amplifier 56 continuously sticking to the reference voltage $V_{REF}$ or 0 V (in the case of the non-input/output rail-to-rail type, sticking to the maximum value or the minimum value that can be handled by the operational amplifier 56) regardless of the temperature of the load 21 as described is also referred to as sticking of the differential input.

When sticking of the differential input of the operational amplifier 56 or sticking of the output signal thereof occurs, it is difficult to detect (uniquely specify) a temperature T of the load 21 based on the output signal of the operational amplifier 56. For this reason, as will be described in detail later, in the aerosol inhaler 1 of the present embodiment, the sticking of the differential input of the operational amplifier 56 or the sticking of the output signal thereof does not occur in an important temperature range for managing the temperature of the load 21.

Further, the first series circuit C1 is connected to the non-inverting input terminal 56a of the operational amplifier 56. Specifically, the non-inverting input terminal 56a of the operational amplifier 56 is connected between the first element 63 and the load 21 in the first series circuit C1, on a higher potential side than the connection node of the first series circuit C1 with the switch 61.

Meanwhile, the second series circuit C2 is connected to the inverting input terminal 56b of the operational amplifier 56. Specifically, the inverting input terminal 56b of the operational amplifier 56 is connected between the second element 64 and the third element 65 in the second series circuit C2.

The ADC 57 converts the output signal of the operational amplifier 56 into a digital signal and outputs the digital signal. As the ADC 57, one having a resolution of N bits that operates with the reference voltage $V_{REF}$ is used.

In a state where the switch 62 is turned off and the switch 61 is turned on, a voltage $V_+$ input to the non-inverting input terminal 56a of the operational amplifier 56 and a voltage $V_-$ input to the inverting input terminal 56b of the operational amplifier 56 are expressed by the following Formulas (F1) and (F2) respectively, with a voltage (in other words, a potential difference between the main positive bus LU and the main negative bus LD) applied to an entire parallel circuit formed of the first series circuit C1 and the second series circuit C2 being taken as "V".

$$V_+ = \frac{R_H}{R_1 + R_H} \cdot V \quad (F1)$$

$$V_- = \frac{R_3}{R_2 + R_3} \cdot V \quad (F2)$$

Accordingly, in the state where the switch 62 is turned off and the switch 61 is turned on, an output signal output from the output terminal 56c of the operational amplifier 56 is expressed by the following Formula (F3) based on the amplification factor A and Formulas (F1) and (F2). Apart of Formula (F3) excluding the amplification factor A indicates a differential input that is a difference value between a signal input to the non-inverting input terminal 56a of the operational amplifier 56 and a signal input to the inverting input terminal 56b thereof. Hereinafter, this differential input is also referred to as $V_{IN}$. The differential input $V_{IN}$ changes in response to a change in the electric resistance value $R_H$ of the load 21. Hereinafter, a change amount of the differential input $V_{IN}$ with respect to a change amount of the electric resistance value $R_H$ of the load 21 will be referred to as $\Delta V_{IN}$. It is sufficient that the amplification factor A is a natural number of 1 or more.

$$A \times (V_+ - V_-) = A \cdot \frac{R_H}{R_1 + R_H} \cdot V - A \cdot \frac{R_3}{R_2 + R_3} \cdot V \quad (F3)$$

$$= A \cdot \frac{R_H \cdot (R_2 + R_3) - R_3 \cdot (R_1 + R_H)}{(R_1 + R_H) \cdot (R_2 + R_3)} \cdot V$$

$$= A \cdot \frac{R_H \cdot R_2 - R_1 \cdot R_3}{(R_1 + R_H) \cdot (R_2 + R_3)} \cdot V$$

The temperature detector 52, which is a functional block of the processor 55, acquires an output signal of the operational amplifier 56 in the state where the switch 62 is turned off and the switch 61 is turned on. In Formula (F3), values other than that of the electric resistance value $R_H$ of the load 21 are known values. Accordingly, the temperature detector 52 can derive the electric resistance value $R_H$ of the load 21 based on the acquired output signal of the operational amplifier 56 and Formula (F3). The temperature detector 52 detects the temperature T of the load 21 based on the electric resistance value $R_H$ of the load 21 derived as described above, and information on the PTC characteristic of the load 21 stored in advance in a ROM or the like (not shown) (for example, information on a reference temperature $T_{REF}$, a reference electric resistance value $R_{REF}$ corresponding to the reference temperature $T_{REF}$, and the temperature coefficient of resistance α [ppm/° C.]).

Here, a detection resolution of the temperature T of the load 21 by the temperature detector 52 will be considered.

A resolution Res [V/bit] by the N-bit ADC 57 to which the reference voltage $V_{REF}$ is input as a power supply is represented by the following Formula (F4).

$$Res[\text{V/bit}] = \frac{V_{REF}}{2^N} \quad (F4)$$

When Formula (F4) is rewritten, a temperature resolution Res [° C.] is represented by the following Formula (F5). $\Delta T_H (\Delta R_H)$ in Formula (F5) indicates a change amount of the temperature T of the load 21 in accordance with the change amount of the electric resistance value $R_H$ of the load 21. Accordingly, Formula (F5) can be modified as in Formula (F6) by using the temperature coefficient of resistance α [%] of the load 21. Note that in deriving Formula (F6), the temperature coefficient of resistance α [ppm/° C.] is multiplied by $10^2$ and $10^{-6}$ in order to convert a unit of the temperature coefficient of resistance a from [ppm/° C.] to [%].

$$Res[° \text{C.}] = \frac{\Delta T_H(\Delta R_H) \cdot Res[\text{V/bit}]}{\Delta V_{IN}} \quad (F5)$$

$$Res[° \text{C.}] = \frac{1}{\alpha[\%]} \cdot \frac{1}{\Delta V_{IN}} \cdot Res[\text{V/bit}] \quad (F6)$$

$$= \frac{1}{\alpha[\text{ppm}/° \text{C.}] \times 10^2 \times 10^{-6}} \cdot \frac{1}{\Delta V_{IN}} \cdot Res[\text{V/bit}]$$

$$= \frac{1}{\alpha[\text{ppm}/° \text{C.}] \times 10^{-4}} \cdot \frac{1}{\Delta V_{IN}} \cdot \frac{V_{REF}}{2^N}$$

As can be seen from Formula (F6), in order to increase the detection resolution of the temperature T of the load 21 by the temperature detector 52, the change amount $\Delta V_{IN}$ of the differential input $V_{IN}$ of the operational amplifier 56 may be increased.

In the power supply unit 10 of the present embodiment, as can be seen from Formula (F3), magnitude of the signal input to the non-inverting input terminal 56a of the operational amplifier 56 and magnitude of the signal input to the inverting input terminal 56b are significantly smaller than in a case where the inverting input terminal is connected to the ground. That is, the change amount of the differential input $V_{IN}$ of the operational amplifier 56 is smaller than the change amount of the electric resistance value $R_H$ of the load 21. On the other hand, the output signal of the operational amplifier 56 is input to the ADC 57, and the ADC 57 operates with the reference voltage $V_{REF}$. Therefore, the output signal of the operational amplifier 56 (the input signal to the ADC 57) is preferably equal to or lower than the reference voltage $V_{REF}$ in order for the ADC 57 to operate normally.

In the power supply unit 10 of the present embodiment, the differential input $V_{IN}$ of the operational amplifier 56 can be set to a small value. Therefore, the amplification factor A can be set to a large value within a range in which the output signal of the operational amplifier 56 does not exceed the reference voltage $V_{REF}$. As a result, a multiplication value of the amplification factor A and the differential input $V_{IN}$ can be set to a large value, and the detection resolution of the temperature T can be improved.

(Preferred Conditions of Electric Resistance Values of Load, First Element, Second Element, and Third Element)

When detecting the temperature of the load 21, a current based on a voltage V flows through a bridge circuit including the first series circuit C1 and the second series circuit C2, and the bridge circuit itself serves as a heat source. Therefore, in order to prevent Joule heat generated by the current flowing through the first series circuit C1 and the second series circuit C2 from affecting the temperature of the load 21, it is desirable to sufficiently increase an electric resistance value (combined resistance value) of the entire bridge circuit including the first series circuit C1 and the second series circuit C2.

On the other hand, when the electric resistance value $R_H$ of the load 21 is set to a large value, power energy required to increase the temperature of the load 21 to a desired temperature increases. When the power energy is reduced, it takes more time to increase the temperature of the load 21 to a desired temperature. Therefore, it is desirable that the electric resistance value $R_H$ of the load 21 be as small as possible in order to increase aerosol generation efficiency.

In order to increase the aerosol generation efficiency, the power supply unit 10 according to the present embodiment is configured to satisfy a resistance value condition that each of the first electric resistance value $R_1$ of the first element 63, the second electric resistance value $R_2$ of the second element 64, and the third electric resistance value $R_3$ of the third element 65 is larger than the electric resistance value $R_H$ of the load 21.

However, the electric resistance value $R_H$ is a value that changes with the temperature of the load 21. Therefore, it is configured such that the above resistance value condition is satisfied regardless of the temperature of the load 21 in the normal temperature range. As another embodiment, the electric resistance value $R_H$ may be configured such that the above resistance value condition is satisfied only when the load 21 is in a part of the normal temperature range. Specifically, the electric resistance value $R_H$ may be configured such that the above resistance value condition is satisfied when the load 21 is in the above temperature range, the above temperature range and the above first temperature, and the above temperature range and the above second temperature. With such a configuration, a range of options for the load 21 and other elements can be widened.

As described above, in order to accurately acquire the electric resistance value and the temperature of the load 21, the voltage $V_+$ input to the non-inverting input terminal of the operational amplifier 56 is required to be prevented from being lower than the voltage V input to the inverting input terminal. Considering that the electric resistance value $R_H$ is minimum in Formula (F3), the second electric resistance value $R_2$ is required to be larger than the third electric resistance value $R_3$. That is, in the power supply unit 10, the first electric resistance value $R_1$ is larger than the electric resistance value $R_H$, and the second electric resistance value $R_2$ is larger than the third electric resistance value $R_3$.

Here, a value obtained by dividing the first electric resistance value $R_1$ of the first element 63, which is the element on the high potential side in the first series circuit C1, by the electric resistance value $R_H$ of the load 21, which is the element on the low potential side in the first series circuit C1, is set to "n". A value obtained by dividing the second electric resistance value $R_2$ of the second element 64, which is the element on the high potential side in the second series circuit C2, by the third electric resistance value $R_3$ of the third element 65, which is the element on the low potential side in the second series circuit C2, is set to "m". In the power supply unit 10, since the first electric resistance value $R_1$ is larger than the electric resistance value $R_H$ and the second electric resistance value $R_2$ is larger than the third electric resistance value $R_3$, n and m are both real numbers of 1 or larger. In the present embodiment, m constitutes a first resistance ratio and n constitutes a second resistance ratio.

When n and m are defined as described above, "$R_1$" in Formula (F3) is "$n \cdot R_H$", and "$R_2$" is "$m \cdot R_3$". Therefore, Formula (F3) can be modified as in the following Formula (F7).

$$\begin{aligned} A \times (V_+ - V_-) &= A \cdot \frac{R_H \cdot m \cdot R_3 - n \cdot R_H \cdot R_3}{(n \cdot R_H + R_H) \cdot (m \cdot R_3 + R_3)} \cdot V \\ &= A \cdot \frac{R_H \cdot m \cdot R_3 - n \cdot R_H \cdot R_3}{(n+1) \cdot R_H \cdot (m+1) \cdot R_3} \cdot V \\ &= A \cdot \frac{m-n}{(n+1) \cdot (m+1)} \cdot V \end{aligned} \quad \text{(F7)}$$

It can be seen that since a product of n and m in a denominator is strong in Formula (F7), as n and m increase, in other words, as the $R_1$ and $R_2$ on the high potential side are larger than the $R_H$ and $R_3$ on the low potential side, the differential input $V_{IN}$ of the operational amplifier 56 can be reduced, and accordingly the amplification factor A can be increased.

It can be seen from Formula (F7) that by configuring to satisfy a condition of m>n, the voltage $V_+$ input to the non-inverting input terminal 56*a* is not lower than the voltage $V_-$ input to the inverting input terminal 56*b* and the operational amplifier 56 is stably operated, so that temperature detection accuracy of the load 21 can be ensured. The power supply unit 10 according to the present embodiment is configured to satisfy the condition of m>n regardless of the temperature of the load 21 in the normal temperature range. With this configuration, the temperature of the load 21 can be detected with high accuracy regardless of the temperature of the load 21. As another embodiment, the power supply unit 10 may be configured such that the condition of m>n is satisfied only when the load 21 is in a part of the normal temperature range. Specifically, the power supply unit 10 may be configured such that the condition of m>n is satisfied when the load 21 is in the above temperature range, the above temperature range and the above first temperature, and the above temperature range and the above second temperature. With such a configuration, a range of options for the load 21 and other elements can be widened.

(Operation Overview of Aerosol Inhaler)

An operation overview of the aerosol inhaler 1 configured as described above will be described with reference to FIG. 6. Upon detecting an aerosol generation request, the processor 55 of the MCU 50 sends an on command to the switch 61, and sends an off command to the switch 62. When the switch 61 is turned on and the switch 62 is turned off in response to these commands, a large current flows through the heating circuit to the load 21, and the current flowing through the first element 63, the second element 64, and the third element 65 is zero or nearly zero. Accordingly, the load 21 is heated to generate an aerosol.

After elapse of a predetermined time from the start of heating of the load 21, the processor 55 sends an off command to the switch 61, and sends an on command to the switch 62. When the switch 61 is turned off and the switch 62 is turned on in response to these commands, a current flows through the first connection circuit to the first series circuit C1 and the second series circuit C2. A difference value (differential input $V_{IN}$) between output signals of the first series circuit C1 and the second series circuit C2 is amplified by the operational amplifier 56, subjected to digital conversion by the ADC 57, and input to the processor 55. The processor 55 detects a temperature of the load 21 based on the input signal from the ADC 57.

After detecting the temperature of the load 21, the processor 55 sends an on command to the switch 61, and sends an off command to the switch 62 to start generating the aerosol again. By repeating the above operations, the temperature of the load 21 is detected at a high frequency during an aerosol generation period corresponding to the aerosol generation request.

(Example of Specific Operations of Aerosol Inhaler)

Next, an example of specific operations of the aerosol inhaler 1 of the present embodiment will be described with reference to FIG. 8. The aerosol inhaler 1 repeatedly performs the operations shown in FIG. 8 during the aerosol generation period, for example.

Figure 8:
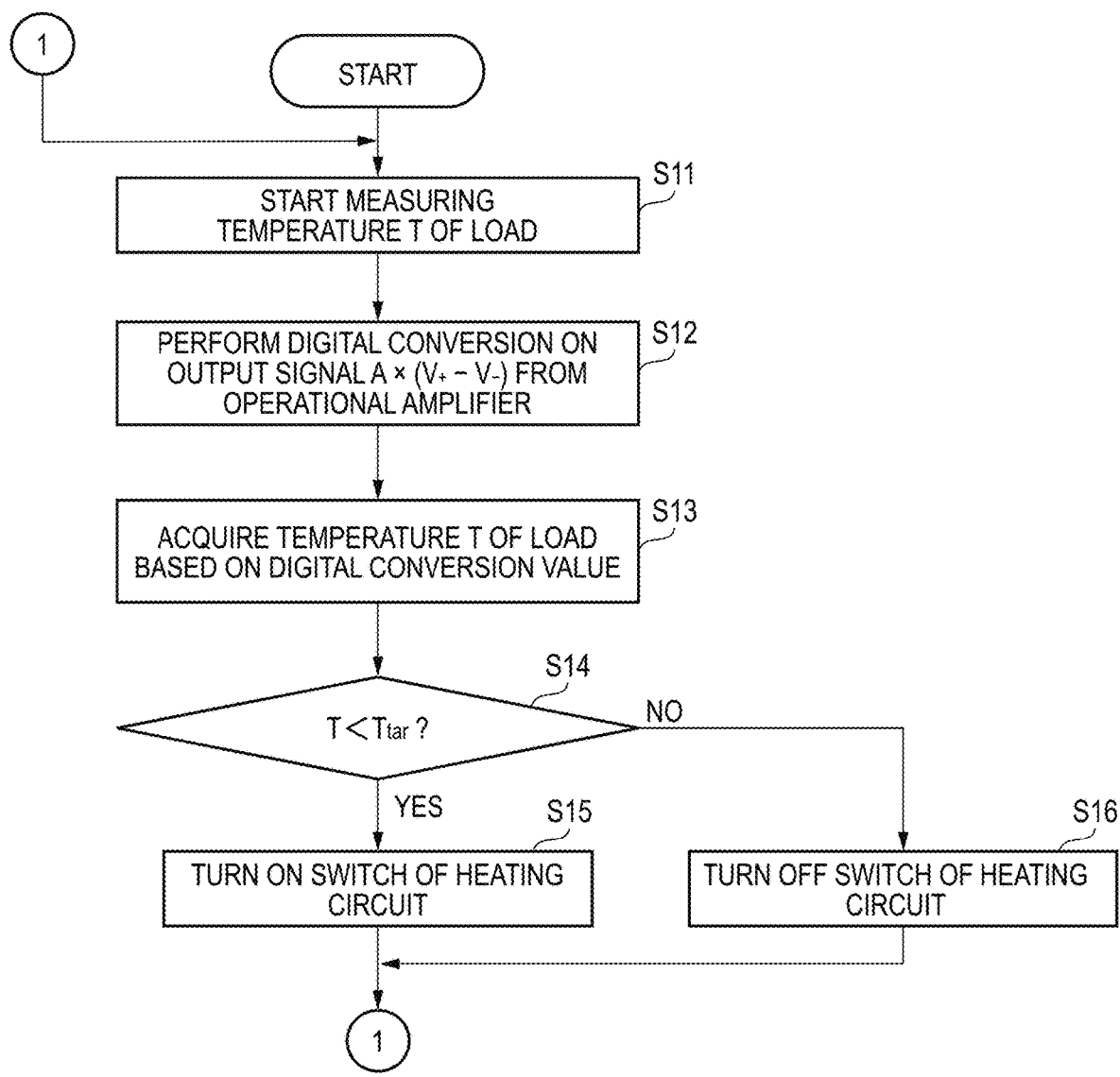
FIG. 8 is a flowchart showing an example of operations of the aerosol inhaler shown in FIG. 1.

As shown in FIG. 8, in the aerosol inhaler 1 of the present embodiment, the processor 55 of the MCU 50 starts to measure the temperature T of the load 21, for example, when it is the timing of detecting the temperature T of the load 21 (step S11). In step S11, the processor 55 sends an off command to the switch 61 and sends an on command to the switch 62, for example. Accordingly, a current flows through the first series circuit C1 and the second series circuit C2 downstream of the switch 62, and the above voltage $V_+$ is input to the non-inverting input terminal 56a of the operational amplifier 56, and the above voltage $V_-$ is input to the inverting input terminal 56b. Therefore, $A \times (V_+ - V_-)$, that is, $A \times V_{IN}$ is output from the operational amplifier 56 as an output signal, and the output signal is input to the ADC 57.

The ADC 57 performs digital conversion on the input $A \times (V_+ - V_-)$ (step S12), and outputs the obtained digital conversion value to the processor 55. The processor 55 acquires the temperature T of the load 21 as described above, based on the digital conversion value received from the ADC 57 (that is, the digital conversion value of the output signal of the operational amplifier 56) (step S13). The processor 55 preferably sends an off command to the switch 62 when the temperature T of the load 21 is acquired, for example. In this way, when the switch 61 is turned on thereafter (see, for example, step S15 to be described later), the current flowing through the heating circuit to the load 21 can be increased.

Next, the processor 55 determines whether the temperature T of the load 21 is lower than a predetermined target temperature $T_{tar}$ (that is, $T < T_{tar}$) based on the acquired temperature T of the load 21 and the target temperature $T_{tar}$ (step S14). The target temperature $T_{tar}$ is, for example, a temperature predetermined by a manufacturer of the aerosol inhaler 1 as a control target value in heating the load 21. Information on the target temperature $T_{tar}$ is stored in advance in a ROM or the like (not shown).

When it is determined that the temperature T of the load 21 is lower than the target temperature $T_{tar}$ (step S14: YES), the processor 55 sends an on command to the switch 61 to turn on the switch 61 (step S15). Accordingly, a current flows through the heating circuit to the load 21, and the load 21 is heated. On the other hand, when it is determined that the temperature T of the load 21 is equal to or higher than the target temperature $T_{tar}$ (step S14: NO), the processor 55 sends an off command to the switch 61 to turn off the switch 61 (step S16). Accordingly, supply of current to the load 21 by the heating circuit is stopped, and heating of the load 21 is stopped. After executing step S15 or step S16, the processor 55 returns the processing to step S11.

As described above, by repeating the processing in which the switch 61 is turned on to heat the load 21 when the temperature T of the load 21 is lower than the target temperature $T_{tar}$, and the switch 61 is turned off to stop heating the load 21 when the temperature T of the load 21 is equal to or higher than the target temperature $T_{tar}$, the temperature T of the load 21 can be controlled so as to be restricted to the target temperature $T_{tar}$.

When the control of restricting the temperature T of the load 21 to the target temperature $T_{tar}$ is performed by turning on or off the switch 61 based on a comparison result between the temperature T of the load 21 and the target temperature $T_{tar}$, if the temperature T of the load 21 can be detected around the target temperature $T_{tar}$, the temperature T of the load 21 can be restricted to the target temperature $T_{tar}$.

Therefore, when the control of restricting the temperature T of the load 21 to the target temperature $T_{tar}$ is performed based on the comparison result between the temperature T of the load 21 and the target temperature $T_{tar}$, there is little need to be able to detect the temperature T of the load 21 in a wide temperature range including temperatures far from the target temperature $T_{tar}$, and more importantly, it is desired to be able to accurately detect the temperature T of the load 21 around the target temperature $T_{tar}$. Therefore, in the present embodiment, to be able to accurately detect the temperature T of the load 21 in an appropriate temperature range is considered.

(Temperatures)

Figure 9:
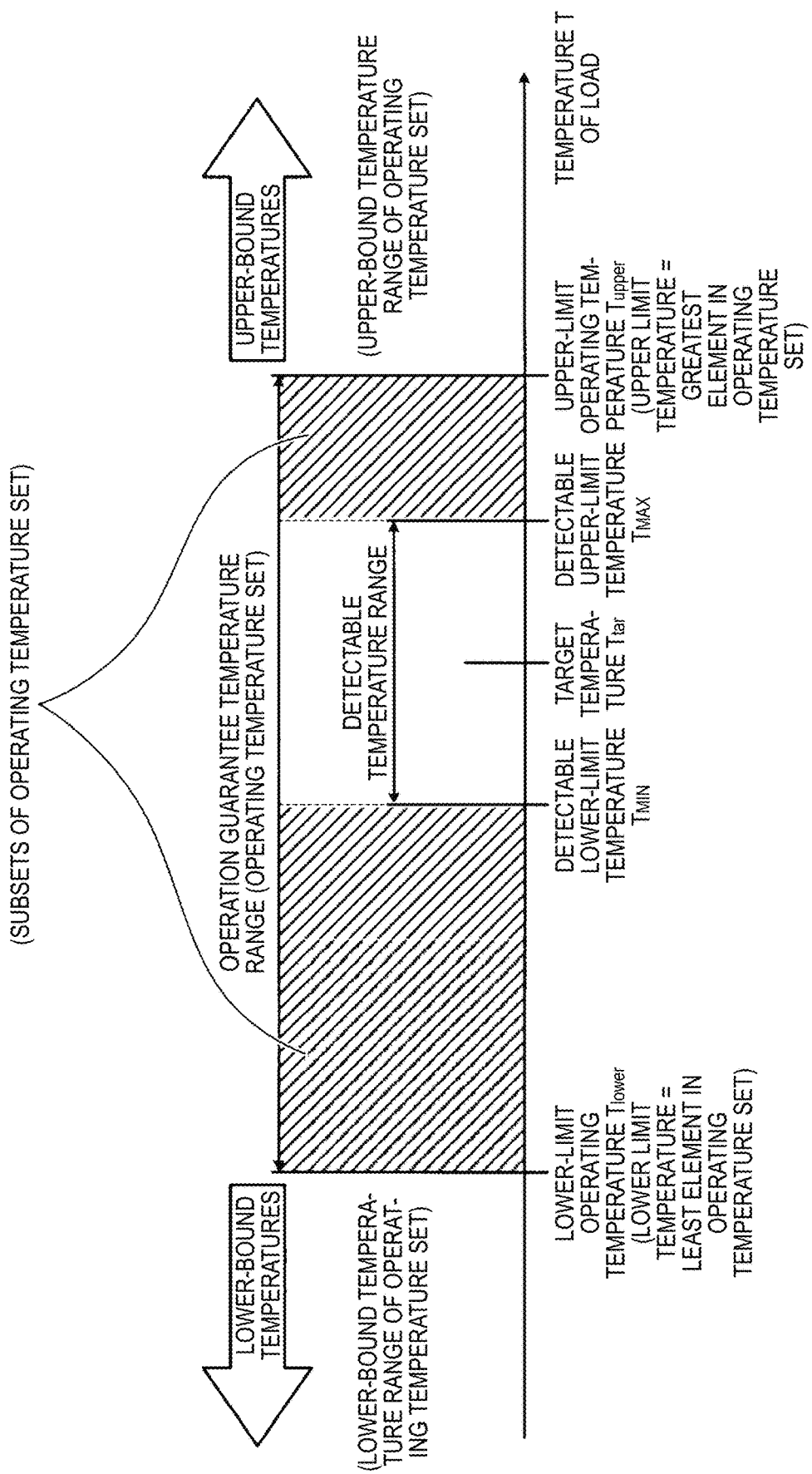
FIG. 9 is a graph showing temperatures related to loads of the aerosol inhaler shown in FIG. 1.

First, temperatures related to the load 21 and used in the following description will be described with reference to FIG. 9. In FIG. 9, a horizontal axis indicates the temperature of the load 21.

As described above, an operation guarantee temperature range in which safety of the load 21 and the aerosol inhaler 1 can be ensured is predetermined for the load 21. As shown in FIG. 9, the operation guarantee temperature range of the load 21 is an example of an operating temperature set in the present invention. In the present embodiment, the operation guarantee temperature range of the load 21 is a temperature range of a lower-limit operating temperature $T_{lower}$ or higher and an upper-limit operating temperature $T_{upper}$ or lower. In other words, in the present embodiment, the lower-limit operating temperature $T_{lower}$ is a least element of temperatures included in the operation guarantee temperature range of the load 21, and the upper-limit operating temperature $T_{upper}$ is a greatest element of the temperatures included in the operation guarantee temperature range of the load 21.

A temperature lower than the lower-limit operating temperature $T_{lower}$ is not included in the operation guarantee temperature range, but is included in a lower bound of the operation guarantee temperature range. A temperature lower than the lower-limit operating temperature $T_{lower}$ is hereinafter also referred to as a lower-bound temperature. In addition, a temperature higher than the upper-limit operating temperature $T_{upper}$ is not included in the operation guarantee temperature range, but is included in an upper-bound temperature range of the operation guarantee temperature range. A temperature higher than the upper-limit operating temperature $T_{upper}$ is hereinafter also referred to as an upper-bound temperature. As shown in FIG. 9, the upper-bound temperature is an example of the upper-bound temperature range of the operating temperature set in the present invention, and the lower-bound temperature is an example of the lower-bound temperature range of the operating temperature set in the present invention. During operation of the aerosol inhaler 1, the load 21 is controlled such that a temperature thereof is one included in the operation guarantee temperature range of the load 21 and is not the upper-bound temperature or the lower-bound temperature.

Here, the upper-limit operating temperature $T_{upper}$ is a temperature predetermined by the manufacturer of the aerosol inhaler 1 as a temperature for stopping (prohibiting) heating of the load 21. As an example, the upper-limit operating temperature $T_{upper}$ is set to 300° C. in the present embodiment. As shown in FIG. 9, the upper-limit operating temperature $T_{upper}$ is an example of an upper limit temperature, that is, an example of the greatest element in the operating temperature set in the present invention.

The lower-limit operating temperature $T_{lower}$ is a temperature predetermined by the manufacturer of the aerosol inhaler 1 as a temperature for not allowing (prohibiting) electricity discharge to the load 21. As an example, the lower-limit operating temperature $T_{lower}$ is −10° C. in the present embodiment. That is, the lower-limit operating temperature $T_{lower}$ is, for example, the same temperature as the least element of temperature included in the operation guarantee temperature range of the aerosol inhaler 1 itself. As shown in FIG. 9, the lower-limit operating temperature $T_{lower}$ is an example of a lower limit temperature, that is, an example of the least element in the operating temperature set in the present invention.

In the present embodiment, when the temperature T of the load 21 is included in a detectable temperature range that is a temperature range of a detectable lower-limit temperature $T_{MIN}$ or higher and a detectable upper-limit temperature $T_{MAX}$ or lower, the processor 55 can detect the temperature T of the load 21 based on the output signal of the operational amplifier 56. That is, in the present embodiment, the detectable lower-limit temperature $T_{MIN}$ is the least element of temperature included in the detectable temperature range, and the detectable upper-limit temperature $T_{MAX}$ is the greatest element of temperature included in the detectable temperature range. In the present specification, detection of the temperature T being possible means that the temperature T can be uniquely specified.

For example, when the target temperature $T_{tar}$ is determined as in the aerosol inhaler 1 of the present embodiment, as shown in FIG. 9, the detectable temperature range is a set as a temperature range including the target temperature $T_{tar}$. On the other hand, the target temperature $T_{tar}$ may not be determined as in a fourth modification to be described later. When the target temperature $T_{tar}$ is not determined, the detectable temperature range is set as, for example, a temperature range including the upper-limit operating temperature $T_{upper}$ (see FIG. 18 and the like).

Although FIG. 9 shows an example in which the detectable upper-limit temperature $T_{MAX}$ and the upper-limit operating temperature $T_{upper}$ are set to different temperatures, the detectable upper-limit temperature $T_{MAX}$ and the upper-limit operating temperature $T_{upper}$ may be set to the same temperature. For example, both the detectable upper-limit temperature $T_{MAX}$ and the upper-limit operating temperature $T_{upper}$ may be set to 300° C. Similarly, the detectable lower-limit temperature $T_{MIN}$ and the lower-limit operating temperature $T_{lower}$ may be set to the same temperature.

As shown in FIG. 9, a temperature range of the lower-limit operating temperature $T_{lower}$ or higher and lower than the detectable lower-limit temperature $T_{MIN}$ is an example of a subset of the operating temperature set in the present invention, and more specifically, an example of a subset including the lower limit temperature. A temperature range higher than the detectable upper-limit temperature $T_{MAX}$ and equal to or lower than the upper-limit operating temperature $T_{upper}$ is another example of a subset of the operating temperature set in the present invention, and more specifically, an example of a subset including the upper limit temperature.

(Example of Detectable Temperature Range)

Next, a specific example of the detectable temperature range of the aerosol inhaler 1 of the present embodiment will be described with reference to FIG. 10. As described with reference to FIG. 8, the aerosol inhaler 1 described here performs control of restricting the temperature T of the load 21 to the target temperature $T_{tar}$ based on the comparison result between the temperature T of the load 21 and the target temperature $T_{tar}$.

In the aerosol inhaler 1, for example, when the target temperature $T_{tar}$ is set to 250° C., the detectable lower-limit temperature $T_{MIN}$ is set to 200° C. to be 50° C. lower than the target temperature $T_{tar}$ and the detectable upper-limit temperature $T_{MAX}$ is set to 300° C. to be 50° C. higher than the target temperature $T_{tar}$, the temperature T of the load 21 can be restricted to 250° C. with sufficient accuracy, which is the target temperature $T_{tar}$.

Figure 10:
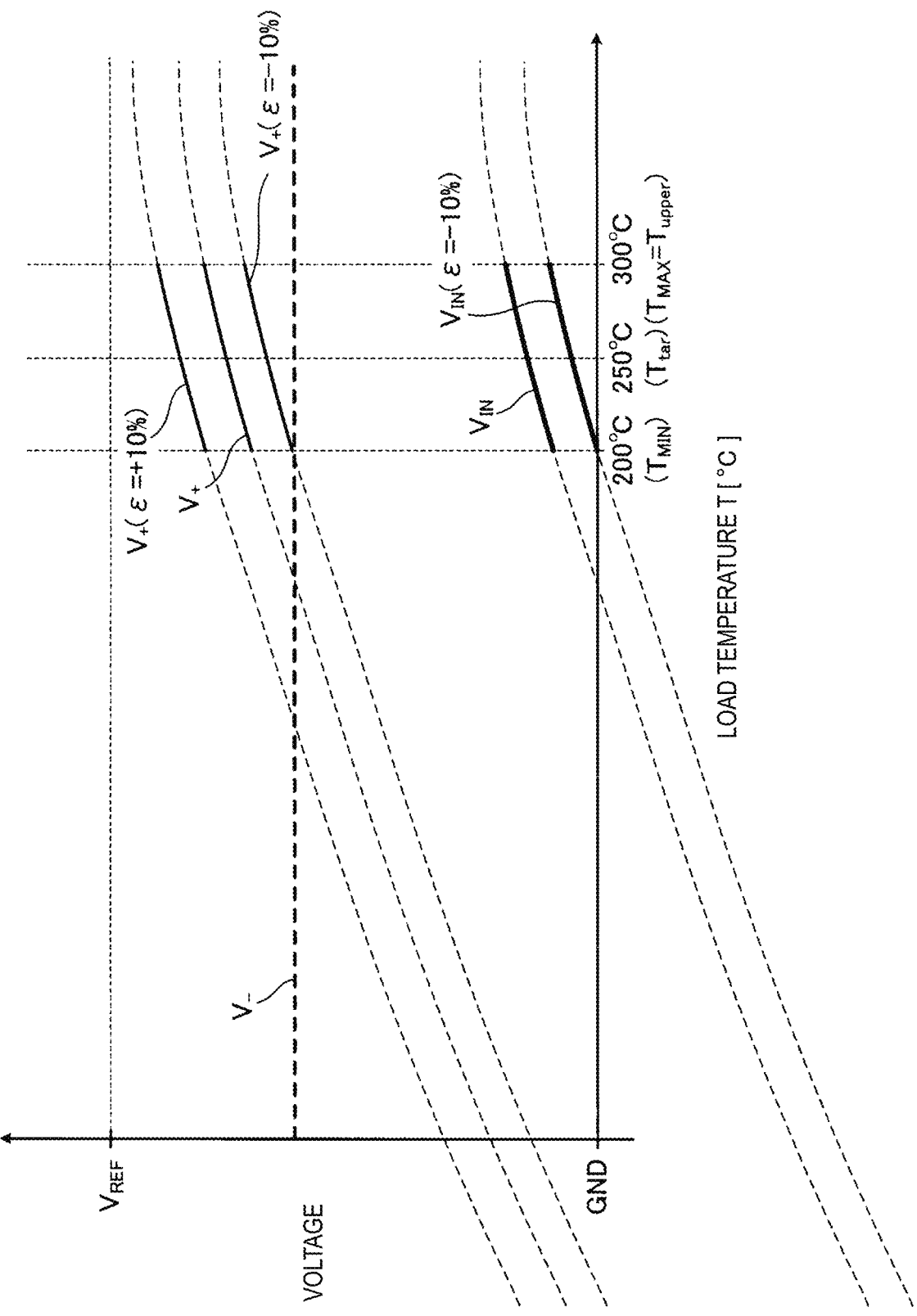
FIG. 10 is a graph showing a specific example of a detectable temperature range of the aerosol inhaler shown in FIG. 1.

Accordingly, in FIG. 10, an example is shown in which the target temperature $T_{tar}$ is set to 250° C., the detectable lower-limit temperature $T_{MIN}$ is set to 200° C., the detectable upper-limit temperature $T_{MAX}$ is set to 300° C., and the detectable temperature range is set to 200° C. or higher and 300° C. or lower. In FIG. 10, a vertical axis indicates the voltage $V_+$ input to the non-inverting input terminal 56a of the operational amplifier 56, voltage $V_−$ input to the inverting input terminal 56b, and magnitude (that is, voltage) of the differential input $V_{IN}$, and a horizontal axis indicates the temperature T of the load 21. In FIG. 10, of the differential input $V_{IN}$ and a differential input $V_{IN}$ (ε=−10%) to be described later, a part of a portion drawn by a broken line indicates potential smaller than the potential of the ground GND, which is the potential of the negative power supply terminal 56e. It should be noted that this is only for understanding how the differential input behaves with respect to the temperature T of the load 21 if the sticking of the output signal or the differential input does not occur. In a real system, the sticking of the output signal and the differential input occurs at the potential of the ground GND that is the potential of the negative power supply terminal 56e (the minimum value that can be handled by the operational amplifier 56 when the operational amplifier 56 is the non-input/output rail-to-rail type). The same applies to FIG. 12 (first modification), FIG. 14 (second modification), FIG. 16 (third modification), FIG. 18 (fourth modification), and FIG. 20 (fifth modification) to be described later.

As described above, since the load 21 has the PTC characteristic, the electric resistance value $R_H$ of the load 21 increases as the temperature T of the load 21 increases. Therefore, as shown in FIG. 10, the voltage $V_+$ input to the non-inverting input terminal 56a of the operational amplifier 56 in a case where the voltage V is applied to the entire parallel circuit formed of the first series circuit C1 and the second series circuit C2 increases as the temperature T of the load 21 increases (see also the above Formula (F1)).

On the other hand, the second electric resistance value $R_2$ of the second element 64 and the third electric resistance value $R_3$ of the third element 65 are constant regardless of the temperature T of the load 21. Accordingly, as shown in FIG. 10, the voltage $V_-$ input to the inverting input terminal 56b of the operational amplifier 56 in the case where the voltage V is applied to the entire parallel circuit formed of the first series circuit C1 and the second series circuit C2 has a constant value regardless of the temperature T of the load 21 (see also the above Formula (F2)).

The differential input $V_{IN}$ of the operational amplifier 56 is the difference between $V_+$ and $V_-$ (that is, $V_{IN}=V_+-V_-$) as long as no sticking occurs. Therefore, as shown in FIG. 10, the differential input $V_{IN}$ of the operational amplifier 56 in the case where the voltage V is applied to the entire parallel circuit formed of the first series circuit C1 and the second series circuit C2 is obtained by shifting the $V_+$ toward a minus side of the vertical axis shown in FIG. 10 by the above $V_-$. Similarly to the $V_+$, the differential input $V_{IN}$ increases as the temperature T of the load 21 increases.

In the present embodiment, the positive power supply terminal 56d of the operational amplifier 56 is connected to the reference voltage $V_{REF}$, and the negative power supply terminal 56e is connected to the ground GND (see FIG. 7). Accordingly, a maximum value that the differential input $V_{IN}$ of the operational amplifier 56 can take is one corresponding to the reference voltage $V_{REF}$ (the maximum value that can be handled by the operational amplifier 56 when the operational amplifier 56 is the non-input/output rail-to-rail type). A minimum value that the differential input $V_{IN}$ of the operational amplifier 56 can take is one corresponding to the voltage of the ground GND (the minimum value that the operational amplifier 56 can handle when the operational amplifier 56 is the non-input/output rail-to-rail type).

Similarly, a maximum value of voltage that the output signal $A \times V_{IN}$ (that is, $A \times (V_+ - V_-)$) of the operational amplifier 56 can take is one corresponding to the reference voltage $V_{REF}$ (the maximum value that can be handled by the operational amplifier 56 when the operational amplifier 56 is the non-input/output rail-to-rail type). Further, a minimum value of voltage that the output signal $A \times V_{IN}$ can take is one corresponding to the voltage of the ground GND (the minimum value that can be handled by the operational amplifier 56 when the operational amplifier 56 is the non-input/output rail-to-rail type).

In order to set the detectable temperature range to 200° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 200° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type).

That is, the manufacturer of the aerosol inhaler 1 may select the electric resistance values $R_H$, $R_1$, $R_2$, $R_3$ and the amplification factor A such that the value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 200° C. to 300° C., is one corresponding to the voltage of the ground GND or larger (the minimum value or higher that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). The manufacturer of the aerosol inhaler 1 may configure the aerosol inhaler 1 using the selected electric resistance values $R_H$, $R_1$, $R_2$, $R_3$ and the amplification factor A.

In selecting the electric resistance values $R_H$, $R_1$, $R_2$, and $R_3$ and the amplification factor A, when the electric resistance values $R_H$, $R_1$, $R_2$, and $R_3$ are selected such that the differential input $V_{IN}$ of the operational amplifier 56 is as small as possible, the amplification factor A can be increased accordingly while suppressing the output signal of the operational amplifier 56 from sticking to the reference voltage $V_{REF}$. When the amplification factor A is increased, the output signal of the operational amplifier 56 can be largely varied in accordance with the change in the temperature T of the load 21, and the temperature T of the load 21 can be detected with higher accuracy based on the output signal of the operational amplifier 56.

In order to reduce the differential input $V_{IN}$ of the operational amplifier 56, for example, the electric resistance values $R_H$, $R_1$, $R_2$, and $R_3$ may be selected such that $V_+$ and $V_-$ at the time when the temperature T of the load 21 is 200° C. (that is, the detectable lower-limit temperature $T_{MIN}$) are equal. In this way, the differential input $V_{IN}$ of the operational amplifier 56 at the time when the temperature T of the load 21 is 200° C. is equal to 0 V, that is, equal to the voltage of the ground GND connected to the negative power supply terminal 56e, and thus the differential input $V_{IN}$ of the operational amplifier 56 can be suppressed from sticking to the voltage of the ground GND when the temperature T of the load 21 is higher than 200° C.

Therefore, in the detectable temperature range of 200° C. or higher, the differential input $V_{IN}$ of the operational amplifier 56 can be reduced while suppressing the output signal $A \times V_{IN}$ of the operational amplifier 56 from sticking to the voltage of the ground GND and enabling detection of the temperature T of the load 21 based on the output signal of the operational amplifier 56. Accordingly, the amplification factor A of the operational amplifier 56 can be increased, and when the temperature T of the load 21 is included in the detectable temperature range, the temperature T can be detected with high accuracy.

Further, the electric resistance value $R_H$ of the load 21 may vary by about ±10% from a design reference value due to a product error of the load 21 itself. Therefore, even if the electric resistance value $R_H$ of the load 21 varies due to the product error of the load 21, it is preferable that the temperature T of the load 21 can be detected in the detectable temperature range.

Specifically, in FIG. 10, a $V_+(\varepsilon=-10\%)$ indicates a voltage $V_+$ input to the non-inverting input terminal 56a of the operational amplifier 56 in a case where the voltage V is applied to the entire parallel circuit formed of the first series circuit C1 and the second series circuit C2, with the electric resistance value $R_H$ of the load 21 varying by 10% in a − direction from the design reference value (downside deflection). In FIG. 10, a differential input $V_{IN}$ ($\varepsilon=-10\%$) of the operational amplifier 56 indicates a difference between the $V_+(\varepsilon=-10\%)$ and $V_-$ (that is, $V_+(\varepsilon=-10\%)-V_-$).

For example, it is preferable to select the electric resistance values $R_H$, $R_1$, $R_2$, and $R_3$ such that the $V_+(\varepsilon=-10\%)$ and $V_-$ at the time when the temperature T of the load 21 is 200° C. (that is, the detectable lower-limit temperature $T_{MIN}$) are equal as shown in FIG. 10, and configure the aerosol inhaler 1 using the selected electric resistance values $R_H$, $R_1$, $R_2$, and $R_3$. In this way, even if the electric resistance value $R_H$ of the load 21 varies by 10% in the − direction from the design reference value, the differential input $V_{IN}$ of the operational amplifier 56 can be suppressed from sticking to the voltage of the ground GND when the temperature T of the load 21 is higher than 200° C., and the temperature T of the load 21 can be detected in the detectable temperature range.

In FIG. 10, a $V_+(\varepsilon=+10\%)$ indicates a voltage $V_+$ input to the non-inverting input terminal 56a of the operational amplifier 56 in a case where the voltage V is applied to the entire parallel circuit formed of the first series circuit C1 and the second series circuit C2, with the electric resistance value $R_H$ of the load 21 varying by 10% in a + direction from the design reference value (upside deflection). A differential input $V_{IN}$ ($\varepsilon=+10\%$) of the operational amplifier 56 in a case where the $V_+(\varepsilon=+10\%)$ is input to the non-inverting input terminal 56a of the operational amplifier 56 is a difference between the $V_+(\varepsilon=+10\%)$ and $V_-$ (that is, $V_+(\varepsilon=+10\%)-V_-$).

Although not shown and described in detail here, it is preferable to select the electric resistance values $R_H$, $R_1$, $R_2$, and $R_3$ such that the differential input $V_{IN}$ ($\varepsilon=+10\%$) at the time when the temperature T of the load 21 is 300° C. (that is, the detectable upper-limit temperature $T_{MAX}$) is equal to the reference voltage $V_{REF}$ or smaller, and configure the aerosol inhaler 1 using the selected electric resistance values $R_H$, $R_1$, $R_2$, and $R_3$. In this way, even if the electric resistance value $R_H$ of the load 21 varies by 10% in the + direction from the design reference value, the differential input $V_{IN}$ of the operational amplifier 56 can be suppressed from sticking to the reference voltage $V_{REF}$ when the temperature T of the load 21 is lower than 300° C., and the temperature T of the load 21 can be detected in the detectable temperature range.

When a non-input/output rail-to-rail type operational amplifier is used as the operational amplifier 56, the electric resistance values $R_H$, $R_1$, $R_2$, and $R_3$ may be selected such that a difference value, at the time when the temperature T of the load 21 is the detectable lower-limit temperature $T_{MIN}$, between the voltage ($V_+$ or $V_+(\varepsilon=-10\%)$) input to the non-inverting input terminal 56a of the operational amplifier 56 and the voltage input to the inverting input terminal 56b is equal to the minimum value that can be handled by the operational amplifier 56. In addition, it is preferable to select the electric resistance values $R_H$, $R_1$, $R_2$, and $R_3$ such that a difference value, at the time when the temperature T of the load 21 is the detectable upper-limit temperature $T_{MAX}$, between the voltage ($V_+$ or $V_+(\varepsilon=-10\%)$) input to the non-inverting input terminal 56a of the operational amplifier 56 and the voltage input to the inverting input terminal 56b is equal to the maximum value or smaller that can be handled by the operational amplifier 56, and configure the aerosol inhaler 1 using the selected electric resistance values $R_H$, $R_1$, $R_2$, and $R_3$. The same applies to FIG. 12 (first modification), FIG. 14 (second modification), FIG. 16 (third modification), FIG. 18 (fourth modification), and FIG. 20 (fifth modification) to be described later.

As described above, in the aerosol inhaler 1 that restricts the temperature T of the load 21 to the target temperature $T_{tar}$ based on the comparison result between the temperature T of the load 21 and the target temperature $T_{tar}$, the temperature T of the load 21 can be restricted to the target temperature $T_{tar}$ if the temperature T of the load 21 can be detected around the target temperature $T_{tar}$. Specifically, for example, if the temperature T of the load 21 can be detected in a detectable temperature range of ±50° C. of the target temperature $T_{tar}$, the temperature T of the load 21 can be restricted to the target temperature $T_{tar}$ with sufficient accuracy.

Therefore, in the aerosol inhaler 1 of the present embodiment, the difference value, at the time when the temperature T of the load 21 is the target temperature $T_{tar}-50°$ C., between the voltage input to the non-inverting input terminal 56a of the operational amplifier 56 and the voltage input to the inverting input terminal 56b is made equal to the voltage (the minimum value that can be handled by the operational amplifier 56 when the operational amplifier 56 is a non-input/output rail-to-rail type) of the ground GND connected to the negative power supply terminal 56e, so that the temperature T of the load 21 can be detected based on the output signal of the operational amplifier 56 only in an appropriate temperature range of ±50° C. of the target temperature $T_{tar}$.

If the temperature T of the load 21 is made detectable based on the output signal of the operational amplifier 56 in a wide temperature range, the electric resistance values $R_H$, $R_1$, $R_2$, and $R_3$ of the load 21, the first element 63, the second element 64, and the third element 65 need to have a margin from a viewpoint of preventing sticking of the differential input and the output signal of the operational amplifier 56. When the electric resistance values $R_H$, $R_1$, $R_2$, and $R_3$ have a margin, the differential input $V_{IN}$ of the operational amplifier 56 tends to increase, and when the differential input $V_{IN}$ of the operational amplifier 56 is increased, it is difficult to increase the amplification factor A of the operational amplifier 56 from a viewpoint of preventing the sticking of the output signal of the operational amplifier 56.

In contrast, since the aerosol inhaler 1 of the present embodiment is made capable of detecting the temperature T of the load 21 based on the output signal of the operational amplifier 56 only in an appropriate temperature range, providing a margin to the electric resistance values $R_H$, $R_1$, $R_2$, and $R_3$ of the load 21, the first element 63, the second element 64, and the third element 65 in order to excessively suppress the sticking of the output signal of the operational amplifier 56 is unnecessary. Therefore, the differential input $V_{IN}$ of the operational amplifier 56 can be reduced, and the amplification factor A of the operational amplifier 56 can be increased accordingly. Thus, the aerosol inhaler 1 of the present embodiment can detect the temperature T of the load 21 with high accuracy in an appropriate temperature range.

Further, the electric resistance value $R_H$ of the load 21 at the time when the temperature T is the target temperature $T_{tar}$-50° C. may differ by -10% from the design reference value due to the product error. Therefore, in the aerosol inhaler 1 of the present embodiment, the difference value between the voltage input to the non-inverting input terminal 56a of the load 21 and the voltage input to the non-inverting input terminal 56b of the operational amplifier 56 at the time when the temperature T of the load 21 is the target temperature $T_{tar}$-50° C. in a case where the electric resistance value $R_H$ of the load 21 is different by -10% from the design reference value is made equal to the voltage of the negative power supply terminal 56e (the minimum value that can be handled by the operational amplifier 56 when the operational amplifier 56 is non-input/output rail-to-rail type).

Accordingly, even if there is a product error in the load 21, the aerosol inhaler 1 of the present embodiment can suppress the sticking of the differential input and the output signal of the operational amplifier 56, and can detect the temperature T of the load 21 with high accuracy in an appropriate temperature range. That is, even if there is a product error in the load 21, the aerosol inhaler 1 of the present embodiment can suppress an erroneous temperature from being acquired as the temperature T of the load 21. Therefore, the aerosol inhaler 1 of the present embodiment can appropriately manage the temperature T of the load 21 by suppressing occurrence of a situation such as one in which the load 21 is excessively heated based on the erroneous temperature.

(First Modification of Aerosol Inhaler)

Next, a first modification of the aerosol inhaler 1 will be described. The first modification is different from the above-described embodiment in that calibration is performed on the reference temperature $T_{REF}$ and the reference electric resistance value $R_{REF}$ (see Formula (F0)). By performing calibration on the reference temperature $T_{REF}$ and the reference electric resistance value $R_{REF}$ as in the first modification, it is possible to detect the temperature T of the load 21 with higher accuracy based on the above Formula (F0). In the following description of the first modification, the same parts as those in the above-described embodiment are denoted by the same reference signs, and descriptions thereof are omitted as appropriate.

(Example of Specific Operations of Aerosol Inhaler of First Modification)

Figure 11:
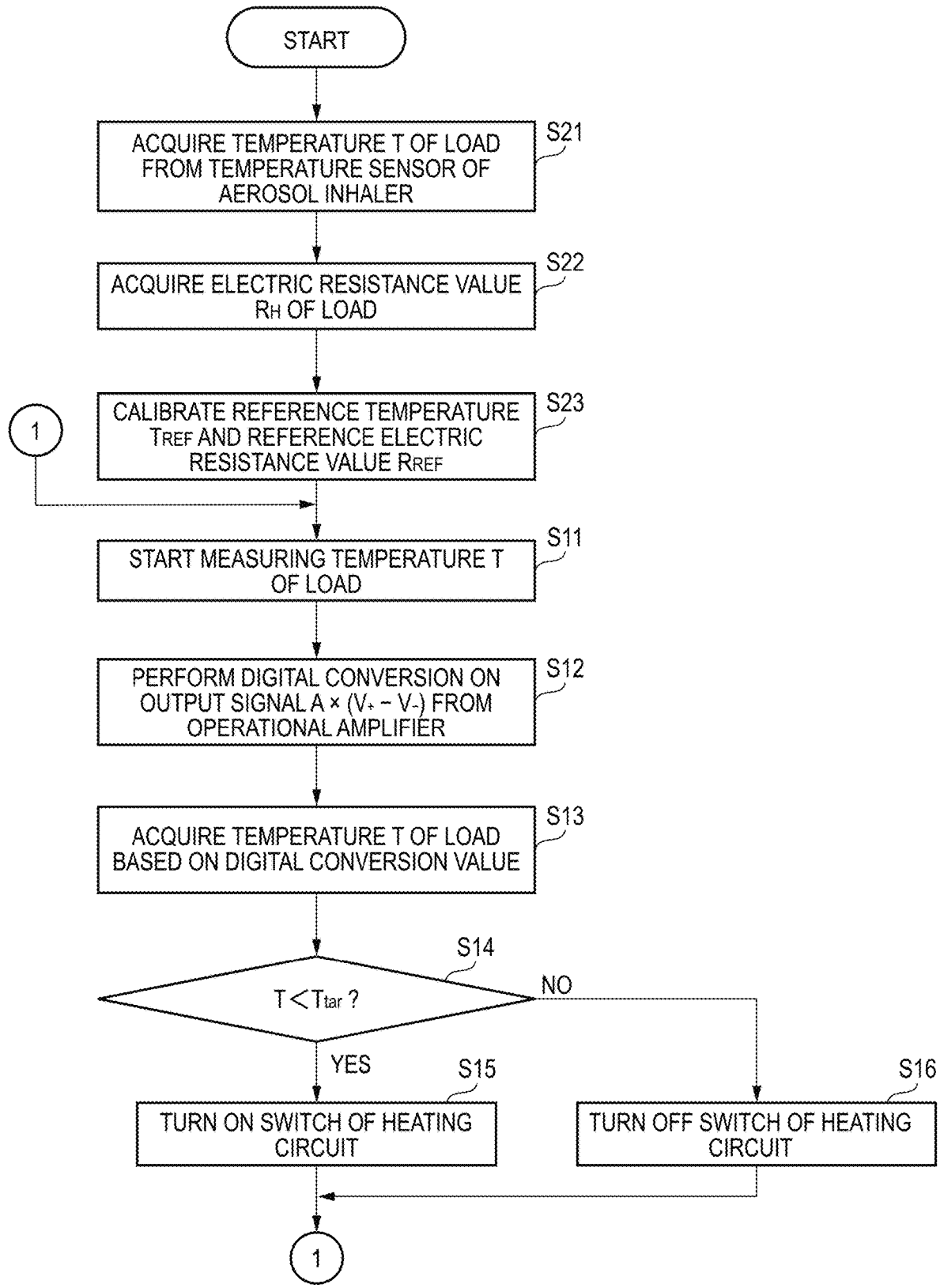
FIG. 11 is a flowchart showing an example of operations of a first modification of the aerosol inhaler shown in FIG. 1.

An example of specific operations of the aerosol inhaler 1 of the first modification will be described with reference to FIG. 11. As shown in FIG. 11, when it is the timing of performing calibration on the reference temperature $T_{REF}$ and the reference electric resistance value $R_{REF}$ in the aerosol inhaler 1 of the first modification, the processor 55 of the MCU 50 acquires the temperature T of the load 21 from a temperature sensor included in the aerosol inhaler 1 (step S21).

Here, the temperature sensor included in the aerosol inhaler 1 is, for example, the intake sensor 15. Specifically, the intake sensor 15 has a temperature sensor that detects an ambient air temperature for calibration of an output value, and sends a temperature detected by the temperature sensor to the processor 55. In step S21, the processor 55 acquires the ambient air temperature detected by the intake sensor 15 as the temperature T of the load 21.

With respect to significance of acquiring the ambient air temperature as the temperature T of the load 21, the temperature T of the load 21 immediately after being replaced is likely to be substantially the same as the ambient air temperature. Therefore, a timing at which the load 21 is replaced is taken as the timing of performing calibration on the reference temperature $T_{REF}$ and the reference electric resistance value $R_{REF}$, and the ambient air temperature detected by the intake sensor 15 at that time is acquired as the temperature T of the load 21, so that it is possible to acquire the temperature T of the load 21 with high accuracy even when a temperature sensor is not provided on the load 21 itself.

When the aerosol inhaler 1 has a temperature sensor that detects a temperature of the power supply 12, the processor 55 may acquire a temperature detected by the temperature sensor, which detects the temperature of the power supply 12, as the temperature T of the load 21 in step S21.

Next, the processor 55 acquires the electric resistance value $R_H$ of the load 21 (step S22). In step S22, for example, the processor 55 sends an off command to the switch 61 and an on command to the switch 62 as in step S11 to output an output signal $A\times(V_+-V_-)$ from the operational amplifier 56, and causes the output signal $A\times(V_+-V_-)$ to be input to the ADC 57. Further, the processor 55 acquires the electric resistance value $R_H$ of the load 21 based on a digital conversion value of the $A\times(V_+-V_-)$ output by the ADC 57 and on the above Formula (F3). Note that the processor 55 may change an order in which the steps S21 and S22 are executed, or may perform the steps S21 and S22 at the same time.

Next, the processor 55 performs calibration on the reference temperature $T_{REF}$ and the reference electric resistance value $R_{REF}$ based on the temperature T of the load 21 acquired in step S21 and the electric resistance value $R_H$ of the load 21 acquired in step S22 (step S23). In step S23, for example, the processor 55 sets the temperature of the load 21 acquired in step S21 as the reference temperature $T_{REF}$, and sets the electric resistance value $R_H$ acquired in step S22 as the reference electric resistance value $R_{REF}$. The reference temperature $T_{REF}$ and the reference electric resistance value $R_{REF}$ set here are used to solve Formula (F0) below.

When the reference temperature $T_{REF}$ and the reference electric resistance value $R_{REF}$ are calibrated in step S23, the aerosol inhaler 1 of the first modification repeats the operations of step S11 and following steps described above as shown in FIG. 11.

When the calibration is to be performed on the reference temperature $T_{REF}$ and the reference electric resistance value $R_{REF}$ as in the first modification, it is necessary to obtain the electric resistance value $R_H$ of the load 21 based on the output signal of the operational amplifier 56, at the timing of performing calibration on the reference temperature $T_{REF}$ and the reference electric resistance value $R_{REF}$ (step S22). At the timing of performing calibration on the reference temperature $T_{REF}$ and the reference electric resistance value $R_{REF}$, the load 21 may take any temperature included in the operation guarantee temperature range of the load 21.

Therefore, when the calibration is to be performed on the reference temperature $T_{REF}$ and the reference electric resistance value $R_{REF}$ as in the first modification, a detectable temperature range needs to be widened as compared with that in the above-described embodiment, taking the detectable upper-limit temperature $T_{MAX}$ as the upper-limit operating temperature $T_{upper}$ and the detectable lower-limit temperature $T_{MIN}$ as the lower-limit operating temperature $T_{lower}$.

(Example of Detectable Temperature Range of First Modification)

Here, an example of the detectable temperature range of the first modification will be described with reference to FIG. 12. The example shown in FIG. 12 is an example in which, since the upper-limit operating temperature $T_{upper}$ is 300° C. and the lower-limit operating temperature $T_{lower}$ is −10° C., the detectable upper-limit temperature $T_{MAX}$ is se to 300° C., the detectable lower-limit temperature $T_{MIN}$ is set to −10° C., and the detectable temperature range is set to −10° C. to 300° C.

Figure 12:
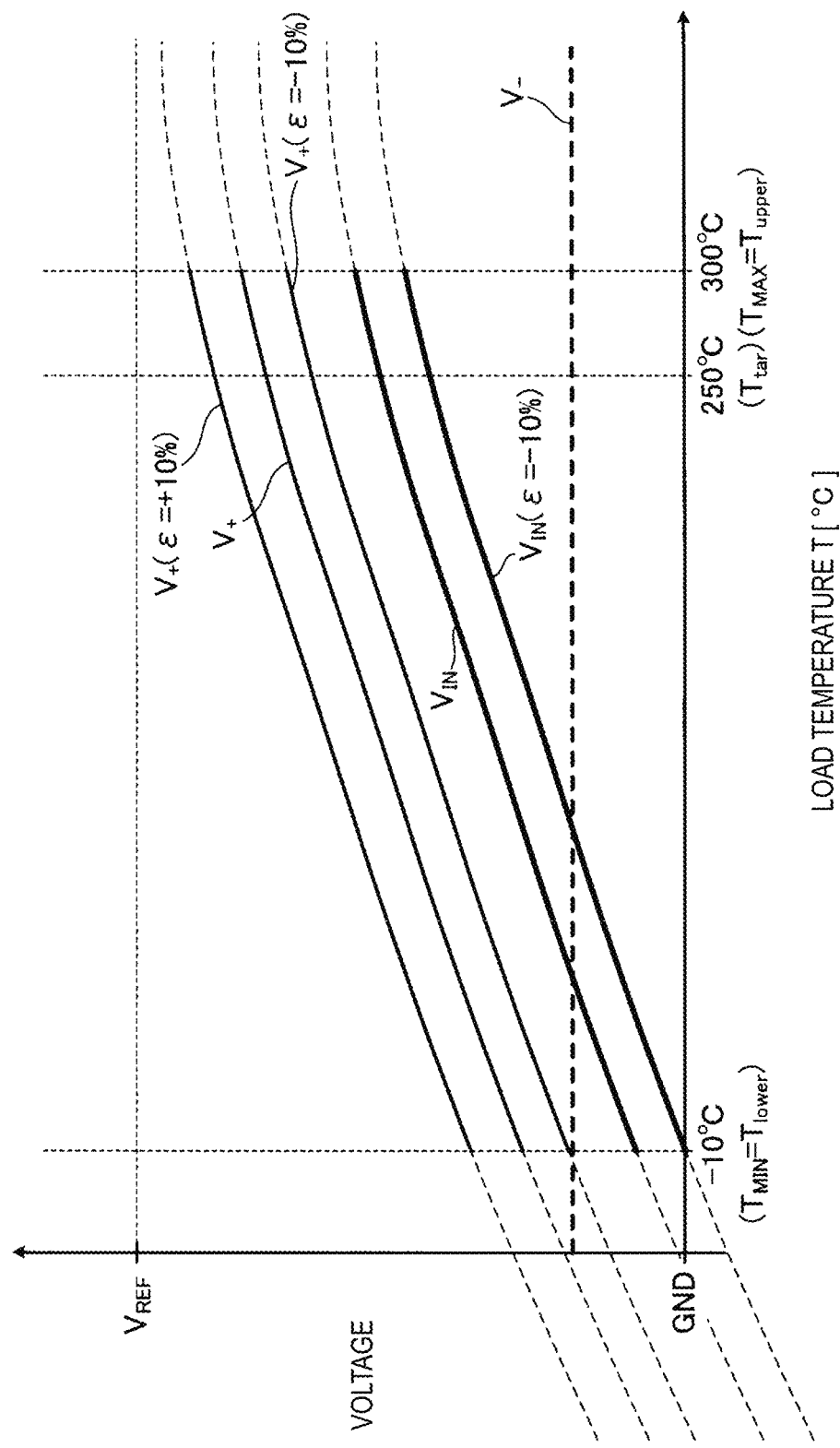
FIG. 12 is a graph showing a specific example of a detectable temperature range of the first modification of the aerosol inhaler shown in FIG. 1.

Similarly to FIG. 10, in FIG. 12, a vertical axis indicates the voltage $V_+$ input to the non-inverting input terminal 56*a* of the operational amplifier 56, the voltage $V_-$ input to the inverting input terminal 56*b*, and magnitude (that is, voltage) of the differential input $V_{IN}$, and a horizontal axis indicates the temperature T of the load 21.

In order to set the detectable temperature range to −10° C. to 300° C., a value obtained by multiplying, by the amplification factor A, the differential input or the difference value between the voltage input to the non-inverting input terminal 56*a* of the operational amplifier 56 and the voltage input to the inverting input terminal 56*b* when the temperature T of the load 21 is −10° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type).

That is, the manufacturer of the aerosol inhaler 1 may select the electric resistance values $R_H$, $R_1$, $R_2$, $R_3$ and the amplification factor A such that the value obtained by multiplying, by the amplification factor A, the differential input or the difference value between the voltage input to the non-inverting input terminal 56*a* of the operational amplifier 56 and the voltage input to the inverting input terminal 56*b* when the temperature T of the load 21 is −10° C. to 300° C., is one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). The manufacturer of the aerosol inhaler 1 may configure the aerosol inhaler 1 using the selected electric resistance values $R_H$, $R_1$, $R_2$, $R_3$ and the amplification factor A.

More specifically, for example, the electric resistance values $R_H$, $R_1$, $R_2$, and $R_3$ may be selected such that the $V_+$ and $V_-$ at the time when the temperature T of the load 21 is −10° C. (that is, the detectable lower-limit temperature $T_{MIN}$) are equal. In this way, the differential input $V_{IN}$ of the operational amplifier 56 at the time when the temperature T of the load 21 is −10° C. is equal to 0 V, that is, equal to the voltage of the ground GND connected to the negative power supply terminal 56*e*, and thus the differential input $V_{IN}$ of the operational amplifier 56 can be suppressed from sticking to the voltage of the ground GND when the temperature T of the load 21 is higher than −10° C.

Therefore, in the detectable temperature range of −10° C. or higher, the differential input $V_{IN}$ of the operational amplifier 56 can be reduced while suppressing the output signal $A \times V_{IN}$ of the operational amplifier 56 from sticking to the voltage of the ground GND and enabling detection of the temperature T of the load 21 based on the output signal of the operational amplifier 56.

Also in the first modification, it is preferable to consider the product error of the load 21. For example, the electric resistance values $R_H$, $R_1$, $R_2$, and $R_3$ may be selected such that a difference between a $V_+(\varepsilon=-10\%)$ and the $V_-$ at the time when the temperature T of the load 21 is −10° C. (that is the detectable lower-limit temperature $T_{MIN}$) is equal to the voltage of the ground GND (the minimum value that can be handled by the operational amplifier 56 when the operational amplifier 56 is the non-input/output rail-to-rail type) as shown in FIG. 12, and the aerosol inhaler 1 may be configured using the selected electric resistance values $R_H$, $R_1$, $R_2$, and $R_3$. In this case, the temperature T of the load 21 can be detected in the above-described detectable temperature range even when the electric resistance value $R_H$ of the load 21 varies by 10% in a − direction from a reference value.

As described above, in the aerosol inhaler 1 of the first modification, in the operation guarantee temperature range in which the lower-limit operating temperature $T_{lower}$ is the least element and the upper-limit operating temperature $T_{upper}$ is the greatest element, the difference value between the voltage input to the non-inverting input terminal 56*a* of the operational amplifier 56 and the voltage input to the inverting input terminal 56*b* thereof is equal to or larger than the voltage of the negative power supply terminal 56*e* of the operational amplifier 56 (the minimum value or larger that can be handled by the operational amplifier 56 when the operational amplifier 56 is the non-input/output rail-to-rail type). Thus, when the temperature T of the load 21 is in the operation guarantee temperature range, the sticking of the differential input and the output signal, of the operational amplifier 56, can be suppressed. Therefore, it is possible to appropriately perform calibration for detecting the temperature T of the load 21.

(Second Modification of Aerosol Inhaler)

Next, a second modification of the aerosol inhaler 1 will be described. The second modification is different from the above-described embodiment in that the temperature T of the load 21 is controlled using pulse width modulation (PWM) control. As in the second modification, by controlling the temperature T of the load 21 using PWM control, it is possible to control the temperature T of the load 21 more easily. In the following description of the second modification, the same parts as those in the above-described embodiment are denoted by the same reference signs, and description thereof are omitted as appropriate.

(Example of Specific Operations of Aerosol Inhaler of First Modification)

An example of specific operations of the aerosol inhaler 1 of the second modification will be described with reference to FIG. 13. As shown in FIG. 13, when, for example, it is the timing for detecting the temperature T of the load 21 in the aerosol inhaler 1 of the second modification, the processor 55 of the MCU 50 starts measuring the temperature T of the load 21 (step S31). In step S31, similarly to step S11, the processor 55 turns off the switch 61 while turning on the switch 62 so that a current flows through the first series circuit C1 and the second series circuit C2 downstream of the switch 62. Accordingly, $A \times (V_+ - V_-)$ is output from the operational amplifier 56 as an output signal, which is input to the ADC 57.

Further, the ADC 57 performs digital conversion on the input $A \times (V_+ - V_-)$ (step S32), and outputs the obtained digital conversion value to the processor 55. Similarly to step S13, the processor 55 acquires the temperature T of the load 21 based on the digital conversion value received from the ADC 57 (that is, the digital conversion value of the output signal of the operational amplifier 56) (step S33).

Next, the processor 55 determines a duty command value for controlling the temperature T of the load 21 based on a temperature difference ΔT between the target temperature $T_{tar}$ and the temperature T of the load 21 (that is, $\Delta T=T_{tar}-T$) (step S34). In the second modification, for example, PWM control information shown in FIG. 13 is stored in advance in a ROM or the like (not shown).

Figure 13:
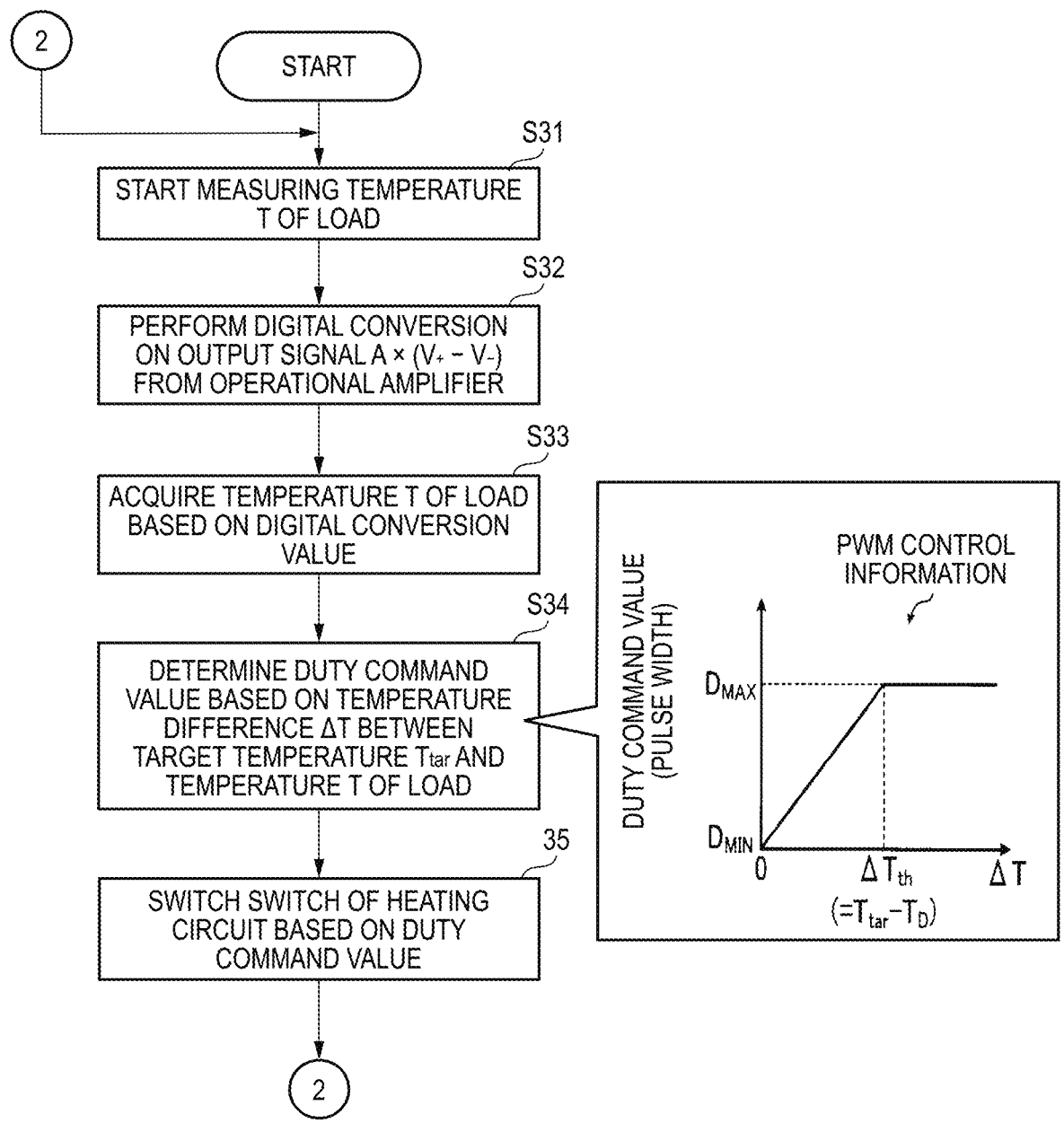
FIG. 13 is a flowchart showing an example of operations of a second modification of the aerosol inhaler shown in FIG. 1.

As shown in FIG. 13, the PWM control information is information in which a duty command value for a temperature difference $\Delta T$ is determined in associated with the temperature difference $\Delta T$. Here, for example, the duty command value indicates a pulse width, in a switching period, of an on command to be sent to the switch 61 in order to control the temperature T of the load 21, that is, a pulse width, in the switching period, of power supplied to the load 21 via a heating circuit.

As shown in FIG. 13, in the PWM control information, a duty command value at the time when the temperature difference $\Delta T$ is 0 is set to a minimum value of $D_{MIN}$ (for example, a pulse width with a duty ratio of 0%) that can be taken as a duty command value. In addition, in the PWM control information, the duty command value also increases as the temperature difference $\Delta T$ increases from zero. In the PWM control information, duty command values at the time when the temperature difference $\Delta T$ is equal to or larger than a predetermined threshold value $\Delta T_{th}$ are set to a maximum value of $D_{MAX}$ (for example, a pulse width with a duty ratio of 100%) that can be taken as a duty command value. Hereinafter, a temperature T of the load 21 at which the temperature difference $\Delta T$ is the threshold $\Delta T_{th}$ is referred to as a threshold temperature $T_D$. That is, the threshold $\Delta T_{th}$=the target temperature $T_{tar}$– the threshold temperature $T_D$.

In step S34 described above, first, the processor 55 acquires the temperature difference $\Delta T$ based on the temperature T of the load 21 acquired in step S33 and the target temperature $T_{tar}$. Further, the processor 55 determines a duty command value based on the acquired temperature difference $\Delta T$ and the PWM control information.

When the duty command value is determined, the processor 55 controls switching of the switch 61 based on the determined duty command value (step S35). Thus, the processor 55 can perform control using the PWM control such that the temperature T of the load 21 is the target temperature $T_{tar}$.

When the temperature T of the load 21 is PWM-controlled as in the second modification, if the temperature of the load 21 can be detected in a temperature range of the threshold temperature $T_D$ or higher and the target temperature $T_{tar}$, the temperature T of the load 21 can be restricted to the target temperature $T_{tar}$ with sufficient accuracy. For example, here, the threshold temperature $T_D$ is a temperature (for example, 100° C.) lower than the detectable lower-limit temperature $T_{MIN}$ (that is, 200° C.) in the example of the above-described embodiment.

Therefore, when the temperature T of the load 21 is PWM-controlled as in the second modification, a detectable temperature range needs to be widened as compared with that in the example of the above-described embodiment, with the detectable lower-limit temperature $T_{MIN}$ taken as the threshold temperature $T_D$.

(Example of Detectable Temperature Range of Second Modification)

Here, an example of the detectable temperature range of the second modification will be described with reference to FIG. 14. The example shown in FIG. 14 is an example in which the detectable temperature range is set to 100° C. to 300° C. by setting the detectable upper-limit temperature $T_{MAX}$ to 300° C. and the detectable lower-limit temperature $T_{MIN}$ to 100° C. as the threshold temperature $T_D$.

Figure 14:
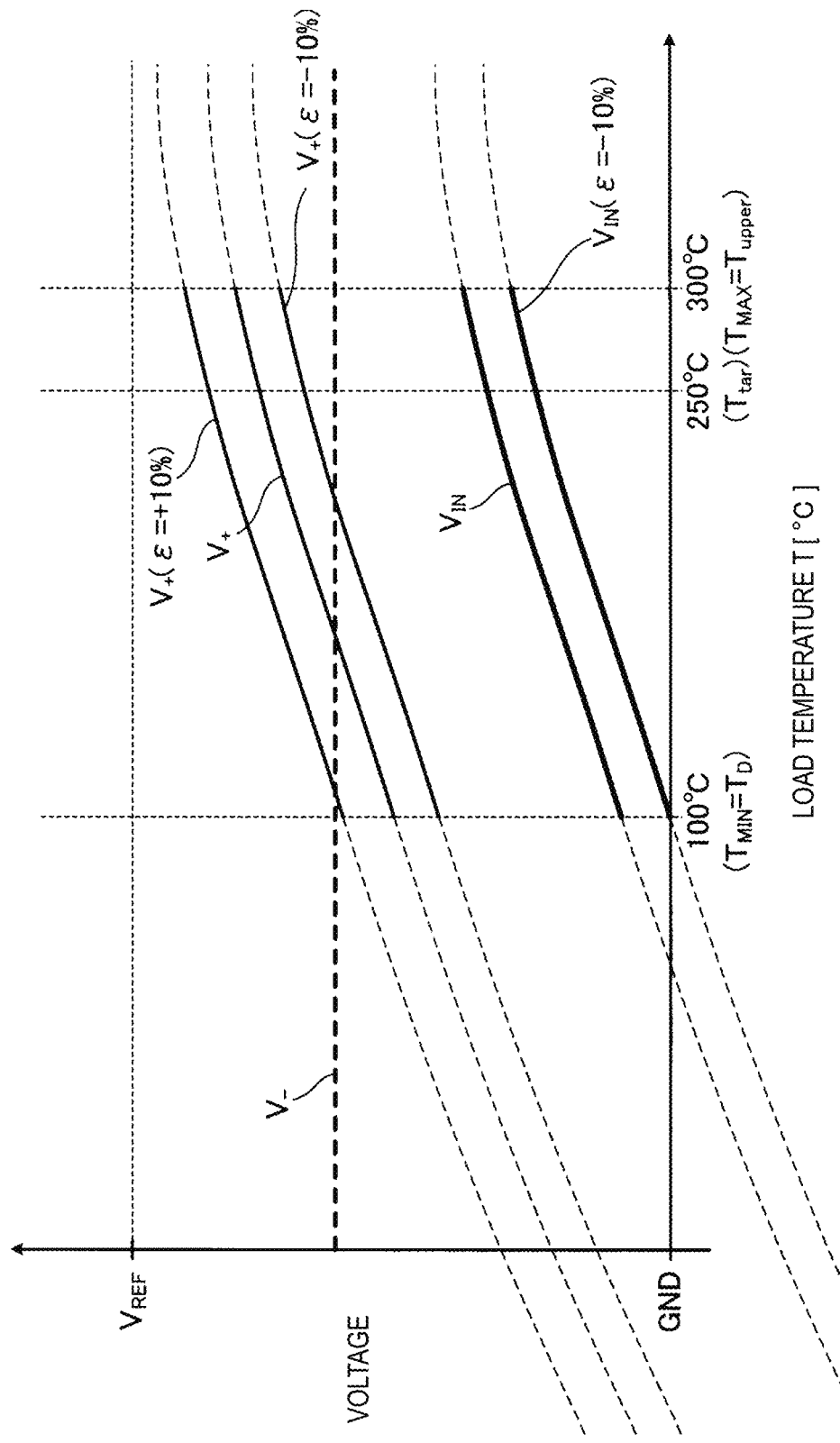
FIG. 14 is a graph showing a specific example of a detectable temperature range of the second modification of the aerosol inhaler shown in FIG. 1.

Similarly to FIG. 10, in FIG. 14, a vertical axis indicates the voltage $V_+$ input to the non-inverting input terminal 56a of the operational amplifier 56, the voltage $V_-$ input to the inverting input terminal 56b, and magnitude (that is, voltage) of the differential input $V_{IN}$, and a horizontal axis indicates the temperature T of the load 21.

In order to set the detectable temperature range to 100° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 100° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type).

That is, the manufacturer of the aerosol inhaler 1 may select the electric resistance values $R_H$, $R_1$, $R_2$, $R_3$ and the amplification factor A such that the value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 100° C. to 300° C., is one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). The manufacturer of the aerosol inhaler 1 may configure the aerosol inhaler 1 using the selected electric resistance values $R_H$, $R_1$, $R_2$, $R_3$ and the amplification factor A.

More specifically, for example, the electric resistance values $R_H$, $R_1$, $R_2$, and $R_3$ may be selected such that the $V_+$ and $V_-$ at the time when the temperature T of the load 21 is 100° C. (that is, the detectable lower-limit temperature $T_{MIN}$) are equal. In this way, the differential input $V_{IN}$ of the operational amplifier 56 at the time when the temperature T of the load 21 is 100° C. is equal to 0 V, that is, equal to the voltage of the ground GND connected to the negative power supply terminal 56e, and thus the differential input $V_{IN}$ of the operational amplifier 56 can be suppressed from sticking to the voltage of the ground GND when the temperature T of the load 21 is higher than 100° C.

Therefore, in the detectable temperature range of 100° C. or higher, the differential input $V_{IN}$ of the operational amplifier 56 can be reduced while suppressing the output signal $A \times V_{IN}$ of the operational amplifier 56 from sticking to the voltage of the ground GND and enabling detection of the temperature T of the load 21 based on the output signal of the operational amplifier 56.

Also in the second modification, it is preferable to consider the product error of the load 21. For example, the electric resistance values $R_H$, $R_1$, $R_2$, and $R_3$ may be selected such that a difference between a $V_+(\varepsilon=-10\%)$ and the $V_-$ at the time when the temperature T of the load 21 is 100° C. (that is the detectable lower-limit temperature $T_{MIN}$) is equal to the voltage of the ground GND (the minimum value that can be handled by the operational amplifier 56 when the operational amplifier 56 is the non-input/output rail-to-rail type) as shown in FIG. 14, and the aerosol inhaler 1 may be configured using the selected electric resistance values $R_H$, $R_1$, $R_2$, and $R_3$. In this case, the temperature T of the load 21 can be detected in the above-described detectable temperature range even when the electric resistance value $R_H$ of the load 21 varies by 10% in a − direction from a reference value.

As described above, in the aerosol inhaler 1 of the second modification, in a temperature range in which the threshold temperature $T_D$ at which the duty command value indicating the pulse width of the power supplied to the load 21 via the heating circuit is the maximum value $D_{MAX}$ is set as the least element and the target temperature $T_{tar}$ is included, the difference value between the voltage input to the non-inverting input terminal 56a of the operational amplifier 56 and the voltage input to the inverting input terminal 56b is equal to or larger than the voltage of the negative power supply terminal 56e of the operational amplifier 56 (the minimum value or larger that can be handled by the operational amplifier 56 when the operational amplifier 56 is the non-input/output rail-to-rail type). Thus, when the temperature T of the load 21 is in the temperature range, the sticking of the differential input and the output signal, of the operational amplifier 56, can be suppressed. Therefore, the temperature T of the load 21 can be accurately restricted to the target temperature $T_{tar}$.

(Third Modification of Aerosol Inhaler)

Next, a third modification of the aerosol inhaler 1 will be described. The third modification is different from the second modification in that calibration is performed on the reference temperature $T_{REF}$ and the reference electric resistance value $R_{REF}$ (see Formula (F0)). That is, the aerosol inhaler 1 of the third modification performs calibration on the reference temperature $T_{REF}$ and the reference electric resistance value $R_{REF}$ as in the first modification, and performs PWM control on the temperature T of the load 21 based on PWM control information as in the second modification. In the following description of the third modification, the same reference signs are given to the same parts as those in the first and second modifications, and descriptions thereof are omitted as appropriate.

(Example of Specific Operations of Aerosol Inhaler of Third Modification)

Figure 15:
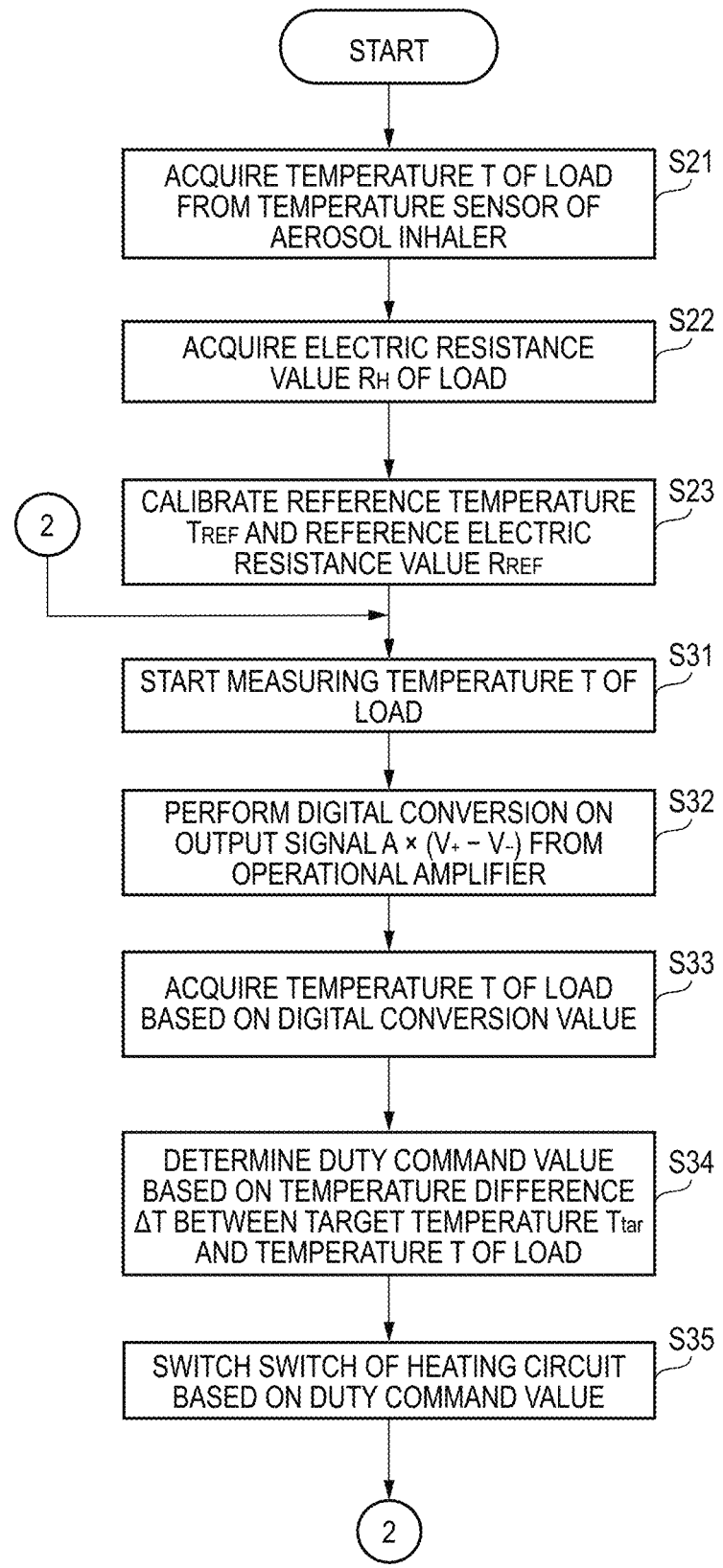
FIG. 15 is a flowchart showing an example of operations of a third modification of the aerosol inhaler shown in FIG. 1.

An example of specific operations of the aerosol inhaler 1 of the third modification will be described with reference to FIG. 15. As shown in FIG. 15, in the aerosol inhaler 1 of the third modification, after the operations of steps S21 to S23 are performed, the operations of steps S31 to S35 are performed.

When the calibration is performed on the reference temperature $T_{REF}$ and the reference electric resistance value $R_{REF}$ as in the third modification, the detectable upper-limit temperature $T_{MAX}$ needs to be the upper-limit operating temperature $T_{upper}$, and the detectable lower-limit temperature $T_{MIN}$ needs to be the lower-limit operating temperature $T_{lower}$, as described in the first modification.

(Example of Detectable Temperature Range of Third Modification)

Figure 16:
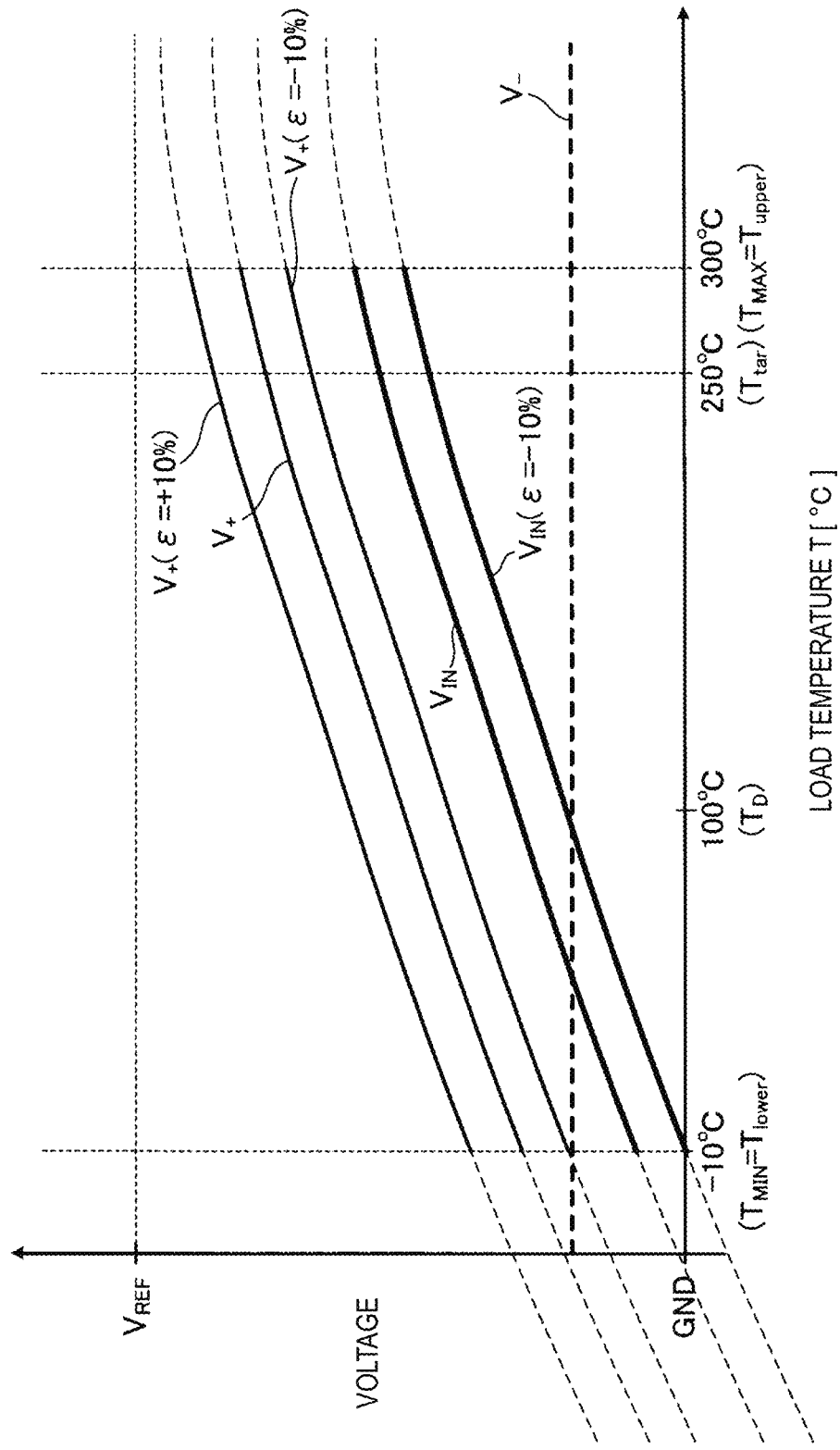
FIG. 16 is a graph showing a specific example of a detectable temperature range of the third modification of the aerosol inhaler shown in FIG. 1.

Here, an example of the detectable temperature range of the third modification will be described with reference to FIG. 16. The example shown in FIG. 16 is an example in which, since the upper-limit operating temperature $T_{upper}$ is 300° C. and the lower-limit operating temperature $T_{lower}$ is −10° C., the detectable temperature range is set to −10° C. to 300° C. by setting the detectable upper-limit temperature $T_{MAX}$ to 300° C. and the detectable lower-limit temperature $T_{MIN}$ to −10° C. In the example shown in FIG. 16, the threshold temperature $T_D$ is 100° C. as in the example shown in FIG. 14.

Similarly to FIG. 10, in FIG. 16, a vertical axis indicates the voltage $V_+$ input to the non-inverting input terminal 56a of the operational amplifier 56, the voltage $V_-$ input to the inverting input terminal 56b, and magnitude (that is, voltage) of the differential input $V_{IN}$, and a horizontal axis indicates the temperature T of the load 21.

As described in the first modification, in order to set the detectable temperature range to −10° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is −10° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). Specifically, for example, the electric resistance values $R_H$, $R_1$, $R_2$, and $R_3$ may be selected such that a difference between the $V_+$ and $V_-$ at the time when the temperature T of the load 21 is −10° C. (that is, the detectable lower-limit temperature $T_{MIN}$) is equal to the voltage of the ground GND (the minimum value that can be handled by the operational amplifier 56 when the operational amplifier 56 is the non-input/output rail-to-rail type).

Also in the third modification, it is preferable to consider the product error of the load 21. That is, for example, the electric resistance values $R_H$, $R_1$, $R_2$, and $R_3$ may be selected such that a difference between $V_+(\varepsilon=-10\%)$ and $V_-$ at the time when the temperature T of the load 21 is −10° C. (that is, the detectable lower-limit temperature $T_{MIN}$) is equal to the voltage of the ground GND (the minimum value that can be handled by the operational amplifier 56 when the operational amplifier 56 is the non-input/output rail-to-rail type) as shown in FIG. 16, and the aerosol inhaler 1 may be configured using the selected electric resistance values $R_H$, $R_1$, $R_2$, and $R_3$. In this way, even if the electric resistance value $R_H$ of the load 21 varies by 10% in a − direction from a reference value, the temperature T of the load 21 can be detected in the above detectable temperature range.

As described above, in the aerosol inhaler 1 of the third modification, in an operation guarantee temperature range in which the lower-limit operating temperature $T_{lower}$ is the least element and the upper-limit operating temperature $T_{upper}$ is the greatest element, the value obtained by multiplying, by the amplification factor A, the differential input or the difference value between the voltage input to the non-inverting input terminal 56a of the operational amplifier 56 and the voltage input to the inverting input terminal 56b is equal to or larger than the voltage of the negative power supply terminal 56e of the operational amplifier 56 (the minimum value or larger that can be handled by the operational amplifier 56 when the operational amplifier 56 is the non-input/output rail-to-rail type). Thus, when the temperature T of the load 21 is in the operation guarantee temperature range, the sticking of the differential input and the output signal, of the operational amplifier 56, can be suppressed. Therefore, it is possible to appropriately perform calibration for detecting the temperature T of the load 21.

(Fourth Modification of Aerosol Inhaler)

Next, a fourth modification of the aerosol inhaler 1 will be described. The fourth modification differs from the above-described embodiment in that the aerosol inhaler 1 ends a series of operations on condition that the temperature T of the load 21 is higher than the upper-limit operating temperature $T_{upper}$. In the following description of the fourth modification, the same parts as those in the above-described embodiment are denoted by the same reference signs, and descriptions thereof are omitted as appropriate.

(Example of Specific Operations of Aerosol Inhaler of Fourth Modification)

Figure 17:
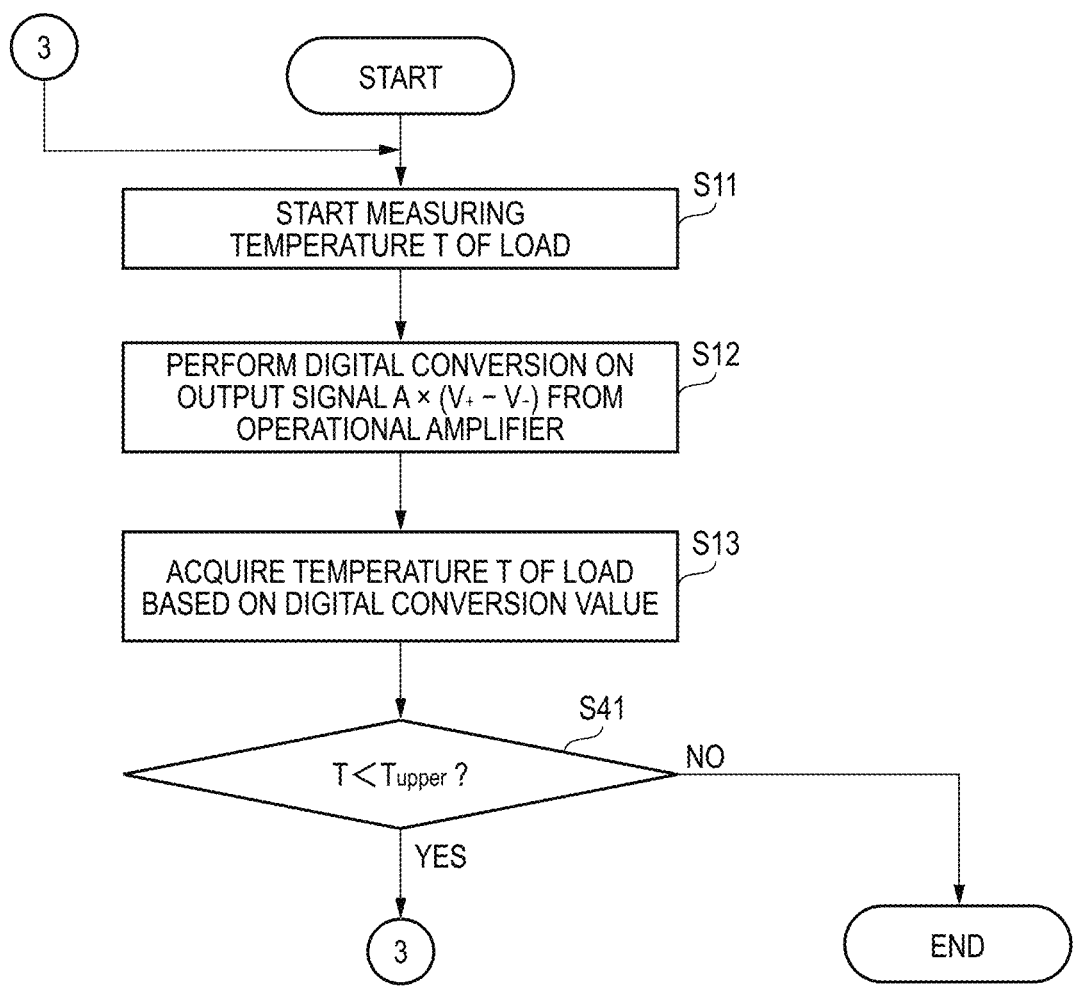
FIG. 17 is a flowchart showing an example of operations of a fourth modification of the aerosol inhaler shown in FIG. 1.

An example of specific operations of the aerosol inhaler 1 of the fourth modification will be described with reference to FIG. 17. As shown in FIG. 17, in the aerosol inhaler 1 of the fourth modification, after the operations of steps S11 to S13 are performed, an operation of step S41 is performed.

In step S41, the processor 55 of the MCU 50 determines whether the temperature T of the load 21 is lower than the upper-limit operating temperature $T_{upper}$ (that is, $T<T_{upper}$) based on the acquired temperature T of the load 21 and the upper-limit operating temperature $T_{upper}$. Information on the upper-limit operating temperature $T_{upper}$ is stored in advance in a ROM or the like (not shown).

When the processor 55 determines that the temperature T of the load 21 is lower than the upper-limit operating temperature $T_{upper}$ (step S41: YES), the processor 55 shifts to the operation of step S11. On the other hand, when the temperature T of the load 21 is determined to be equal to or higher than the upper-limit operating temperature $T_{upper}$ (step S41: NO), the processor 55 ends the series of operations shown in FIG. 17. That is, electricity discharge to the load 21 is prohibited thereafter.

As in the fourth modification, when the series of operations of the aerosol inhaler 1 is ended based on a comparison result between the temperature T of the load 21 and the upper-limit operating temperature $T_{upper}$, it is sufficient that the temperature T of the load 21 can be detected around the upper-limit operating temperature $T_{upper}$. Specifically, for example, if the temperature T of the load 21 can be detected in a temperature range of the upper-limit operating temperature $T_{upper}$–50° C. or higher and the upper-limit operating temperature $T_{upper}$ or lower, the series of operations can be ended with sufficient accuracy when the temperature T of the load 21 is the upper-limit operating temperature $T_{upper}$.

(Example of Detectable Temperature Range of Fourth Modification)

Here, an example of the detectable temperature range of the fourth modification will be described with reference to FIG. 18. The example shown in FIG. 18 is an example in which the detectable temperature range is set to 250° C. to 300° C. by setting the detectable upper-limit temperature $T_{MAX}$ to 300° C. as the upper-limit operating temperature $T_{upper}$ and the detectable lower-limit temperature $T_{MIN}$ to 250° C.

Figure 18:
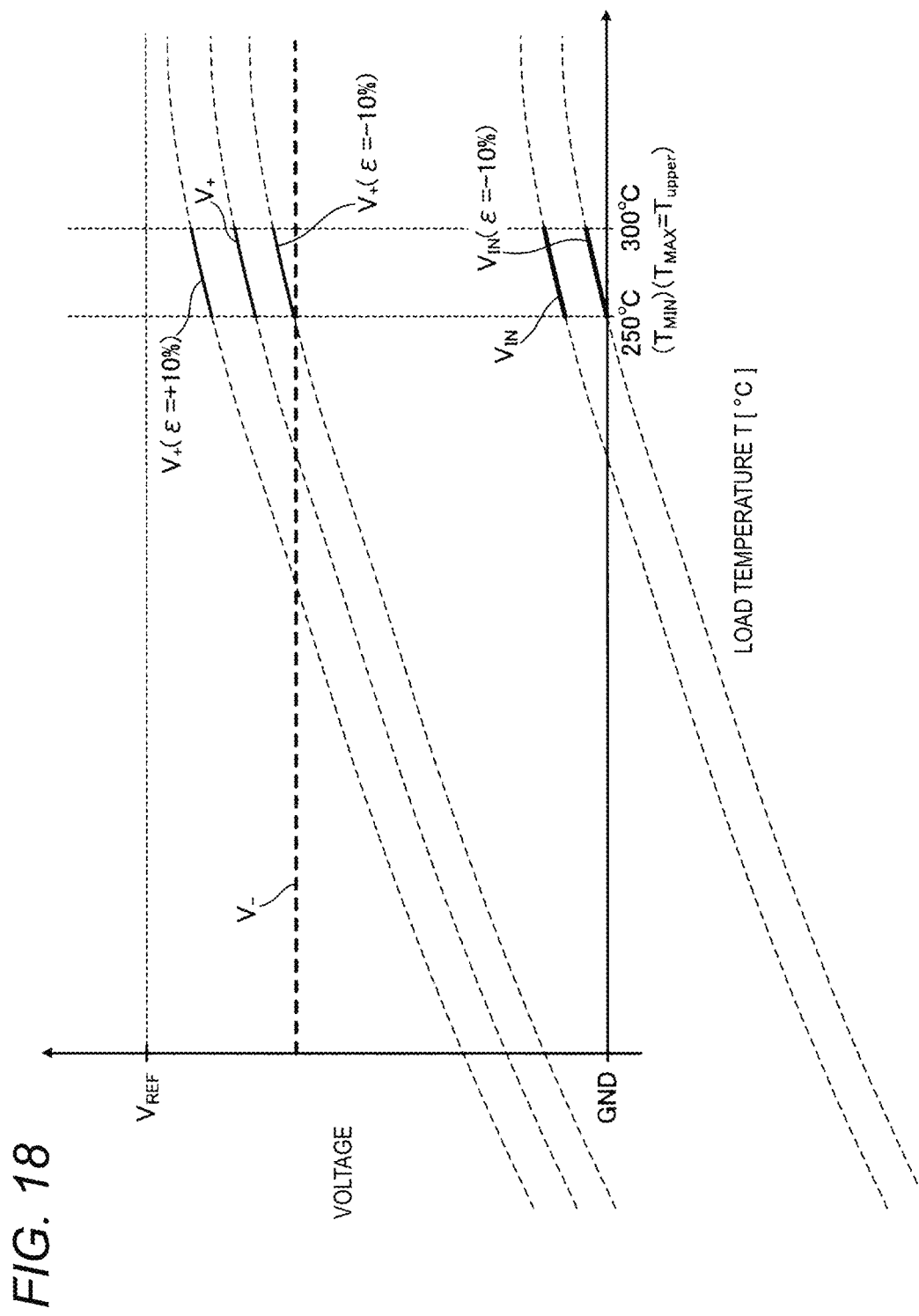
FIG. 18 is a graph showing a specific example of a detectable temperature range of the fourth modification of the aerosol inhaler shown in FIG. 1.

Similarly to FIG. 10, in FIG. 18, a vertical axis indicates the voltage $V_+$ input to the non-inverting input terminal 56a of the operational amplifier 56, the voltage $V_-$ input to the inverting input terminal 56b, and magnitude (that is, voltage) of the differential input $V_{IN}$, and a horizontal axis indicates the temperature T of the load 21.

In order to set the detectable temperature range to 250° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 250° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type).

That is, the manufacturer of the aerosol inhaler 1 may select the electric resistance values $R_H$, $R_1$, $R_2$, $R_3$ and the amplification factor A such that the value obtained by multiplying, by the amplification factor A, the differential input or the difference value between the voltage input to the non-inverting input terminal 56a and the voltage input to the inverting input terminal 56b when the temperature T of the load 21 is 250° C. to 300° C., is one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). The manufacturer of the aerosol inhaler 1 may configure the aerosol inhaler 1 using the selected electric resistance values $R_H$, $R_1$, $R_2$, $R_3$ and the amplification factor A.

More specifically, for example, the electric resistance values $R_H$, $R_1$, $R_2$, and $R_3$ may be selected such that a difference between the $V_+$ and $V_-$ at the time when the temperature T of the load 21 is 250° C. (that is, the detectable lower-limit temperature $T_{MIN}$) is equal to the voltage of the ground GND (the minimum value that can be handled by the operational amplifier 56 when the operational amplifier 56 is the non-input/output rail-to-rail type). In this way, when the temperature T of the load 21 is higher than 250° C., the differential input $V_{IN}$ of the operational amplifier 56 can be suppressed from sticking to the voltage of the ground GND.

Therefore, in the detectable temperature range of 250° C. or higher, the differential input $V_{IN}$ of the operational amplifier 56 can be reduced while suppressing the output signal $A \times V_{IN}$ of the operational amplifier 56 from sticking to the voltage of the ground GND and enabling detection of the temperature T of the load 21 based on the output signal of the operational amplifier 56.

Also in the fourth modification, it is preferable to consider the product error of the load 21. For example, the electric resistance values $R_H$, $R_1$, $R_2$, and $R_3$ may be selected such that a difference between a $V_+$ ($\varepsilon=-10\%$) and the $V_-$ at the time when the temperature T of the load 21 is 250° C. (that is the detectable lower-limit temperature $T_{MIN}$) is equal to the voltage of the ground GND (the minimum value that can be handled by the operational amplifier 56 when the operational amplifier 56 is the non-input/output rail-to-rail type) as shown in FIG. 18, and the aerosol inhaler 1 may be configured using the selected electric resistance values $R_H$, $R_1$, $R_2$, and $R_3$. In this case, the temperature T of the load 21 can be detected in the above-described detectable temperature range even when the electric resistance value $R_H$ of the load 21 varies by 10% in a – direction from a reference value.

As described above, in the aerosol inhaler 1 of the fourth modification, in a temperature range in which the upper-limit operating temperature $T_{upper}$ is included and a temperature of the upper-limit operating temperature $T_{upper}$–50° C. is the least element, the value obtained by multiplying, by the amplification factor A, the differential input or the difference value between the voltage input to the non-inverting input terminal 56a of the operational amplifier 56 and the voltage input to the inverting input terminal 56b is equal to or larger than the voltage of the negative power supply terminal 56e of the operational amplifier 56 (the minimum value or larger that can be handled by the operational amplifier 56 when the operational amplifier 56 is the non-input/output rail-to-rail type). Thus, when the temperature T of the load 21 is in the temperature range, the sticking of the differential input and the output signal, of the operational amplifier 56, can be suppressed. Therefore, when the temperature T of the load 21 is around the upper-limit operating temperature $T_{upper}$, it is possible to detect the temperature T of the load 21 with high accuracy, and to prevent the load 21 from being excessively heated.

(Fifth Modification of Aerosol Inhaler)

Next, a fifth modification of the aerosol inhaler 1 will be described. The fifth modification is different from the fourth modification in that calibration is performed on the reference temperature $T_{REF}$ and the reference electric resistance value $R_{REF}$ (see Formula (F0)). That is, the aerosol inhaler 1 of the fifth modification performs calibration on the reference temperature $T_{REF}$ and the reference electric resistance value $R_{REF}$ as in the first modification, and ends a series of operations on condition that the temperature T of the load 21 is higher than the upper-limit operating temperature $T_{upper}$ as in the fourth modification. In the following description of the fifth modification, the same reference signs are given to the same parts as those in the first and fourth modifications, and descriptions thereof are omitted as appropriate.

(Example of Specific Operations of Aerosol Inhaler of Fifth Modification)

Figure 19:
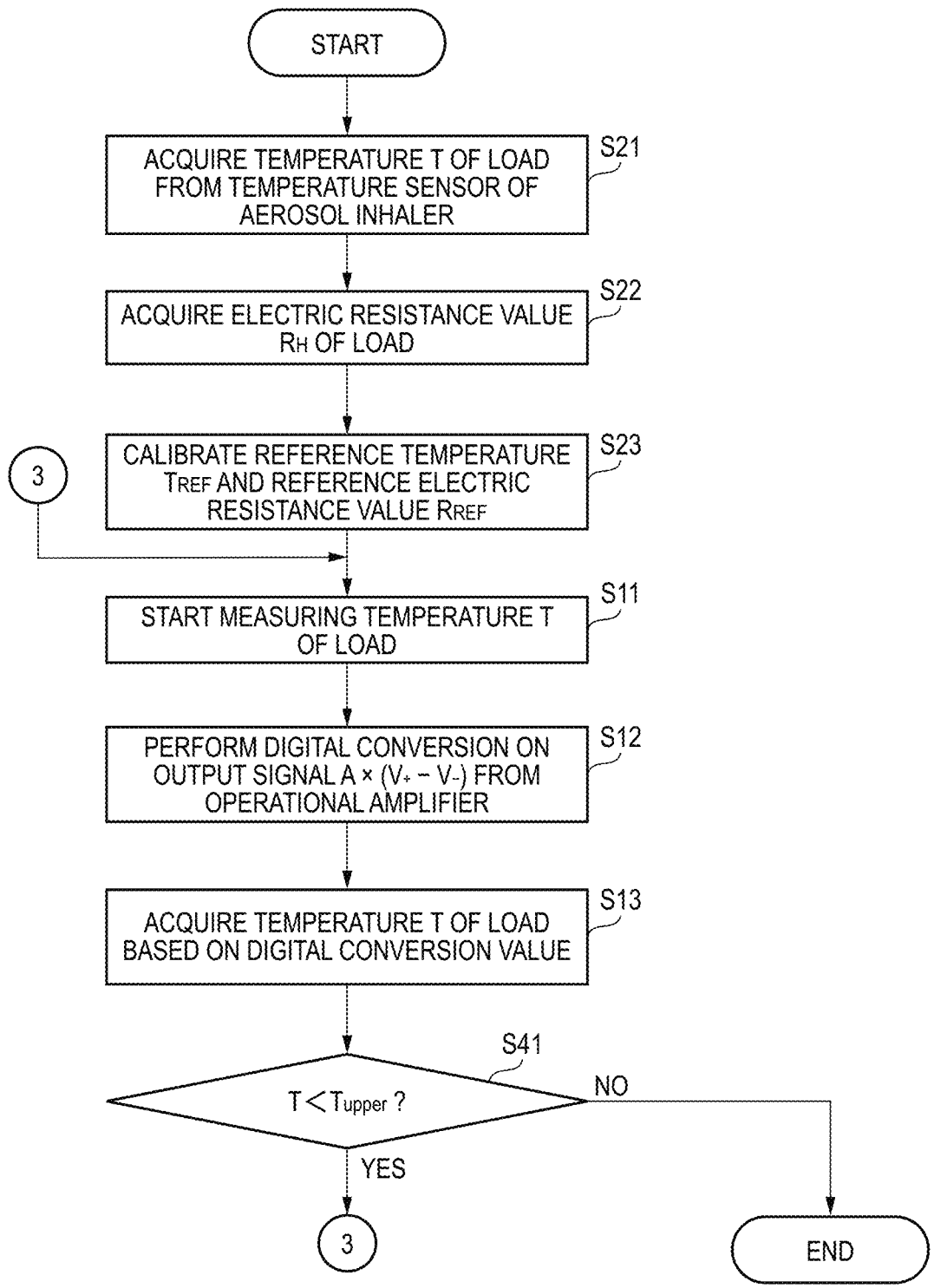
FIG. 19 is a flowchart showing an example of operations of a fifth modification of the aerosol inhaler shown in FIG. 1.

An example of specific operations of the aerosol inhaler 1 of the fifth modification will be described with reference to FIG. 19. As shown in FIG. 19, in the aerosol inhaler 1 of the fifth modification, after the operations of steps S21 to S23 are performed, the operations of steps S11 to S13 and step S41 are performed.

When the calibration is performed on the reference temperature $T_{REF}$ and the reference electric resistance value $R_{REF}$ as in the fifth modification, the detectable upper-limit temperature $T_{MAX}$ needs to be the upper-limit operating temperature $T_{upper}$, and the detectable lower-limit temperature $T_{MIN}$ needs to be the lower-limit operating temperature $T_{lower}$, as described in the first modification.

(Example of Detectable Temperature Range of Fifth Modification)

Here, an example of the detectable temperature range of the fifth modification will be described with reference to FIG. 20. The example shown in FIG. 20 is an example in which, since the upper-limit operating temperature $T_{upper}$ is 300° C. and the lower-limit operating temperature $T_{lower}$ is −10° C., the detectable temperature range is set to −10° C. to 300° C. by setting the detectable upper-limit temperature $T_{MAX}$ to 300° C. and the detectable lower-limit temperature $T_{MIN}$ to −10° C.

Figure 20:
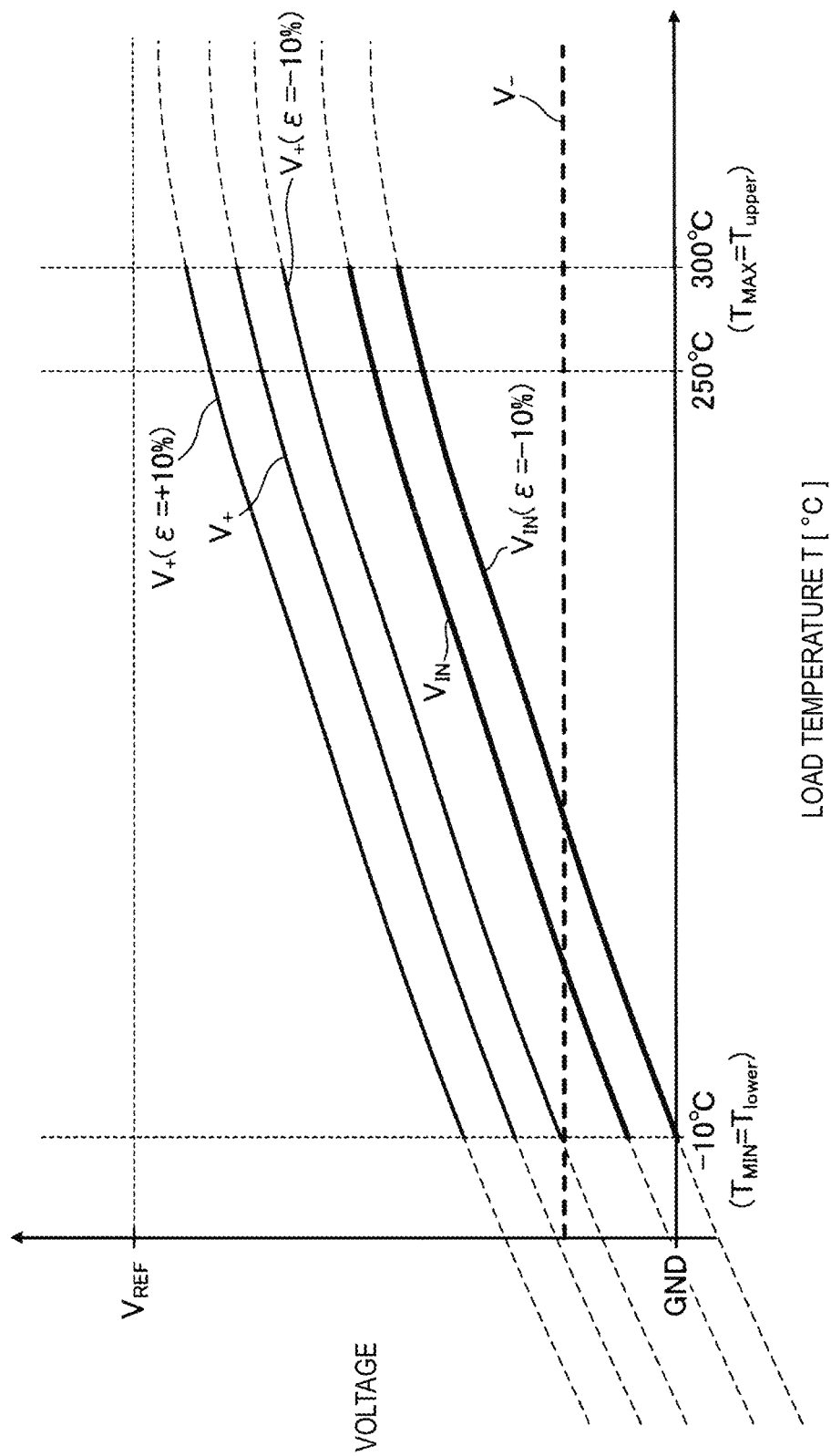
FIG. 20 is a graph showing a specific example of a detectable temperature range of the fifth modification of the aerosol inhaler shown in FIG. 1.

Similarly to FIG. 10, in FIG. 20, a vertical axis indicates the voltage $V_+$ input to the non-inverting input terminal 56a of the operational amplifier 56, the voltage $V_-$ input to the inverting input terminal 56b, and magnitude (that is, voltage) of the differential input $V_{IN}$, and a horizontal axis indicates the temperature T of the load 21.

As described in the first modification, in order to set the detectable temperature range to −10° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is −10° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). Specifically, for example, the electric resistance values $R_H$, $R_1$, $R_2$, and $R_3$ may be selected such that a difference between the $V_+$ and $V_-$ at the time when the temperature T of the load 21 is −10° C. (that is, the detectable lower-limit temperature $T_{MIN}$) is equal to the voltage of the ground GND (the minimum value that can be handled by the operational amplifier 56 when the operational amplifier 56 is the non-input/output rail-to-rail type).

Also in the fifth modification, it is preferable to consider the product error of the load 21. That is, for example, the electric resistance values $R_H$, $R_1$, $R_2$, and $R_3$ may be selected such that a difference between $V_+(\varepsilon=-10\%)$ and $V_-$ at the time when the temperature T of the load 21 is −10° C. (that is, the detectable lower-limit temperature $T_{MIN}$) is equal to the voltage of the ground GND (the minimum value that can be handled by the operational amplifier 56 when the operational amplifier 56 is the non-input/output rail-to-rail type) as shown in FIG. 20, and the aerosol inhaler 1 may be configured using the selected electric resistance values $R_H$, $R_1$, $R_2$, and $R_3$. In this way, even if the electric resistance value $R_H$ of the load 21 varies by 10% in a − direction from a reference value, the temperature T of the load 21 can be detected in the above detectable temperature range.

As described above, in the aerosol inhaler 1 of the fifth modification, in an operation guarantee temperature range in which the lower-limit operating temperature $T_{lower}$ is the least element and the upper-limit operating temperature $T_{upper}$ is the greatest element, the value obtained by multiplying, by the amplification factor A, the differential input or the difference value between the voltage input to the non-inverting input terminal 56a of the operational amplifier 56 and the voltage input to the inverting input terminal 56b is larger than the voltage of the negative power supply terminal 56e of the operational amplifier 56 (the minimum value that can be handled by the operational amplifier 56 when the operational amplifier 56 is the non-input/output rail-to-rail type). Thus, when the temperature T of the load 21 is in the operation guarantee temperature range, the sticking of the differential input or the output signal, of the operational amplifier 56, can be suppressed. Therefore, it is possible to appropriately perform calibration for detecting the temperature T of the load 21.

(Sixth Modification of Aerosol Inhaler)

Figure 21:
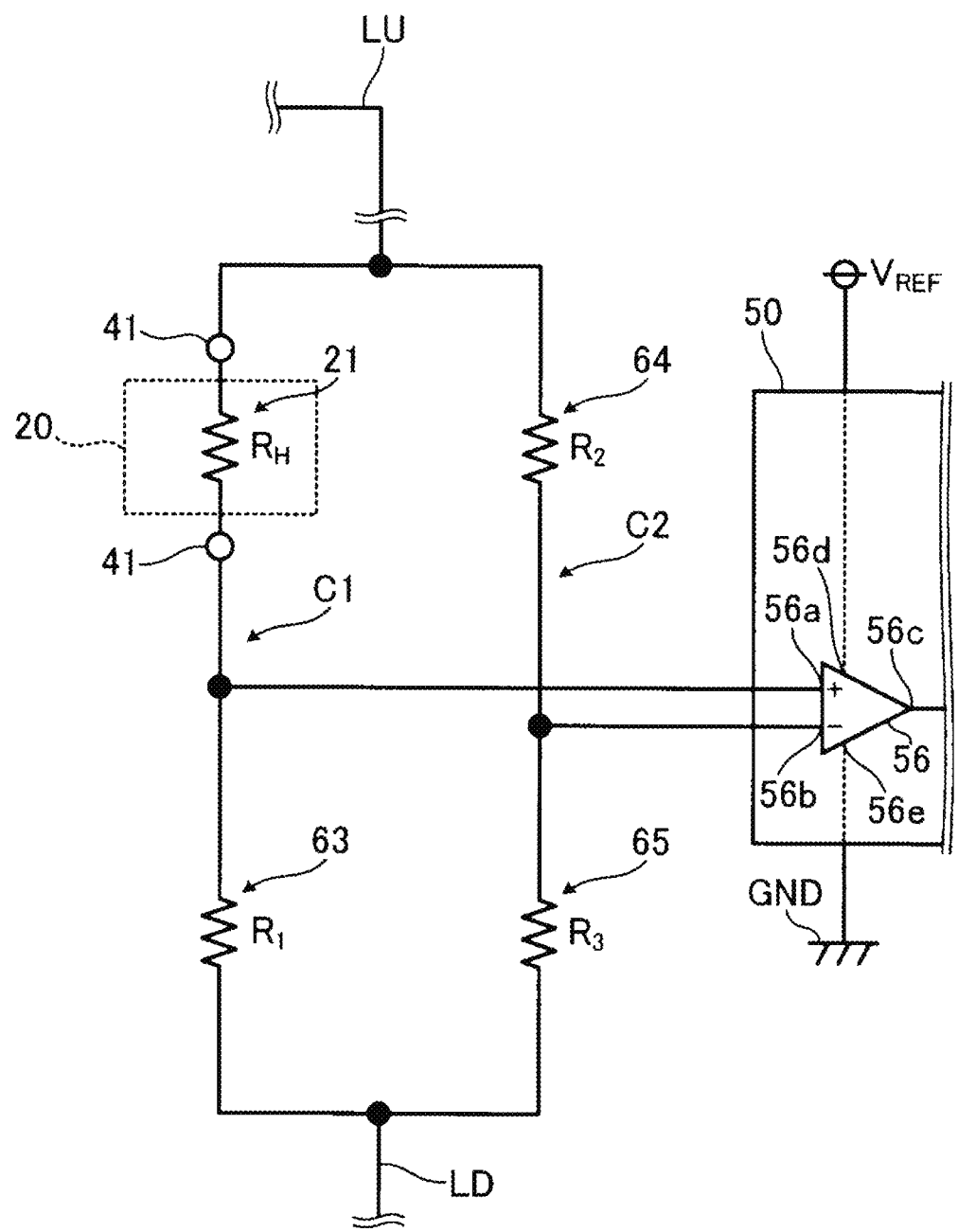
FIG. 21 is a diagram showing a main part of a circuit configuration of a power supply unit of a sixth modification of the aerosol inhaler shown in FIG. 1.

Next, a sixth modification of the aerosol inhaler 1 will be described. The sixth modification is different from the above-described embodiment in that, as shown in FIG. 21, the first element 63 is an element on a low potential side of the first series circuit C1, and the load 21 is an element on a high potential side of the first series circuit C1. In the following description of the sixth modification, the same parts as those in the above-described embodiment are denoted by the same reference signs, and descriptions thereof are omitted as appropriate.

In the sixth modification, the voltage $V_+$ input to the non-inverting input terminal 56a of the operational amplifier 56 is expressed by the following Formula (F8), with a voltage (in other words, a potential difference between the main positive bus LU and the main negative bus LD) applied to the entire parallel circuit formed of the first series circuit C1 and the second series circuit C2 being taken as "V".

$$V_+ = \frac{R_1}{R_1 + R_H} \cdot V \quad (F8)$$

In the sixth modification, the voltage $V_-$ input to the inverting input terminal 56b of the operational amplifier 56 is expressed by the above Formula (F2) as in the above-described embodiment. Therefore, in the sixth modification, the differential input $V_{IN}$ of the operational amplifier 56 is expressed by the following Formula (F9).

$$V_{IN} = V_+ - V_- = \frac{R_1}{R_1 + R_H} \cdot V - \frac{R_3}{R_2 + R_3} \cdot V \quad (F9)$$

(Example of Detectable Temperature Range of Sixth Modification)

Next, an example of the detectable temperature range of the sixth modification will be described with reference to FIG. 22. For example, the aerosol inhaler 1 according to the sixth modification performs control to end a series of operations on condition that the temperature T of the load 21 is higher than the upper-limit operating temperature $T_{upper}$, as in the fourth modification. Accordingly, in FIG. 22, an example in which the detectable temperature range is set to 250° C. to 300° C. by setting the detectable lower-limit temperature $T_{MIN}$ to 250° C. and the detectable upper-limit temperature $T_{MAX}$ to 300° C. will be described.

Figure 22:
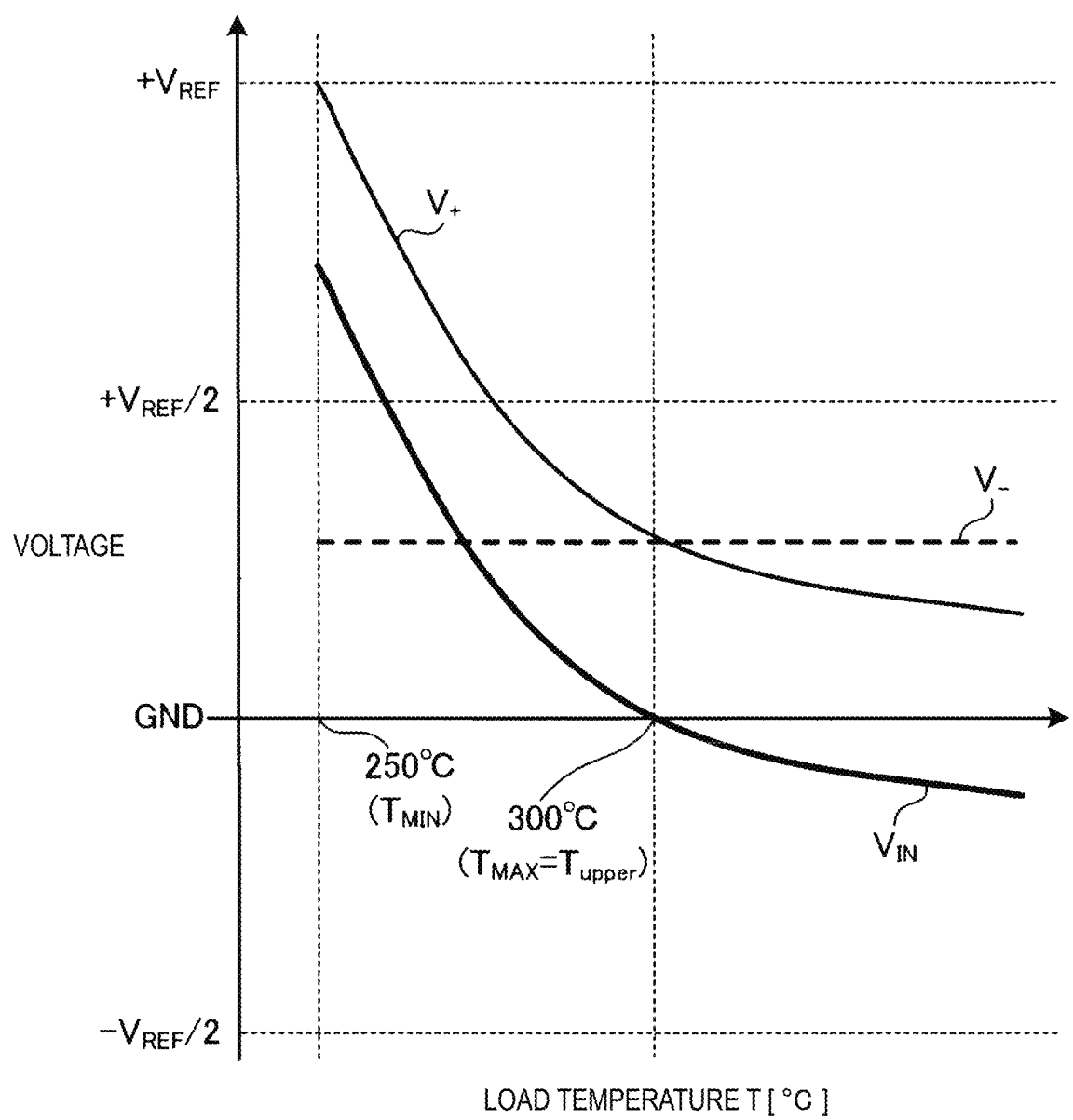
FIG. 22 is a graph showing a specific example of a detectable temperature range of the sixth modification of the aerosol inhaler shown in FIG. 1.

Similarly to FIG. 10, in FIG. 22, a vertical axis indicates the voltage $V_+$ input to the non-inverting input terminal 56a of the operational amplifier 56, the voltage $V_-$ input to the inverting input terminal 56b, and magnitude (that is, voltage) of the differential input $V_{IN}$, and a horizontal axis indicates the temperature T of the load 21.

As described above, since the load 21 has the PTC characteristic, the electric resistance value $R_H$ of the load 21 increases as the temperature T of the load 21 increases. Therefore, in the case of the sixth modification, the voltage $V_+$ input to the non-inverting input terminal 56a of the operational amplifier 56 in a case where the voltage V is applied to the entire parallel circuit formed of the first series circuit C1 and the second series circuit C2 decreases as the temperature T of the load 21 increases as shown in FIG. 22 (see also the above Formula (F8)).

On the other hand, in the sixth modification, the voltage $V_-$ input to the inverting input terminal 56b of the operational amplifier 56 in the case where the voltage V is applied to the entire parallel circuit formed of the first series circuit C1 and the second series circuit C2 has a constant value regardless of the temperature T of the load 21, as shown in FIG. 22 (see also the above Formula (F2)).

As described in the fourth modification, in order to set the detectable temperature range to 250° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 250° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). More specifically, in the case of the sixth modification, the electric resistance values $R_H$, $R_1$, $R_2$, and $R_3$ may be selected such that a difference between the $V_+$ and $V_-$ at the time when the temperature T of the load 21 is 300° C. (that is, the detectable upper-limit temperature $T_{MAX}$) is equal to the voltage of the ground GND (the minimum value that can be handled by the operational amplifier 56 when the operational amplifier 56 is the non-input/output rail-to-rail type).

In this way, when the temperature T of the load 21 is lower than 300° C., the differential input $V_{IN}$ of the operational amplifier 56 can be prevented from sticking to the voltage of the ground GND or the minimum value that can be handled by the operational amplifier 56.

It is also preferable to consider a product error of the load 21 in the sixth modification although a detailed description and illustration thereof are omitted here. That is, in the case of the sixth modification, for example, the electric resistance values $R_H$, $R_1$, $R_2$, and $R_3$ may be selected such that a difference value between the voltage $V_+(\varepsilon=+10\%)$ input to the non-inverting input terminal 56a of the operational amplifier 56 and the voltage input to the inverting input terminal 56b at the time when the temperature T of the load 21 is 300° C., is equal to the voltage of the ground GND connected to the negative power supply terminal 56e (the minimum value that can be handled by the operational amplifier 56 when the operational amplifier 56 is the non-input/output rail-to-rail type).

As described above, in the aerosol inhaler 1 of the sixth modification, in a temperature range in which the upper-limit operating temperature $T_{upper}$ is included and a temperature of the upper-limit operating temperature $T_{upper}$–50° C. is the least element, the value obtained by multiplying, by the amplification factor A, the differential input or the difference value between the voltage input to the non-inverting input terminal 56a of the operational amplifier 56 and the voltage input to the inverting input terminal 56b is larger than the voltage of the negative power supply terminal 56e of the operational amplifier 56 (the minimum value that can be handled by the operational amplifier 56 when the operational amplifier 56 is the non-input/output rail-to-rail type). Thus, when the temperature T of the load 21 is in the temperature range, the sticking of the differential input and the output signal, of the operational amplifier 56, can be suppressed. Therefore, when the temperature T of the load 21 is around the upper-limit operating temperature $T_{upper}$, it is possible to detect the temperature T of the load 21 with high accuracy, and to prevent the load 21 from being excessively heated.

(Seventh Modification of Aerosol Inhaler)

Figure 23:
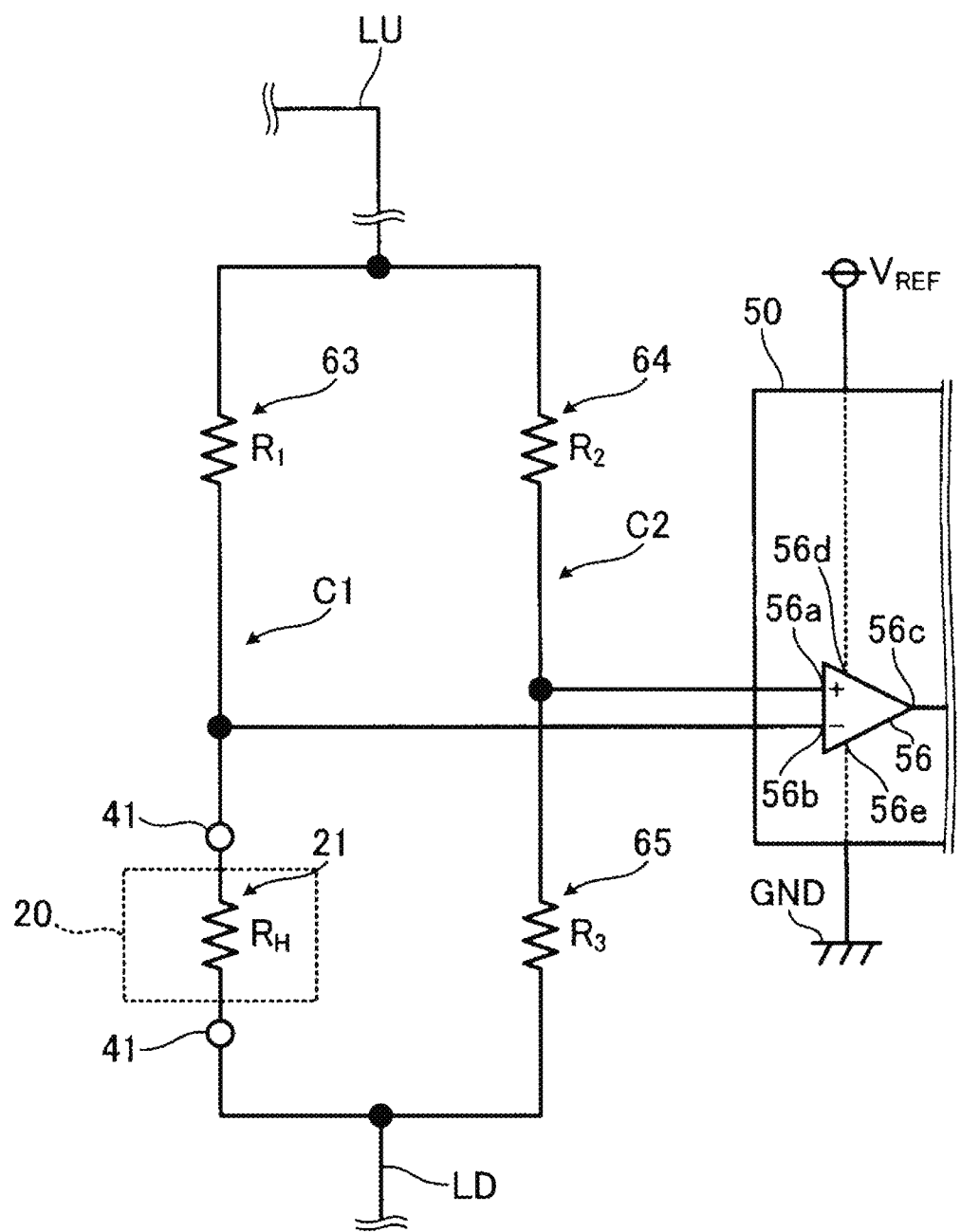
FIG. 23 is a diagram showing a main part of a circuit configuration of a power supply unit of a seventh modification of the aerosol inhaler shown in FIG. 1.

Next, a seventh modification of the aerosol inhaler 1 will be described. The seventh modification is different from the above-described embodiment in that the second series circuit C2 is connected to the non-inverting input terminal 56a of the operational amplifier 56, and the first series circuit C1 is connected to the inverting input terminal 56b of the operational amplifier 56, as shown in FIG. 23. In the following description of the seventh modification, the same parts as those in the above-described embodiment are denoted by the same reference signs, and descriptions thereof are omitted as appropriate.

In the seventh modification, the voltage $V_+$ input to the non-inverting input terminal 56a of the operational amplifier 56 is the same as the voltage $V_-$ in the above-described embodiment. Further, in the seventh modification, the voltage $V_-$ input to the inverting input terminal 56b of the operational amplifier 56 is the same as the voltage $V_+$ in the above-described embodiment. Accordingly, in the seventh modification, the differential input $V_{IN}$ of the operational amplifier 56 is expressed by the following Formula (F10).

$$V_+ - V_- = \frac{R_2}{R_2 + R_3} \cdot V - \frac{R_H}{R_1 + R_H} \cdot V \tag{F10}$$

(Example of Detectable Temperature Range of Seventh Modification)

Next, an example of the detectable temperature range of the seventh modification will be described with reference to FIG. 24. For example, the aerosol inhaler 1 according to the seventh modification performs control to end a series of operations on condition that the temperature T of the load 21 is higher than the upper-limit operating temperature $T_{upper}$, as in the fourth modification. Accordingly, in FIG. 24, an example in which the detectable temperature range is set to 250° C. to 300° C. by setting the detectable lower-limit temperature $T_{MIN}$ to 250° C. and the detectable upper-limit temperature $T_{MAX}$ to 300° C. will be described.

Figure 24:
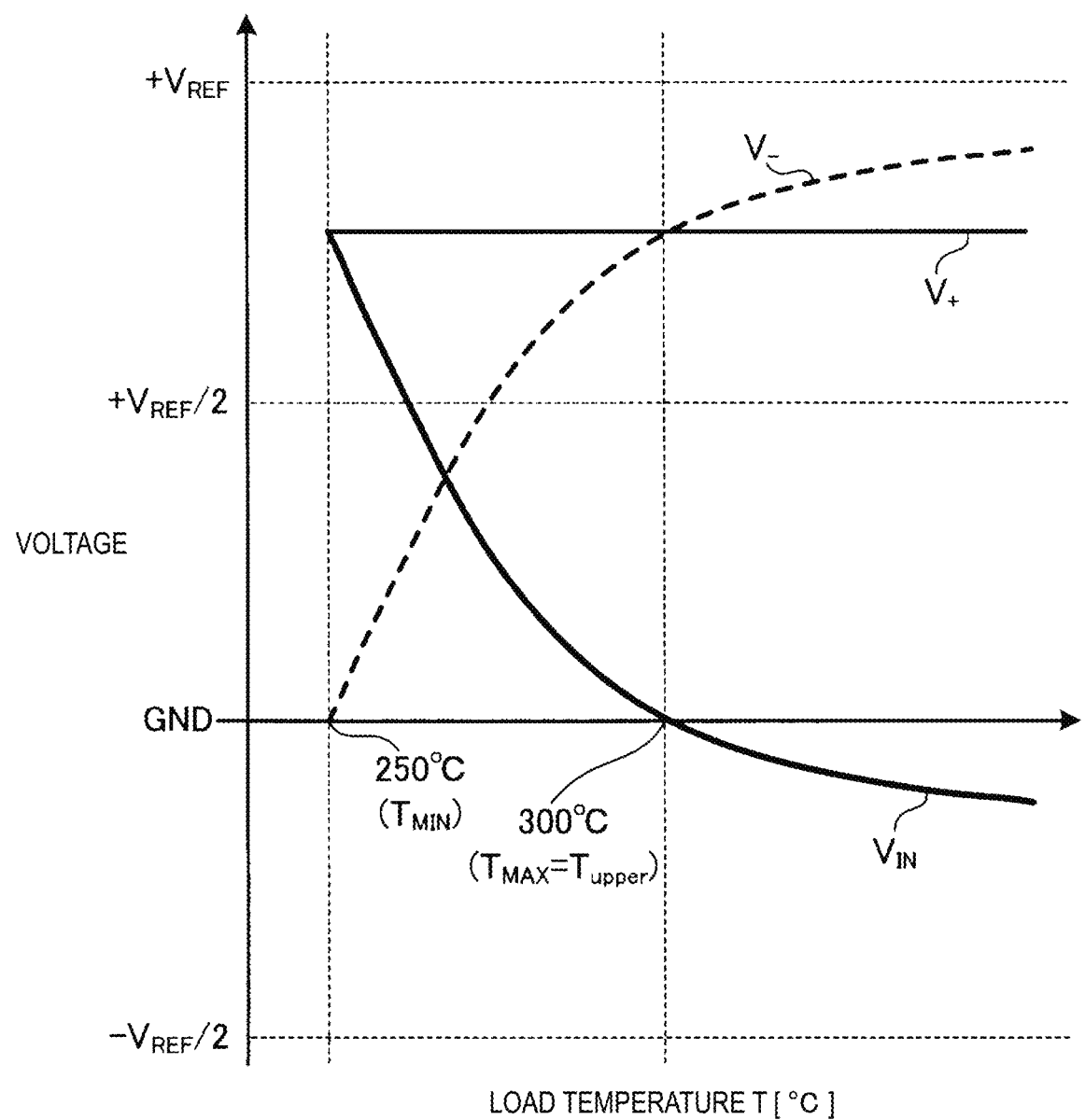
FIG. 24 is a graph showing a specific example of a detectable temperature range of the seventh modification of the aerosol inhaler shown in FIG. 1.

Similarly to FIG. 10, in FIG. 24, a vertical axis indicates the voltage $V_+$ input to the non-inverting input terminal 56a of the operational amplifier 56, the voltage $V_-$ input to the inverting input terminal 56b, and magnitude (that is, voltage) of the differential input $V_{IN}$, and a horizontal axis indicates the temperature T of the load 21.

In the seventh modification, the voltage $V_+$ input to the non-inverting input terminal 56a of the operational amplifier 56 in a case where the voltage V is applied to the entire parallel circuit formed of the first series circuit C1 and the second series circuit C2 has a constant value regardless of the temperature T of the load 21, as shown in FIG. 24.

On the other hand, in the seventh modification, the voltage $V_-$ input to the inverting input terminal 56b of the operational amplifier 56 in a case where the voltage V is applied to the entire parallel circuit formed by the first series circuit C1 and the second series circuit C2 increases as the temperature T of the load 21 increases, as shown in FIG. 24.

As described in the fourth modification, in order to set the detectable temperature range to 250° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 250° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). More specifically, in the case of the seventh modification, the electric resistance values $R_H$, $R_1$, $R_2$, and $R_3$ may be selected such that a difference between the $V_+$ and $V_-$ at the time when the temperature T of the load 21 is 300° C. (that is, the detectable upper-limit temperature $T_{MAX}$) is equal to the voltage of the ground GND (the minimum value that can be handled by the operational amplifier 56 when the operational amplifier 56 is the non-input/output rail-to-rail type).

In this way, when the temperature T of the load 21 is lower than 300° C., the differential input $V_{IN}$ of the operational amplifier 56 can be prevented from sticking to the voltage of the ground GND (the minimum value that can be handled by the operational amplifier 56 when the operational amplifier 56 is the non-input/output rail-to-rail type).

It is also preferable to consider a product error of the load 21 in the seventh modification although a detailed description and illustration thereof are omitted here. That is, in the case of the seventh modification, for example, the electric resistance values $R_H$, $R_1$, $R_2$, and $R_3$ may be selected such that a difference value between the voltage input to the non-inverting input terminal 56a of the operational amplifier 56 and a voltage $V_-$ ($\varepsilon=+10\%$) input to the inverting input terminal 56b at the time when the temperature T of the load 21 is 300° C., is equal to the voltage of the ground GND connected to the negative power supply terminal 56e (the minimum value that can be handled by the operational amplifier 56 when the operational amplifier 56 is the non-input/output rail-to-rail type).

As described above, in the aerosol inhaler 1 of the seventh modification, in a temperature range in which the upper-limit operating temperature $T_{upper}$ is included and a temperature of the upper-limit operating temperature $T_{upper}$−50° C. is the least element, the value obtained by multiplying, by the amplification factor A, the differential input or the difference value between the voltage input to the non-inverting input terminal 56a of the operational amplifier 56 and the voltage input to the inverting input terminal 56b is equal to or larger than the voltage of the negative power supply terminal 56e of the operational amplifier 56 (the minimum value or larger that can be handled by the operational amplifier 56 when the operational amplifier 56 is the non-input/output rail-to-rail type). Thus, when the temperature T of the load 21 is in the temperature range, the sticking of the differential input and the output signal, of the operational amplifier 56, can be suppressed. Therefore, when the temperature T of the load 21 is around the upper-limit operating temperature $T_{upper}$, it is possible to detect the temperature T of the load 21 with high accuracy, and to prevent the load 21 from being excessively heated.

(Eighth Modification of Aerosol Inhaler)

Figure 25:
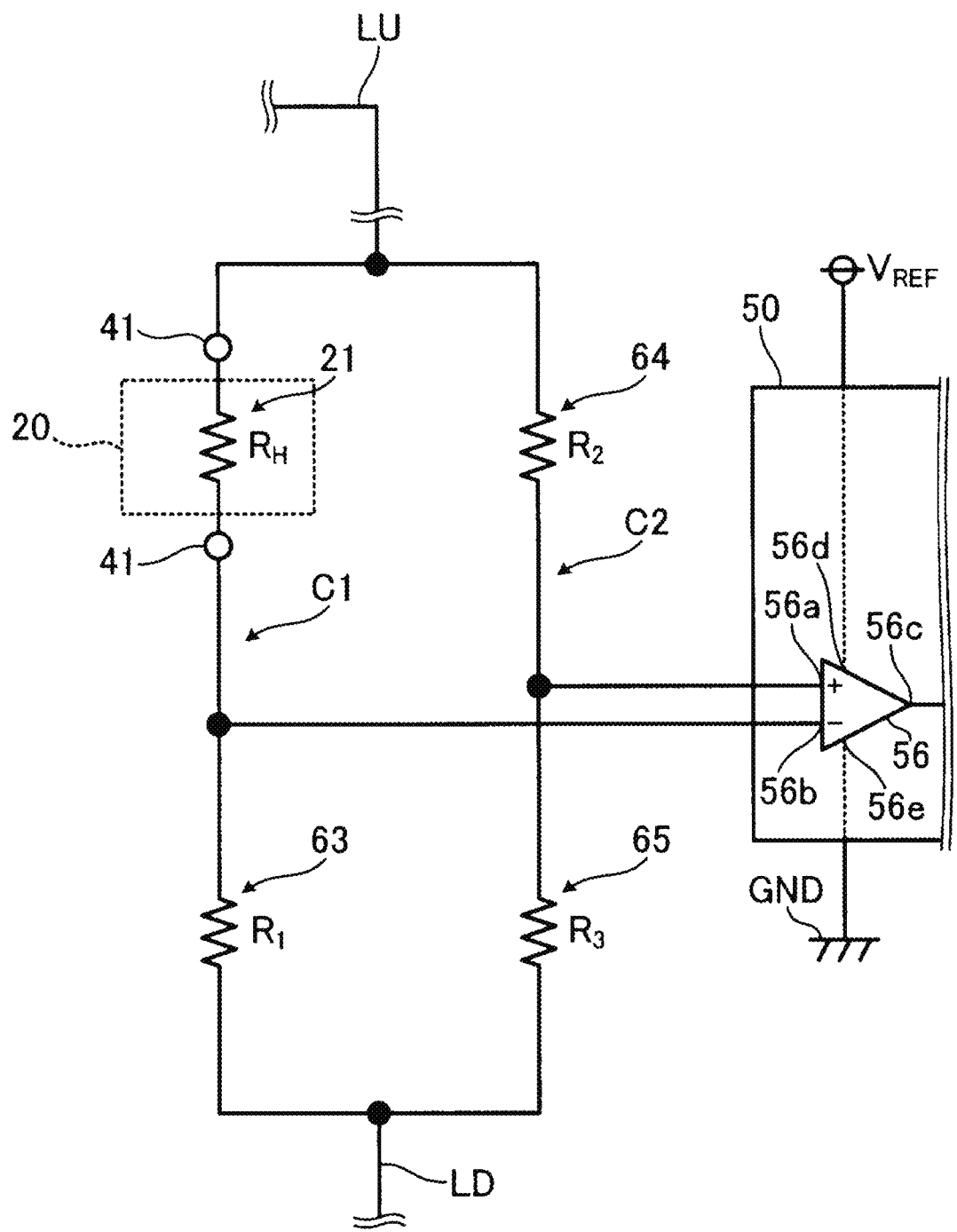
FIG. 25 is a diagram showing a main part of a circuit configuration of a power supply unit of an eighth modification of the aerosol inhaler shown in FIG. 1.

Next, an eighth modification of the aerosol inhaler 1 will be described. The eighth modification is different from the above-described embodiment in that, as shown in FIG. 25, the first element 63 is an element on a low potential side of the first series circuit C1 and the load 21 is an element on a high potential side of first series circuit C1, and that the second series circuit C2 is connected to the non-inverting input terminal 56a of the operational amplifier 56 and the first series circuit C1 is connected to the inverting input terminal 56b of the operational amplifier 56. In the following description of the eighth modification, the same reference signs are given to the same parts as those in the above-described embodiment, and descriptions thereof are omitted as appropriate.

In the eighth modification, the differential input $V_{IN}$ of the operational amplifier 56 is expressed by the following Formula (F11).

$$V_+ - V_- = \frac{R_2}{R_2 + R_3} \cdot V - \frac{R_1}{R_1 + R_H} \cdot V \tag{F11}$$

(Example of Detectable Temperature Range of Eighth Modification)

Next, an example of the detectable temperature range of the eighth modification will be described with reference to FIG. 26. For example, the aerosol inhaler 1 according to the eighth modification performs control to end a series of operations on condition that the temperature T of the load 21 is higher than the upper-limit operating temperature $T_{upper}$, as in the fourth modification. Accordingly, in FIG. 24, an example in which the detectable temperature range is set to 250° C. to 300° C. by setting the detectable lower-limit temperature $T_{MIN}$ to 250° C. and the detectable upper-limit temperature $T_{MAX}$ to 300° C. will be described.

Figure 26:
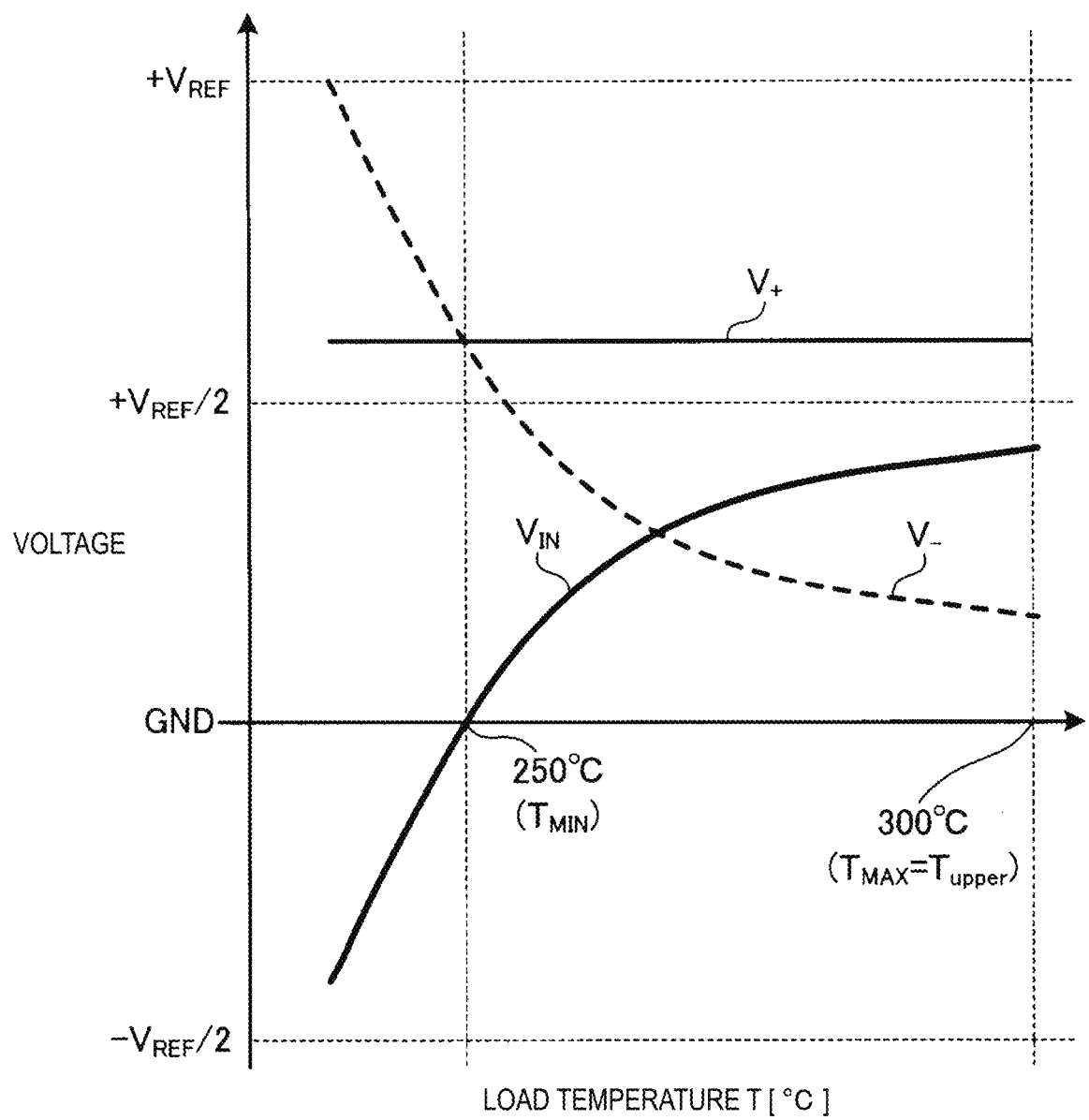
FIG. 26 is a graph showing a specific example of a detectable temperature range of the eighth modification of the aerosol inhaler shown in FIG. 1.

Similarly to FIG. 10, in FIG. 26, a vertical axis indicates the voltage $V_+$ input to the non-inverting input terminal 56a of the operational amplifier 56, the voltage $V_-$ input to the inverting input terminal 56b, and magnitude (that is, voltage) of the differential input $V_{IN}$, and a horizontal axis indicates the temperature T of the load 21.

In the eighth modification, the voltage $V_+$ input to the non-inverting input terminal 56a of the operational amplifier 56 in a case where the voltage V is applied to the entire parallel circuit formed of the first series circuit C1 and the second series circuit C2 has a constant value regardless of the temperature T of the load 21, as shown in FIG. 26.

On the other hand, in the eighth modification, the voltage $V_-$ input to the inverting input terminal 56b of the operational amplifier 56 when the voltage V is applied to the entire parallel circuit formed by the first series circuit C1 and the second series circuit C2 decreases as the temperature T of the load 21 increases as shown in FIG. 24.

As described in the fourth modification, in order to set the detectable temperature range to 250° C. to 300° C., a value obtained by multiplying, by the amplification factor A, the differential input or the difference value between the voltage input to the non-inverting input terminal 56a of the operational amplifier 56 and the voltage input to the inverting input terminal 56b when the temperature T of the load 21 is 250° C. to 300° C., may be one corresponding to the voltage of the ground GND or larger (the minimum value or larger that can be handled by the operational amplifier 56 when the operational amplifier 56 is the non-input/output rail-to-rail type) and the reference voltage $V_{REF}$ or smaller (the maximum value or smaller that can be handled by the operational amplifier 56 when the operational amplifier 56 is the non-input/output rail-to-rail type). More specifically, in the case of the eighth modification, the electric resistance values $R_H$, $R_1$, $R_2$, and $R_3$ may be selected such that a difference between the $V_+$ and $V_-$ at the time when the temperature T of the load 21 is 300° C. (that is, the detectable upper-limit temperature $T_{MAX}$) is equal to the voltage of the ground GND (the minimum value that can be handled by the operational amplifier 56 when the operational amplifier 56 is the non-input/output rail-to-rail type).

In this way, when the temperature T of the load 21 is lower than 300° C., the differential input $V_{IN}$ of the operational amplifier 56 can be prevented from sticking to the voltage of the ground GND (the minimum value that can be handled by the operational amplifier 56 when the operational amplifier 56 is the non-input/output rail-to-rail type).

It is also preferable to consider a product error of the load 21 in the eighth modification although a detailed description and illustration thereof are omitted here. That is, in the case of the eighth modification, for example, the electric resistance values $R_H$, $R_1$, $R_2$, and $R_3$ may be selected such that a difference value between the voltage input to the non-inverting input terminal 56a of the operational amplifier 56 and a voltage $V_-$ ($\varepsilon = -10\%$) input to the inverting input terminal 56b at the time when the temperature T of the load 21 is 300° C., is equal to the voltage of the ground GND connected to the negative power supply terminal 56e (the minimum value that can be handled by the operational amplifier 56 when the operational amplifier 56 is the non-input/output rail-to-rail type).

As described above, in the aerosol inhaler 1 of the eighth modification, in a temperature range in which the upper-limit operating temperature $T_{upper}$ is included and a temperature of the upper-limit operating temperature $T_{upper}-50°$ C. is the least element, the value obtained by multiplying, by the amplification factor A, the differential input or the difference value between the voltage input to the non-inverting input terminal 56a of the operational amplifier 56 and the voltage input to the inverting input terminal 56b is larger than the voltage of the negative power supply terminal 56e of the operational amplifier 56 (the minimum value that can be handled by the operational amplifier 56 when the operational amplifier 56 is the non-input/output rail-to-rail type). Thus, when the temperature T of the load 21 is in the temperature range, the sticking of the differential input and the output signal, of the operational amplifier 56, can be suppressed. Therefore, when the temperature T of the load 21 is around the upper-limit operating temperature $T_{upper}$, it is possible to detect the temperature T of the load 21 with high accuracy, and to prevent the load 21 from being excessively heated.

The present invention is not limited to the embodiment and the modifications described above, and modifications, improvements, and the like can be made as appropriate.

For example, in the embodiment and the modifications described above, examples are described in which the operation guarantee temperature range of the load 21 is set to a temperature range of being equal to or higher than the lower-limit operating temperature $T_{lower}$ and equal to or lower than the upper-limit operating temperature $T_{upper}$, but the present invention is not limited thereto. For example, the operation guarantee temperature range of the load 21 may be set to a temperature range higher than the lower-limit operating temperature $T_{lower}$ and lower than the upper-limit operating temperature $T_{upper}$.

That is, the lower-limit operating temperature $T_{lower}$ is set as a lower limit of the operation guarantee temperature range of the load 21 (which is not included in the operation guarantee temperature range of the load 21 and is the greatest element among temperatures included in the above-described lower-bound temperature), and the upper-limit operating temperature $T_{upper}$ may be set as an upper limit of the operation guarantee temperature range of the load 21 (which is not included in the operation guarantee temperature range and is the least element among temperatures included in the above-described upper-bound temperature).

Similarly, in the embodiment and the modifications described above, examples are described in which the detectable temperature range is a temperature range of the detectable lower-limit temperature $T_{MIN}$ or higher and the detectable upper-limit temperature $T_{MAX}$ or lower, but the present invention is not limited thereto. For example, the detectable temperature range may be a temperature range higher than the detectable lower-limit temperature $T_{MIN}$ and lower than the detectable upper-limit temperature $T_{MAX}$. That is, the detectable lower-limit temperature $T_{MIN}$ may be a lower limit of the detectable temperature range, and the detectable upper-limit temperature $T_{MAX}$ may be an upper limit of the detectable temperature range.

Although the first cartridge 20 including the load 21 is detachably attached to the power supply unit 10 in the embodiment and the modifications described above, the first cartridge 20 including the load 21 may also be integrated with the power supply unit 10.

The present specification at least describes the following matters. It should be noted that although corresponding components in the above embodiment are shown in parentheses, the present invention is not limited thereto.

(1) An aerosol inhaler, including: a first branch circuit (first series circuit C1) that includes a load (load 21), which heats an aerosol source and whose electric resistance value has correlation with a temperature thereof, a first known resistor (first element 63), and a first node connecting the load and the first known resistor in series;

a second branch circuit (second series circuit C2) that includes a second known resistor (second element 64), a third known resistor (third element 65), and a second node connecting the second known resistor and the third known resistor in series, the second branch circuit being connected in parallel with the first branch circuit;

an operational amplifier (operational amplifier 56) of which a non-inverting input terminal (non-inverting input terminal 56a) is connected to one of the first node and the second node, and of which an inverting input terminal (inverting input terminal 56b) is connected to the other of the first node and the second node; and a control device (MCU 50) having an upper limit temperature (upper-limit operating temperature $T_{upper}$) for stopping heating the load and a lower limit temperature (lower-limit operating temperature $T_{lower}$) for not allowing electricity discharge to the load, in which a differential input of the operational amplifier
is equal to potential of a negative power supply terminal (negative power supply terminal 56e) of the operational amplifier or a minimum value that is acquirable by the operational amplifier, in an upper-bound temperature range or a lower-bound temperature range of an operating temperature set in which the upper limit temperature is a greatest element and the lower limit temperature is a least element, or
is equal to the potential of the negative power supply terminal of the operational amplifier or the minimum value that is acquirable by the operational amplifier, in a subset of the operating temperature set, the subset including the upper limit temperature or the lower limit temperature.

According to (1), the differential input of the operational amplifier is equal to the potential of the negative power supply terminal of the operational amplifier or the minimum value that is acquirable by the operational amplifier, in the upper-bound temperature range or the lower-bound temperature range of the operating temperature set in which the upper limit temperature is the greatest element and the lower limit temperature is the least element or in the subset of the operating temperature set, the subset including the upper limit temperature and the lower limit temperature, and thus the temperature of the load can be detected with high accuracy in an appropriate temperature range.

That is, if the temperature of the load can be detected in a wide temperature range based on an output signal of the operational amplifier, it is necessary to provide a margin to electric resistance values of the elements in the first and second branch circuits from a viewpoint of preventing sticking of the differential input and an output signal of the operational amplifier. When the electric resistance values of the elements in the first and second branch circuits have a margin, the differential input of the operational amplifier tends to increase. Further, when the differential input of the operational amplifier is increased, it is difficult to increase an amplification factor of the operational amplifier from a viewpoint of preventing sticking of the output signal of the operational amplifier. Therefore, it is difficult to detect the temperature of the load with high accuracy.

On the other hand, according to (1), in a temperature range where there is little need to be able to detect the temperature of the load for managing the temperature of the load, a difference between potential input to the non-inverting input terminal and potential input to the inverting input terminal of the operational amplifier is allowed to be smaller than the potential of the negative power supply terminal or the minimum value that is acquirable by the operational amplifier. The temperature range refers to the upper-bound temperature range or the lower-bound temperature range of the operating temperature set in which the upper limit temperature is the greatest element and the lower limit temperature is the least element, or refers to the subset, of the operating temperature set, including the upper limit temperature or the lower limit temperature. Therefore, in (1), since providing a margin to the electric resistance values of the elements in the first and second branch circuits in order to excessively suppress sticking of the output signal of the operational amplifier is unnecessary, the differential input of the operational amplifier can be reduced and the amplification factor of the operational amplifier can be increased accordingly. Accordingly, it is possible to detect the temperature of the load with high accuracy in an appropriate temperature range.

(2) The aerosol inhaler according to (1),
in which in the subset, the differential input of the operational amplifier is equal to the potential of the negative power supply terminal of the operational amplifier or the minimum value that is acquirable by the operational amplifier.

According to (2), in the subset, the differential input of the operational amplifier is equal to the potential of the negative power supply terminal of the operational amplifier or the minimum value that is acquirable by the operational amplifier, and thus the temperature of the load can be detected with high accuracy in an appropriate temperature range.

(3) The aerosol inhaler according to (2),
in which the control device is capable of performing control to restrict the temperature of the load to a target temperature when the aerosol source is heated, and
in which the subset does not include the target temperature as an element.

According to (3), when the temperature of the load is at least the target temperature, the differential input of the operational amplifier can be prevented from being equal to the potential of the negative power supply terminal of the operational amplifier or the minimum value that is acquirable by the operational amplifier. Therefore, when the temperature of the load is at least the target temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the control device can accurately restrict the temperature of the load to the target temperature.

(4) The aerosol inhaler according to (1),
in which the control device is configured to be able to perform control to restrict the temperature of the load to a target temperature when the aerosol source is heated, and
in which the differential input of the operational amplifier is larger than the potential of the negative power supply terminal of the operational amplifier or the minimum value that is acquirable by the operational amplifier, in a set in which the target temperature is included as an element and a temperature of the target temperature+50° C. is a greatest element or an upper limit.

According to (4), when the temperature of the load is included in a temperature range in which the target temperature is included as an element and a temperature of the target temperature+50° C. is a greatest element or an upper limit, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the control device can accurately restrict the temperature of the load to the target temperature.

(5) The aerosol inhaler according to (4),
in which the set is a set in which a temperature of the target temperature −50° C. is a least element or a lower limit.

According to (5), even when the temperature of the load is further in a temperature range in which a temperature of the target temperature −50° C. is a least element or a lower limit, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the control device can accurately restrict the temperature of the load to the target temperature.

(6) The aerosol inhaler according to (4),
in which the set is a set in which the lower limit temperature is a least element or a lower limit.

According to (6), even when the temperature of the load is around the lower limit temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier. Accordingly, for example, in a temperature range in which calibration for detecting the temperature of the load is performed, the sticking of the output signal of the operational amplifier can be suppressed, which occurs due to the differential input of the operational amplifier being smaller than the potential of the negative power supply terminal, and the calibration can be appropriately performed.

(7) The aerosol inhaler according to (4),
in which the control device is configured to control a pulse width of power supplied to the load based on a difference between the target temperature and the temperature of the load, and
in which the set is a set in which a temperature at which the pulse width is smaller than a maximum value is a least element.

According to (7), when the temperature of the load is a temperature at which the pulse width of the power supplied to the load can be changed, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the control device can accurately restrict the temperature of the load to the target temperature.

(8) The aerosol inhaler according to (1),
in which the differential input of the operational amplifier is larger than the potential of the negative power supply terminal of the operational amplifier or the minimum value that is acquirable by the operational amplifier, in a set in which the upper limit temperature is included as an element and a temperature of the upper limit temperature −50° C. is a least element or a lower limit.

According to (8), when the temperature of the load is included in a temperature range in which the upper limit temperature is included and a temperature of the upper limit temperature+50° C. is a maximum element or an upper limit, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier. Therefore, when the temperature of the load is included in the temperature range in which the upper limit temperature is included and a temperature of the upper limit temperature+50° C. is a maximum element or an upper limit, it is possible to detect the temperature of the load with high accuracy.

(9) The aerosol inhaler according to (8),
in which the load is connected to a low potential side of the first known resistor in the first branch circuit,
in which the first branch circuit is connected to the non-inverting input terminal of the operational amplifier,
in which the set has the temperature of the upper limit temperature −50° C. as a lower limit, and
in which the differential input of the operational amplifier is equal to the potential of the negative power supply terminal of the operational amplifier or the minimum value that is acquirable by the operational amplifier, at the temperature of the upper limit temperature −50° C.

According to (9), when the temperature of the load is around the upper limit temperature (when a difference between the temperature of the load and the upper limit temperature is less than 50° C.), the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier. Therefore, when the temperature of the load is around the upper limit temperature, the temperature of the load can be detected with high accuracy.

(10) The aerosol inhaler according to (8),
in which the load is connected to a low potential side of the first known resistor in the first branch circuit,
in which the first branch circuit is connected to the non-inverting input terminal of the operational amplifier,
in which the set has the temperature of the upper limit temperature −50° C. as a lower limit, and
in which in a case where the load at the temperature of the upper limit temperature −50° C. has an electric resistance value that is different by −10% from an electric resistance value at which the differential input of the operational amplifier is equal to the potential of the negative power supply terminal of the operational amplifier or the minimum value that is acquirable by the operational amplifier at the temperature of the upper limit temperature −50° C., the differential input of the operational amplifier is equal to the potential of the negative power supply terminal of the operational amplifier or the minimum value that is acquirable by the operational amplifier, at the temperature of the upper limit temperature −50° C.

According to (10), even if the electric resistance value of the load varies by −10% from a reference value due to a product error or the like, when the temperature of the load is around the upper limit temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the temperature of the load can be detected with high accuracy.

(11) The aerosol inhaler according to (8), in which the load is connected to a high potential side of the first known resistor in the first branch circuit, in which the first branch circuit is connected to the inverting input terminal of the operational amplifier, in which the set has the temperature of the upper limit temperature −50° C. as a lower limit, and in which the differential input of the operational amplifier is equal to the potential of the negative power supply terminal of the operational amplifier or the minimum value that is acquirable by the operational amplifier, at the temperature of the upper limit temperature −50° C.

According to (11), when the temperature of the load is around the upper limit temperature (when a difference between the temperature of the load and the upper limit temperature is less than 50° C.), the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier. Therefore, when the temperature of the load is around the upper limit temperature, the temperature of the load can be detected with high accuracy.

(12) The aerosol inhaler according to (8), in which the load is connected to a high potential side of the first known resistor in the first branch circuit, in which the first branch circuit is connected to the inverting input terminal of the operational amplifier, in which the set has the temperature of the upper limit temperature −50° C. as a lower limit, and in which in a case where the load at the upper limit temperature −50° C. has an electric resistance value that is different by −10% from an electric resistance value at which the differential input of the operational amplifier is equal to the potential of the negative power supply terminal of the operational amplifier or the minimum value that is acquirable by the operational amplifier at the temperature of the upper limit temperature −50° C., the differential input of the operational amplifier is equal to the potential of the negative power supply terminal of the operational amplifier or the minimum value that is acquirable by the operational amplifier, at the temperature of the upper limit temperature −50° C.

According to (12), even if the electric resistance value of the load varies by −10% from a reference value due to a product error or the like, when the temperature of the load is around the upper limit temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the temperature of the load can be detected with high accuracy.

(13) The aerosol inhaler according to (8), in which the load is connected to a high potential side of the first known resistor in the first branch circuit, in which the first branch circuit is connected to the non-inverting input terminal of the operational amplifier, and in which the differential input of the operational amplifier is equal to the potential of the negative power supply terminal of the operational amplifier or the minimum value that is acquirable by the operational amplifier, at the upper limit temperature.

According to (13), when the temperature of the load is lower than the upper limit temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier. Therefore, when the temperature of the load is lower than the upper limit temperature, the temperature of the load can be detected with high accuracy.

(14) The aerosol inhaler according to (8), in which the load is connected to a high potential side of the first known resistor in the first branch circuit, in which the first branch circuit is connected to the non-inverting input terminal of the operational amplifier, and in which in a case where the load at the upper limit temperature has an electric resistance value that is different by −10% from an electric resistance value at which the differential input of the operational amplifier is equal to the potential of the negative power supply terminal of the operational amplifier or the minimum value that is acquirable by the operational amplifier at the upper limit temperature, the differential input of the operational amplifier is equal to the potential of the negative power supply terminal of the operational amplifier or the minimum value that is acquirable by the operational amplifier, at the upper limit temperature.

According to (14), even if the electric resistance value of the load varies by −10% from a reference value due to a product error or the like, when the temperature of the load is lower than the upper limit temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the temperature of the load can be detected with high accuracy.

(15) The aerosol inhaler according to (8), in which the load is connected to a low potential side of the first known resistor in the first branch circuit, in which the first branch circuit is connected to the inverting input terminal of the operational amplifier, and in which the differential input of the operational amplifier is equal to the potential of the negative power supply terminal of the operational amplifier or the minimum value that is acquirable by the operational amplifier, at the upper limit temperature.

According to (15), when the temperature of the load is lower than the upper limit temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier. Therefore, when the temperature of the load is lower than the upper limit temperature, the temperature of the load can be detected with high accuracy.

(16) The aerosol inhaler according to (12) or (13), in which the load is connected to a low potential side of the first known resistor in the first branch circuit, in which the first branch circuit is connected to the inverting input terminal of the operational amplifier, and in which in a case where the load at the upper limit temperature has an electric resistance value that is different by −10% from an electric resistance value at which the differential input of the operational amplifier is equal to the potential of the negative power supply terminal of the operational amplifier or the minimum value that is acquirable by the operational amplifier at the upper limit temperature, the differential input of the operational amplifier is equal to the potential of the negative power supply terminal of the operational amplifier or the minimum value that is acquirable by the operational amplifier, at the upper limit temperature.

According to (16), even if the electric resistance value of the load varies by −10% from a reference value due to a product error or the like, when the temperature of the load is lower than the upper limit temperature, the sticking of the output signal of the operational amplifier can be suppressed, which occurs due to the difference between the potential input to the non-inverting input terminal of the operational amplifier and the potential input to the inverting input terminal thereof being smaller than the potential of the negative power supply terminal or the minimum value that is acquirable by the operational amplifier, and the temperature of the load can be detected with high accuracy.

(17) A power supply unit (power supply unit 10) for an aerosol inhaler (aerosol inhaler 1) having a power supply capable of discharging electricity to a load (load 21) that heats an aerosol generation source and whose electric resistance value has correlation with a temperature thereof, the power supply unit of an aerosol inhaler including:

a first branch circuit (first series circuit C1) that includes a first known resistor (first element 63), and a first node connecting the load and the first known resistor in series;

a second branch circuit (second series circuit C2) that includes a second known resistor (second element 64), a third known resistor (third element 65), and a second node connecting the second known resistor and the third known resistor in series, the second branch circuit being connected in parallel with the first branch circuit;

an operational amplifier (operational amplifier 56) of which a non-inverting input terminal (non-inverting input terminal 56a) is connected to one of the first node and the second node, and of which an inverting input terminal (inverting input terminal 56b) is connected to the other of the first node and the second node; and a control device (MCU 50) having an upper limit temperature (upper-limit operating temperature $T_{upper}$) for stopping heating the load and a lower limit temperature (lower-limit operating temperature $T_{lower}$) for not allowing electricity discharge to the load, in which a differential input of the operational amplifier
is equal to potential of a negative power supply terminal (negative power supply terminal 56e) of the operational amplifier or a minimum value that is acquirable by the operational amplifier, in an upper-bound temperature range or a lower-bound temperature range of an operating temperature set in which the upper limit temperature is a greatest element and the lower limit temperature is a least element, or is equal to the potential of the negative power supply terminal of the operational amplifier or the minimum value that is acquirable by the operational amplifier, in a subset of the operating temperature set, the subset including the upper limit temperature or the lower limit temperature.

According to (17), the differential input of the operational amplifier is equal to the potential of the negative power supply terminal of the operational amplifier or the minimum value that is acquirable by the operational amplifier, in the upper-bound temperature range or the lower-bound temperature range of the operating temperature set in which the upper limit temperature is the greatest element and the lower limit temperature is the least temperature or in the subset of the operating temperature set, the subset including the upper limit temperature and the lower limit temperature, and thus the element of the load can be detected with high accuracy in an appropriate temperature range.

According to the present invention, a temperature of a load used to generate an aerosol can be detected with high accuracy in an appropriate temperature range.

The invention claimed is:

1. An aerosol inhaler, comprising:
a first branch circuit that includes a load, which heats an aerosol source and whose electric resistance value has correlation with a temperature thereof, a first known resistor, and a first node connecting the load and the first known resistor in series;
a second branch circuit that includes a second known resistor, a third known resistor, and a second node connecting the second known resistor and the third known resistor in series, the second branch circuit being connected in parallel with the first branch circuit;
an operational amplifier of which a non-inverting input terminal is connected to one of the first node and the second node, and of which an inverting input terminal is connected to the other of the first node and the second node; and
a control device having an upper limit temperature for stopping heating the load and a lower limit temperature for not allowing electricity discharge to the load,
wherein a differential input of the operational amplifier is larger than potential of a negative power supply terminal of the operational amplifier or a minimum value that is acquirable by the operational amplifier, in a first temperature range including the upper limit temperature, and is equal to the potential of the negative power supply terminal of the operational amplifier or the minimum value that is acquirable by the operational amplifier, in a second temperature range including the lower limit temperature and being different from the first temperature range.

2. The aerosol inhaler according to claim 1,
wherein the control device is capable of performing control to restrict the temperature of the load to a target temperature when the aerosol source is heated, and
wherein the first temperature range includes the target temperature, and
wherein the second temperature range does not include the target temperature.

3. The aerosol inhaler according to claim 1,
wherein the control device is configured to be able to perform control to restrict the temperature of the load to a target temperature when the aerosol source is heated, and
wherein the differential input of the operational amplifier is larger than the potential of the negative power supply terminal of the operational amplifier or the minimum value that is acquirable by the operational amplifier, in the first temperature range in which the target temperature is included and a temperature of the target temperature+50° C. is an upper limit.

4. The aerosol inhaler according to claim 3,
wherein the first temperature range has a temperature of the target temperature −50° C. as a lower limit.

5. The aerosol inhaler according to claim 3,
wherein the control device is configured to control a pulse width of power supplied to the load based on a difference between the target temperature and the temperature of the load, and
wherein the first temperature range has a temperature as a lower limit at which the pulse width is smaller than a maximum value.

6. The aerosol inhaler according to claim 1,
wherein the differential input of the operational amplifier is larger than the potential of the negative power supply terminal of the operational amplifier or the minimum value that is acquirable by the operational amplifier, in the first temperature range in which a temperature of the upper limit temperature −50° C. is a lower limit.

7. The aerosol inhaler according to claim 1,
wherein the load is connected to a low potential side of the first known resistor in the first branch circuit,
wherein the first branch circuit is connected to the non-inverting input terminal of the operational amplifier, and
wherein the differential input of the operational amplifier is equal to the potential of the negative power supply terminal of the operational amplifier or the minimum value that is acquirable by the operational amplifier, at the temperature of the upper limit temperature −50° C.

8. The aerosol inhaler according to claim 1,
wherein the load is connected to a low potential side of the first known resistor in the first branch circuit,
wherein the first branch circuit is connected to the non-inverting input terminal of the operational amplifier, and
wherein in a case where the load at a temperature of the upper limit temperature −50° C. has an electric resistance value that is different by −10% from an electric resistance value at which the differential input of the operational amplifier is equal to the potential of the negative power supply terminal of the operational amplifier or the minimum value that is acquirable by the operational amplifier at the temperature of the upper limit temperature −50° C., the differential input of the operational amplifier is equal to the potential of the negative power supply terminal of the operational amplifier or the minimum value that is acquirable by the operational amplifier, at the temperature of the upper limit temperature −50° C.

9. The aerosol inhaler according to claim 1,
wherein the load is connected to a high potential side of the first known resistor in the first branch circuit,
wherein the first branch circuit is connected to the inverting input terminal of the operational amplifier, and
wherein the differential input of the operational amplifier is equal to the potential of the negative power supply terminal of the operational amplifier or the minimum value that is acquirable by the operational amplifier, at a temperature of the upper limit temperature −50° C.

10. The aerosol inhaler according to claim 1,
wherein the load is connected to a high potential side of the first known resistor in the first branch circuit,
wherein the first branch circuit is connected to the inverting input terminal of the operational amplifier, and
wherein in a case where the load at a temperature of the upper limit temperature −50° C. has an electric resistance value that is different by −10% from an electric resistance value at which the differential input of the operational amplifier is equal to the potential of the negative power supply terminal of the operational amplifier or the minimum value that is acquirable by the operational amplifier at the temperature of the upper limit temperature −50° C., the differential input of the operational amplifier is equal to the potential of the negative power supply terminal of the operational amplifier or the minimum value that is acquirable by the operational amplifier, at the temperature of the upper limit temperature −50° C.

11. A power supply unit of an aerosol inhaler having a power supply capable of discharging electricity to a load that heats an aerosol generation source and whose electric resistance value has correlation with a temperature thereof, the power supply unit of an aerosol inhaler comprising:
a first branch circuit that includes a first known resistor, and a first node connecting the load and the first known resistor in series;
a second branch circuit that includes a second known resistor, a third known resistor, and a second node connecting the second known resistor and the third known resistor in series, the second branch circuit being connected in parallel with the first branch circuit;
an operational amplifier of which a non-inverting input terminal is connected to one of the first node and the second node, and of which an inverting input terminal is connected to the other of the first node and the second node; and
a control device having an upper limit temperature for stopping heating the load and a lower limit temperature for not allowing electricity discharge to the load,
wherein a differential input of the operational amplifier is larger than potential of a negative power supply terminal of the operational amplifier or a minimum value that is acquirable by the operational amplifier, in a first temperature range including the upper limit temperature, and is equal to the potential of the negative power supply terminal of the operational amplifier or the minimum value that is acquirable by the operational amplifier, in a second temperature range including the lower limit temperature and being different from the first temperature range.

* * * * *